US012036213B2

(12) United States Patent
Geva et al.

(10) Patent No.: US 12,036,213 B2
(45) Date of Patent: Jul. 16, 2024

(54) PRIDOPIDINE FOR TREATING DRUG INDUCED DYSKINESIAS

(71) Applicant: PRILENIA NEUROTHERAPEUTICS LTD., Herzliya (IL)

(72) Inventors: Michal Geva, Even-Yehuda (IL); Aric Orbach, Rehovot (IL); Michael Hayden, Herzliya (IL)

(73) Assignee: PRILENIA NEUROTHERAPEUTICS LTD., Yakum (IL)

( * ) Notice: Subject to any disclaimer, the term of this patent is extended or adjusted under 35 U.S.C. 154(b) by 649 days.

(21) Appl. No.: 17/315,667

(22) Filed: May 10, 2021

(65) Prior Publication Data

US 2021/0275512 A1 Sep. 9, 2021

Related U.S. Application Data

(63) Continuation-in-part of application No. PCT/IL2019/051313, filed on Nov. 28, 2019, and a continuation-in-part of application No. 16/436,947, filed on Jun. 11, 2019, now Pat. No. 11,000,519, which is a continuation of application No. 16/377,577, filed on Apr. 8, 2019, now abandoned, which is a continuation-in-part of application No. PCT/US2018/048920, filed on Aug. 30, 2018.

(60) Provisional application No. 62/772,814, filed on Nov. 29, 2018, provisional application No. 62/649,184, filed on Mar. 28, 2018, provisional application No. 62/556,314, filed on Sep. 8, 2017.

(51) Int. Cl.
| | |
|---|---|
| *A61K 31/451* | (2006.01) |
| *A61K 9/00* | (2006.01) |
| *A61K 45/06* | (2006.01) |
| *A61P 25/14* | (2006.01) |
| *A61P 25/16* | (2006.01) |
| *A61K 31/198* | (2006.01) |

(52) U.S. Cl.
CPC .......... *A61K 31/451* (2013.01); *A61K 9/0053* (2013.01); *A61K 45/06* (2013.01); *A61P 25/14* (2018.01); *A61P 25/16* (2018.01); *A61K 31/198* (2013.01)

(58) Field of Classification Search
CPC .... A61K 31/451; A61K 9/0053; A61K 45/06; A61K 31/198; A61P 25/14; A61P 25/16
USPC ....................................................... 514/317
See application file for complete search history.

(56) References Cited

U.S. PATENT DOCUMENTS

| 6,903,120 | B2 | 6/2005 | Sonesson et al. |
|---|---|---|---|
| 7,417,043 | B2 | 8/2008 | Sonesson et al. |
| 7,923,459 | B2 | 5/2011 | Gauthier et al. |
| 9,006,445 | B2 | 4/2015 | Sonesson et al. |
| 9,012,476 | B2 | 4/2015 | Zimmermann et al. |
| 9,139,525 | B2 | 9/2015 | Wikström |
| RE46,117 | E | 8/2016 | Sonesson et al. |
| 9,796,673 | B2 | 10/2017 | Wu et al. |
| 9,814,706 | B2 | 11/2017 | Zimmermann et al. |
| 10,047,049 | B2 | 8/2018 | Barel et al. |
| 10,130,621 | B2 | 11/2018 | Schmidt et al. |
| 10,322,119 | B2 | 6/2019 | Bassan et al. |
| 2013/0197031 | A1 | 8/2013 | Sonesson |
| 2013/0267552 | A1 | 10/2013 | Waters et al. |
| 2013/0331399 | A1 | 12/2013 | Leahy et al. |
| 2014/0088145 | A1 | 3/2014 | Hayden et al. |
| 2015/0202302 | A1 | 7/2015 | Licht et al. |
| 2016/0095847 | A1 | 4/2016 | Sonesson |
| 2016/0166559 | A1 | 6/2016 | Sonesson |
| 2016/0243098 | A1 | 8/2016 | Geva et al. |
| 2017/0020854 | A1 | 1/2017 | Licht et al. |
| 2017/0266170 | A1 | 9/2017 | Waters et al. |
| 2018/0055832 | A1 | 3/2018 | Hayden et al. |
| 2018/0235950 | A1 | 8/2018 | Sonesson |
| 2019/0015401 | A1 | 1/2019 | Sonesson |
| 2019/0030016 | A1 | 1/2019 | Schmidt et al. |
| 2019/0046516 | A1 | 2/2019 | Russ et al. |
| 2019/0192496 | A1 | 6/2019 | Hayden et al. |
| 2019/0209542 | A1 | 7/2019 | Licht et al. |

FOREIGN PATENT DOCUMENTS

| WO | WO 2001/046145 | 6/2001 |
|---|---|---|
| WO | WO 2006/040155 | 4/2006 |
| WO | WO 2008/127188 | 10/2008 |
| WO | WO 2008/155357 | 12/2008 |
| WO | WO 2012/002863 | 3/2012 |

(Continued)

OTHER PUBLICATIONS

Ahlskog, J. E., & Muenter, M. D. (2001). Frequency of levodopa-related dyskinesiasand motor fluctuations as estimated from the cumulative literature. Movement disorders: official journal of the Movement Disorder Society, 16(3), 448-458.

Albanese, A., et al. (2006). A systematic review on the diagnosis and treatment of primary (idiopathic) dystonia and dystonia plus syndromes: report of an EFNS/MDS-ES Task Force. European journal of neurology, 13(5), 433-444.

Albanese, A., et al. (2013). Phenomenology and classification of dystonia: a consensus update. Movement disorders, 28(7), 863-873.

Albanese, A., Sorbo, F. D., Comella, C., Jinnah, H. A., Mink, J. W., Post, B., . . . & Schrag, A. (2013). Dystonia rating scales: critique and recommendations. Movement Disorders, 28(7), 874-883.

(Continued)

*Primary Examiner* — Kristin A Vajda
(74) *Attorney, Agent, or Firm* — Mark S. Cohen; Pearl Cohen; ZEDEK LATZER BARATZ LLP

(57) ABSTRACT

The invention provides a method of treating a subject afflicted with a drug-induced movement disorder including levodopa-induced dyskinesia comprising periodically administering to the subject in need thereof an amount of pridopidine or pharmaceutically acceptable salt thereof effective to treat the subject. The invention further provides a method of treating a subject at risk of developing a drug-induced movement disorder, including levodopa-induced dyskinesia.

29 Claims, 18 Drawing Sheets

(56) References Cited

FOREIGN PATENT DOCUMENTS

| WO | WO 2013/034622 | 3/2013 |
|---|---|---|
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138130 | 9/2016 |
| WO | WO 2017/015609 | 1/2017 |
| WO | WO 2017/015615 | 1/2017 |
| WO | WO 2017/147366 | 8/2017 |
| WO | WO 2018/039475 | 3/2018 |
| WO | WO 2018/039477 | 3/2018 |
| WO | WO 2018/053275 | 3/2018 |
| WO | WO 2018/053280 | 3/2018 |
| WO | WO 2018/053287 | 3/2018 |
| WO | WO 2018/136600 | 7/2018 |
| WO | WO 2019/036358 | 2/2019 |
| WO | WO 2019/046568 | 3/2019 |

OTHER PUBLICATIONS

Bargiotas, P., & Konitsiotis, S. (2013). Levodopa-induced dyskinesias in Parkinson's disease: emerging treatments. Neuropsychiatric disease and treatment, 9, 1605.

Bechtel, N., et al. (2010). Tapping linked to function and structure in premanifest and symptomatic Huntington disease. *Neurology*, 75(24), 2150-2160.

Bezchlibnyk-Butler, K. Z., & Remington, G. J. (1994). Antiparkinsonian drugs in the treatment of neuroleptic-induced extrapyramidal symptoms. The Canadian Journal of Psychiatry, 39(2), 74-84.

Bowie, C. R., & Harvey, P. D. (2006). Administration and interpretation of the Trail Making Test. *Nature protocols*, 1(5), 2277.

Brigham, E. F., et al. (2018). Pharmacokinetic/pharmacodynamic correlation analysis of amantadine for levodopa-induced dyskinesia. Journal of Pharmacology and Experimental Therapeutics, 367(2), 373-381.

Brod, S. A., Lindsey, J. W., & Wolinsky, J. S. (2000). Combination therapy with glatiramer acetate (copolymer-1) and a type I interferon (IFN-α) does not improve experimental autoimmune encephalomyelitis. Annals of neurology, 47(1), 127-131.

Brown, M., et al. (2000). Physical and performance measures for the identification of mild to moderate frailty. *The Journals of Gerontology Series A: Biological Sciences and Medical Sciences*, 55(6), M350-M355.

Brust, P., et al. (2014). Molecular imaging of σ1 receptors in vivo: current status and perspectives. *Current medicinal chemistry*, 21(1), 35-69.

Buspark., (2018), "Buspirone Treatment of Iatrogenic Dyskinesias in Advanced Parkinson' Disease clinical trial—NCT02617017" retrieved from: https://clinicaltrials.gov/ct2/show/NCT02617017.

ClinicalTrials.gov Identifier: NCT00608881; Coenzyme Q10 in Huntington's Disease (HD) (2CARE); clinicaltrials.gov/ct2/show/NCT00608881?term=2CARE%20+Huntington&rank=1; Feb. 6, 2008.

ClinicalTrials.gov Identifier: NCT01306929; Open-label Extension Study of Pridopidine (ACR16) in the Symptomatic Treatment of Huntington Disease (Open-Hart); clinicaltrials.gov/ct2/show/NCT01306929; Mar. 2, 2011.

Craufurd, D., Thompson, J. C., & Snowden, J. S. (2001). Behavioral changes in Huntington disease. *Cognitive and Behavioral Neurology*, 14(4), 219-226.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

Cubo, E., et al. (2001). Early morning off-medication dyskinesias, dystonia, and choreic subtypes. Archives of neurology, 58(9), 1379-1382.

Daneault, J. F., et al. (2013). Drug-induced dyskinesia in Parkinson's disease. Should success in clinical management be a function of improvement of motor repertoire rather than amplitude of dyskinesia?. BMC medicine, 11(1), 76.

De Yebenes, J. G., et al. & MermaiHD study investigators. (2011). Pridopidine for the treatment of motor function in patients with Huntington's disease (MermaiHD): a phase 3, randomised, double-blind, placebo-controlled trial. The Lancet Neurology, 10(12), 1049-1057.

Dizdar, N., et al. (1999). Human pharmacokinetics of L-3, 4-dihydroxyphenylalanine studied with microdialysis. Clinical chemistry, 45(10), 1813-1820.

Exploratory Population Pharmacokinetic Modeling and Simulations With Pridopidine (Report No. CP-13-013). Pharsight Consulting Services, Jul. 10, 2013.

FDA (1999) Guidance for Industry: In Vivo Drug Metabolism/Drug Interaction Studies—Study Design, Data Analysis, and Recommendations for Dosing and Labeling., pp. 1-19.

Food and Drug Administration. The Voice of the Patient, Parkinson's Disease. Public Meeting, Sep. 22, 2015. Report date Apr. 2016 [cited Dec. 21, 2018].

Fox, S. H., et al. (2017). Trial of dextromethorphan/quinidine to treat levodopa-induced dyskinesia in Parkinson's disease. Movement Disorders, 32(6), 893-903. [Abstract].

Gerber, P. E., & Lynd, L. D. (1998). Selective serotonin-reuptake inhibitor-induced movement disorders. Annals of Pharmacotherapy, 32(6), 692-698.

Geva, M., et al. (2016). Pridopidine activates neuroprotective pathways impaired in Huntington Disease. Human molecular genetics, 25(18), 3975-3987.

Goetz, C. G., et al. (2007). Movement Disorder Society-sponsored revision of the Unified Parkinson's Disease Rating Scale (MDS-UPDRS): process, format, and clinimetric testing plan. Movement Disorders, 22(1), 41-47.

Goetz, C. G., et al. (2008). Movement Disorder Society-sponsored revision of the Unified Parkinson's Disease Rating Scale (MDS-UPDRS): scale presentation and clinimetric testing results. Movement disorders: official journal of the Movement Disorder Society, 23(15), 2129-2170.

Goetz, C. G., et al. (2013). Which dyskinesia scale best detects treatment response?. Movement Disorders, 28(3), 341-346.

Goetz, C. G., Nutt, J. G., & Stebbins, G. T. (2008). The unified dyskinesia rating scale: presentation and clinimetric profile. Movement disorders: official journal of the Movement Disorder Society, 23(16), 2398-2403.

Group, T. E. (1990). EuroQol—a new facility for the measurement of health-related quality of life. *Health policy*, 16(3), 199-208.

Guy, W. E. (1976). ECDEU—Abnormal Involuntary Movement Scale (AIMS) Assessment Manual for Psychopharmacology: Revised (DHEW publication No. ADM 76-338). Rockville, MD, US Department of Health, Education and Welfare, Public Health Service, Alcohol, Drug Abuse and Mental Health Administration, NIMH Psychopharmacology Research Branch, Division of Extramural Research Programs, 534-7.

Hauser, R. A., Deckers, F., & Lehert, P. (2004). Parkinson's disease home diary: further validation and implications for clinical trials. Movement Disorders, 19(12), 1409-1413.

Hauser, R. A., et al. (2007). Ten-year follow-up of Parkinson's disease patients randomized to initial therapy with ropinirole or levodopa. Movement Disorders, 22(16), 2409-2417.

History of Changes for Study: NCT03368170., (2018), "Efficacy and Tolerability of IRL790 in Parkinson's Disease Dyskinesia", (v10) retrieved from: https://clinicaltrials.gov/ct2/history/NCT03368170/V_10=View#StudyPageTop, pp. 1-5.

Hocaoglu, M. B., Gaffan, E. A., & Ho, A. K. (2012). The Huntington's Disease health-related Quality of Life questionnaire (HDQoL): a disease-specific measure of health-related quality of life. *Clinical genetics*, 81(2), 117-122.

Huntexil. (2012)—'NeuroSearch A/S reports conclusions from the Multiple Ascending Dose study (MAD) with Huntexil', The NeuroSearch website, 1 page.

(56) References Cited

OTHER PUBLICATIONS

Huntington Study Group Trend-HD Investigators. (2008). Randomized controlled trial of ethyl-eicosapentaenoic acid in Huntington disease. *Archives of neurology*, 65(12), 1582-1589.

Huntington Study Group. (1996) Unified Huntington's Disease Rating Scale: Reliablility and Consistency., Movement Disorders, 11(2), 136-142.

Huntington Study Group. (2001). A randomized, placebo-controlled trial of coenzyme Q10 and remacemide in Huntington's disease. *Neurology*, 57(3), 397-404.

Huntington Study Group. (2003). Dosage effects of riluzole in Huntington's disease: a multicenter placebo-controlled study. *Neurology*, 61(11), 1551-1556.

Huntington Study Group. (2006). Tetrabenazine as antichorea therapy in Huntington disease: a randomized controlled trial. *Neurology*, 66(3), 366-372.

Huntington Study Group Hart Investigators (2013)—A randomized, double-blind, placebo-controlled trial of pridopidine in Huntington's disease. Movement Disorders, vol. 28, not 10, pp. 1407-1415. First published Feb. 28, 2013.

Huot, P., Johnston, T. H., Koprich, J. B., Fox, S. H., & Brotchie, J. M. (2012). L-DOPA pharmacokinetics in the MPTP-lesioned macaque model of Parkinson's disease. Neuropharmacology, 63(5), 829-836.

Huot, P., Johnston, T. H., Koprich, J. B., Fox, S. H., & Brotchie, J. M. (2013). The pharmacology of L-DOPA-induced dyskinesia in Parkinson's disease. Pharmacological reviews, 65(1), 171-222.

International Search Report dated Dec. 3, 2018 for PCT/US2018/048920.

International Search Report dated Jan. 23, 2020 for PCT/IL2019/051313.

Jankelowitz, S. K. (2013). 'Treatment of neurolept-induced tardive dyskinesia', Neuropsychiatric disease and treatment. pp. 1371-1380.

Jenner, P. (2008). Molecular mechanisms of L-DOPA-induced dyskinesia. Nature Reviews Neuroscience, 9(9), 665.

Joffres, C., Graham, J., & Rockwood, K. (2000). Qualitative analysis of the clinician interview-based impression of change (Plus): methodological issues and implications for clinical research. *International psychogeriatrics*, 12(3), 403.

Johnson, AC and Paulsen JS. Huntington's Disease: A Guide for Professionals. (2014) D. Lovecky and K. Tarapata eds. Huntington's Disease Society of Americas (HDSA).

Johnston, T. H., et al. (2013). TC-8831, a nicotinic acetylcholine receptor agonist, reduces L-DOPA-induced dyskinesia in the MPTP macaque. Neuropharmacology, 73, 337-347.

Johnston, T. H., et al. (2018). Pridopidine, a clinic-ready compound, reduces 3, 4-dihydroxyphenylalanine-induced dyskinesia in Parkinsonian macaques. Movement Disorders, 34(5), 708-716.

Kingma, E. M., et al. (2008). Behavioural problems in Huntington's disease using the Problem Behaviours Assessment. *General hospital psychiatry*, 30(2), 155-161.

Kumar, N., Van Gerpen, J. A., Bower, J. H., & Ahlskog, J. E. (2005). Levodopa-dyskinesia incidence by age of Parkinson's disease onset. Movement disorders, 20(3), 342-344.

Lee, C. S. (2001). Levodopa-induced dyskinesia: Mechanisms and management. British Columbia Medical Journal, 43(4), 206-209.

Liang, C. C., et al. (2014). TorsinA hypofunction causes abnormal twisting movements and sensorimotor circuit neurodegeneration. *The Journal of clinical investigation*, 124(7), 3080-3092.

Mahant, N., McCusker, E. A., Byth, K., Graham, S., & Huntington Study Group. (2003). Huntington's disease: clinical correlates of disability and progression. *Neurology*, 61(8), 1085-1092.

Manson, A., Stirpe, P., & Schrag, A. (2012). Levodopa-induced-dyskinesias clinical features, incidence, risk factors, management and impact on quality of life. Journal of Parkinson's disease, 2(3), 189-198.

Marder, K., Zhao, H., Myers, R. H., Cudkowicz, M., Kayson, E., Kieburtz, K., . . . & Shoulson, I. (2000). Rate of functional decline in Huntington's disease. Neurology, 54(2), 452-452.

Mestre, T., et al. (2009). Therapeutic interventions for symptomatic treatment in Huntington's disease. *Cochrane Database of Systematic Reviews*, (3).

Movement Disorder Society Task Force on Rating Scales for Parkinson's Disease. (2003). The unified Parkinson's disease rating scale (UPDRS): status and recommendations. Movement Disorders, 18(7), 738-750.

Myers, R. H., et al. (1991). Factors associated with slow progression in Huntington's disease. *Archives of neurology*, 48(8), 800-804.

Natesan, S., et al. (2006). The dopamine stabilizers (S)-(−)-(3-methanesulfonyl-phenyl)-1-propyl-piperidine [(−)-OSU6162] and 4-(3-methanesulfonylphenyl)-1-propyl-piperidine (ACR16) show high in vivo D2 receptor occupancy, antipsychotic-like efficacy, and low potential for motor side effects in the rat. *Journal of Pharmacology and Experimental Therapeutics*, 318(2), 810-818.

National Research Council. (2010). Guide for the care and use of laboratory animals. National Academies Press.

Ozelius L, Lubarr N. DYT1 Early-Onset Isolated Dystonia. Apr. 14, 1999 [Updated Nov. 17, 2016]. In: Adam MP, Ardinger HH, Pagon RA, et al., editors. GeneReviews® [Internet]. Seattle (WA): University of Washington, Seattle; 1993-2021. Available from: https://www.ncbi.nlm.nih.gov/books/NBK1492/.

Ozelius, L. J., et al. (1997). The early-onset torsion dystonia gene (DYT1) encodes an ATP-binding protein. *Nature genetics*, 17(1), 40-48.

P. Inacio: (2018)"Lundbeck Acquires Rights to Develop Foliglurax Therapy Candidate to Treat Parkinson's" retrieved from: https://parkinsonsnewstoday.com/2018/03/21/lundbeck-acquires-rights-develop-parkinsons-disease-therapy-candidate-foliglurax/, pp. 1-6.

Parkinson Study Group. (2004). Levodopa and the progression of Parkinson's disease. New England Journal of Medicine, 351(24), 2498-2508.

PDR 2017 Amantadine hydrochloride—Drug Summary, PDR (Prescribers' Digital Reference), http://www.pdr.net/drug-summary/Amantadine-Hydrochloride-Capsules-amantadine-hydrochloride-1475 accessed Sep. 7, 2017.

PDR 2017 Amantadine hydrochloride—Drug Summary, PDR (Prescribers' Digital Reference), http://www.pdr.net/drug-summary/Amantadine-Hydrochloride-Tablets-amantadine-hydrochloride-2441 accessed Sep. 7, 2017.

Podsiadlo, D., & Richardson, S. (1991). The timed "Up & Go": a test of basic functional mobility for frail elderly persons. *Journal of the American geriatrics Society*, 39(2), 142-148.

Poewe, W., & Mahlknecht, P. (2009). The clinical progression of Parkinson's disease. Parkinsonism & related disorders, 15, S28-S32.

Ponten, H., et al. (2010). In vivo pharmacology of the dopaminergic stabilizer pridopidine. European journal of pharmacology, 644(1-3), 88-95.

Ponten, H., et al. (2013). The dopaminergic stabilizer pridopidine decreases expression of L-DOPA-induced locomotor sensitisation in the rat unilateral 6-OHDA model. European journal of pharmacology, 698(1-3), 278-285.

Rabinovich-Guilatt et al. (2016)—The effect of mild and moderate renal impairment on the pharmacokinetics of pridopidine, a new drug for Huntington's disease—British journal of Clinical pharmacology, 81(2), 246-255.

Rao, A. K., et al. (2009). Clinical measurement of mobility and balance impairments in Huntington's disease: validity and responsiveness. *Gait & posture*, 29(3), 433-436.

Rascol, O., et al. (2000). A five-year study of the incidence of dyskinesia in patients with early Parkinson's disease who were treated with ropinirole or levodopa. New England Journal of Medicine, 342(20), 1484-1491.

Sahlholm, K., Århem, P., Fuxe, K., & Marcellino, D. (2013). The dopamine stabilizers ACR16 and (−)-OSU6162 display nanomolar affinities at the σ-1 receptor. Molecular psychiatry, 18(1), 12.

Sahlholm, K., et al. (2015). Pridopidine selectively occupies sigma-1 rather than dopamine D2 receptors at behaviorally active doses. Psychopharmacology, 232(18), 3443-3453.

(56) References Cited

OTHER PUBLICATIONS

Segawa, M., & Nomura, Y. (Jul. 2014). Genetics and pathophysiology of primary dystonia with special emphasis on DYT1 and DYT5. In *Seminars in neurology* (vol. 34, No. 03, pp. 306-311). Thieme Medical Publishers.

Shoulson, I., & Fahn, S. (1979). Huntington disease: clinical care and evaluation. Neurology, 29(1), 1-1.

Slifstein, M., et al. (2010). Striatal and extrastriatal dopamine release measured with PET and [18F] fallypride. Synapse, 64(5), 350-362.

Standaert, D. G. (2011). Update on the pathology of dystonia. *Neurobiology of Disease*, 42(2), 148-151.

Tedroff, J., et al. (Jan. 2004). A pilot study of the novel dopamine stabiliser ACR16 in advanced Parkinson's disease. In Movement Disorders (vol. 19, pp. S201-S202). Div John Wiley & Sons Inc, 111 River St, Hoboken, NJ 07030 USA: Wiley-Liss.

Thanvi, B., Lo, N., & Robinson, T. (2007). Levodopa-induced dyskinesia in Parkinson's disease: clinical features, pathogenesis, prevention and treatment. Postgraduate medical Journal, 83(980), 384-388.

Tison, F., et al. (2016). A phase 2A trial of the novel mGluR5-negative allosteric modulator dipraglurant for levodopa-induced dyskinesia in Parkinson's disease. Movement Disorders, 31(9), 1373-1380. [Abstract].

Verbeek, D. S., & Gasser, T. (2017). Unmet needs in dystonia: genetics and molecular biology—how many dystonias?. *Frontiers in neurology*, 7, 241.

Woods, S. W., et al. (2008). Effects of levetiracetam on tardive dyskinesia: a randomized, double-blind, placebo-controlled study. The Journal of Clinical Psychiatry, 69(4), 546-554. [Abstract].

PRIDOPIDINE FOR TREATING DRUG INDUCED DYSKINESIAS

CROSS REFERENCE TO RELATED APPLICATIONS

This application is a Continuation-in-Part of U.S. patent application Ser. No. 16/436,947 filed on Jun. 11, 2019, which is a Continuation of U.S. patent application Ser. No. 16/377,577 filed on Apr. 8, 2019, which is a Continuation-in-Part of International Application No. PCT/US2018/048920, filed Aug. 30, 2018, which claims the benefit of U.S. Provisional Application No. 62/556,314, filed Sep. 8, 2017, and of U.S. Provisional Application No. 62/649,184, filed Mar. 28, 2018, the entire contents of which are hereby incorporated by reference herein;

This Application is a Continuation-in-Part Application from International Patent Application No. PCT/IL2019/051313 filed Nov. 28, 2019 which claims the benefit of U.S. Provisional Application No. 62/772,814, filed Nov. 29, 2018, the entire contents of which are hereby incorporated by reference herein.

BACKGROUND

Drug Induced Dyskinesias

Dyskinesias are abnormal, involuntary movements which may appear as jerking, twisting or writhing of parts of the body. There are several different types of dyskinesias, which can be categorized as chorea, dystonia, myoclonus, tremor and paroxysmal tardive (late-onset type). Drug-induced movement disorders (DIMDs) may be elicited by different pharmaceutical agents, which modulate dopamine neurotransmission as well as other neurotransmission in the central nervous system such as serotonin, adrenaline and acetylcholine neurotransmission. The major groups of drugs responsible for DIMDs include antidepressants, antipsychotics, antiepileptics, antimicrobials, antiarrhythmics, mood stabilisers and gastrointestinal drugs, among others. These movement disorders include, without limitation, parkinsonism, tardive dyskinesia, chorea, dystonia, tremor, akathisia, athetosis, myoclonus or tics.

Parkinson's Disease and Levodopa-Induced Dyskinesias

Parkinson's disease (PD) is a degenerative disorder characterized by the loss of substantia nigra pars compacta dopaminergic neurons and the subsequent loss of dopaminergic input to the striatum. As the degenerative process evolves, dopamine replacement therapy becomes necessary to help alleviate motor dysfunction.

Dyskinesias are common in Parkinson's disease (PD) and can be separated into a) dyskinesias resulting from the disease process itself, and b) dyskinesias that are the side-effect of levodopa (L-DOPA) medication given to treat symptoms of PD (Levodopa-Induced Dyskinesia, LID) (Cubo 2001).

Levodopa, the most effective agent to alleviate motor dysfunction in Parkinson's disease patients, is associated with the development of dyskinesias with chronic use. Levodopa Induced Dyskinesia (LID) is a major complication of dopamine-replacement therapy in PD ("PD-LID"; Kumar 2005, Manson 2012, Poewe 2009). Other dopamine agonist therapies may induce dyskinesia in PD patients.

The levodopa-induced dyskinesias occur in the majority of the PD patients and initially are mild, progressing to a complex and severe disorder that interferes with motor function, speech, coordination and social activity. LID can adversely affect the quality of life for Parkinson's disease patients.

Peak-dose dyskinesias are the most prevalent type of dyskinesia. They occur during peaks of levodopa-derived dopamine in the brain, when the patient is otherwise experiencing a beneficial response (the 'on' state). Peak dose dyskinesias worsen with increases in dopaminergic therapy and lessen with reductions in dopaminergic therapy. Some patients exhibit diphasic dyskinesia, which occurs when levodopa-derived dopamine concentrations are increasing or decreasing and the patient is shifting between 'on' and 'off' states.

The therapeutic and preventative strategies for LID include using a lower dosage of levodopa, employing other dopamine agonists as initial therapy in Parkinson's disease, amantadine, atypical neuroleptics, and neurosurgery.

The value of current therapies for Parkinson's disease (PD), particularly levodopa (L-DOPA), is limited by significant complications of long-term treatment, especially levodopa-induced dyskinesia (LID). While amantadine (AMT) is already employed clinically for the treatment of established dyskinesia, though generally in an off-label capacity, its therapeutic utility is limited by several factors. It is poorly tolerated by many patients (40-50%) and its use is often compromised by sedation and cognitive problems.

Pridopidine

Pridopidine (formerly ACR16, Huntexil®, TV-7820) is a drug in development for the treatment of patients with Huntington's disease. The chemical name of pridopidine base is 4-(3-(methylsulfonyl)phenyl)-1-propylpiperidine, and its Chemical Registry Number is CAS 346688-38-8 (CSID:7971505, 2016). The Chemical Registry number of pridopidine hydrochloride is 882737-42-0 (CSID:25948790 2016).

Pridopidine demonstrates high affinity binding to the sigma-1 receptor ($\sigma_1$R, or S1R) (Internal studies; Sahlholm 2013) and low affinity binding to several other CNS targets, including receptors for dopamine, serotonin, 5-HT1A, 5-HT2A and 5-HT7; adrenergic alpha-1, adrenergic alpha-2A and alpha-2C receptors, dopamine D3 and dopamine D2 (D2R) receptors; and muscarinic M2 and histamine H3 receptors (Johnston et al., 2019; Ponten 2013).

Pridopidine has been shown to modulate motor activity by either suppressing hyperactivity or enhancing hypoactivity. The neuroprotective properties of pridopidine are suggested to be attributed to its high affinity to the S1R, while the motor activity of pridopidine may be mediated primarily by its moderate-affinity targets, including antagonistic activity at the dopamine D2 receptor (Ponten 2010, Sahlholm 2015).

The S1R is an endoplasmic reticulum (ER) chaperone protein which is implicated in cellular differentiation, neuroplasticity, neuroprotection and cognitive function in the brain. Recently, transcriptomic analysis of rat striatum showed that pridopidine treatment activates expression of the brain-derived neurotrophic factor (BDNF), dopamine receptor 1 (D1R), glucocorticoid receptor (GR), and the serine-threonine kinase protein kinase B (Akt)/phosphoinositide 3-kinase (PI3K) pathways, known to promote neuronal plasticity and survival and to be impaired in HD. Pridopidine was shown to enhance secretion of the neuroprotective BDNF in a neuroblastoma cell line, in a S1R-dependent manner (Geva 2016).

The potential of pridopidine to reduce motor complications of levodopa in PD was reported using the 6-OHDA-lesioned rat model (Ponten 2013). The data from that rat 6-OHDA study suggest that low doses of pridopidine, (correlate to human doses up to about 67.5 mg bid) may be efficacious against PD-LID.

Tedroff, 2004, reported an open label, uncontrolled, self-assessed, pilot study of once a day low dosepridopidine (20-100 mg once a day; average dose 57 mg/day) in seven advanced stage Parkinson's disease (PD) patients. Tedroff provides no guidance for treating LID in PD patients. Since that study was disclosed with no mention of what the "regular antiparkinsonian medication" is, no controlled study has been performed to objectively assess the effect of pridopidine for treating LID in PD patients.

Effective treatments for LID and other drug induced movement disorders (DIMD), including drug-induced dyskinesias, remain a significant unmet need.

SUMMARY OF THE INVENTION

The present invention is based at least in part on evidence from in vivo studies that high doses of pridopidine are efficacious in treating symptoms of drug induced dyskinesias, including PD-LID.

This evidence is especially surprising in view of the lack of efficacy of high doses of pridopidine in improving motor function in HD patients.

The present invention provides a method of treating LID in a subject with PD comprising administering to the subject an amount of pridopidine effective to treat the LID in the subject. The present invention also provides a method of treating LID in a subject with parkinsonism other than PD comprising administering to the subject an amount of pridopidine effective to treat the LID in the subject.

The present invention also provides a method for treating dyskinesia induced by a drug other than levodopa, for example an anti-depressant or an anti-psychotic comprising administering to the subject an amount of pridopidine effective to treat the dyskinesia in the subject.

The present invention additionally provides a method of treating a subject afflicted with a drug-induced movement disorder (DIMD). The invention further provides a method for treatment of a DIMD in a subject in need thereof comprising periodically administering to the subject an amount of pridopidine effective to treat the DIMD. The invention also provides pridopidine for use in treating drug-induced movement disorder (DIMD) in a subject in need thereof.

The invention also provides a method of treating drug-induced movement disorder (DIMD) in a subject in need thereof, comprising administering to the subject a pharmaceutically effective amount of pridopidine and one or more additional therapeutic agent.

In some embodiments, the DIMD comprises dyskinesia. In some embodiments the dyskinesia is levodopa-induced dyskinesia (LID). In some embodiments, the DIMD is induced by a drug selected from an antidepressant, an antipsychotic, an antiepileptic, an antimicrobial, an antiarrhythmic, a mood stabilizer, a gastrointestinal drug or any combination thereof. Certain selective serotonin reuptake inhibitors (SSRI) are known to induce DIMD (Gerber 1998, incorporated herein in its entirety by reference). In some embodiments, the DIMD is selected from parkinsonism, tardive dyskinesia, chorea, dystonia, tremor, akathisia, athetosis, myoclonus or tics.

The invention further provides a method of treating a subject afflicted with a side effect of levodopa treatment comprising administering to the subject an amount of pridopidine effective to treat the subject. The invention provides pridopidine for use in treating a side effect of levodopa treatment in a subject in need thereof. This invention further provides a method of treating a human subject afflicted with a levodopa induced dyskinesia comprising periodically administering to the subject an amount of levodopa and an amount of pridopidine or a salt thereof, wherein the amounts when taken together are effective to treat the human subject. Further provided is pridopidine in combination with levodopa for use in treating levodopa induced dyskinesia in a subject in need thereof. In some embodiments of the method and use, the subject is afflicted with parkinsonism. In some embodiments of the method and use, the subject is a patient afflicted with Parkinson's disease.

This invention also provides a pharmaceutically effective amount of a composition comprising pridopidine or a pharmaceutically acceptable salt thereof and one or more additional therapeutic agent for use in treating drug-induced movement disorder (DIMD) in a subject in need thereof.

This invention further provides a method of treating levodopa-induced dyskinesia (LID) in a subject in need thereof, comprising administering to the subject a pharmaceutically effective amount of a composition comprising pridopidine or a pharmaceutically acceptable salt thereof and one or more additional therapeutic agent.

This invention provides a method of treating levodopa-induced dyskinesia (LID) in a subject in need thereof, comprising a combination therapy of administering to the subject pridopidine or pharmaceutically acceptable salt thereof, and amantadine.

In one embodiment, the subject is afflicted with Parkinson's disease. In one embodiment, the subject is afflicted with parkinsonism other than Parkinson's disease.

The invention further provides a method of treating a subject at risk of developing a drug-induced movement disorder, including levodopa-induced dyskinesia, comprising administering to the subject an amount of pridopidine effective to delay the onset of LID or reduce the risk of developing LID.

The present invention further provides a method of treating a subject as risk of developing levodopa-induced dyskinesia (LID) comprising periodically administering to the subject an amount of a composition comprising pridopidine or a pharmaceutically acceptable salt thereof effective to delay the onset of LID or reduce the risk of developing LID and one or more additional therapeutic agent.

In embodiments of the method and use for treating LID in PD patients, or of the method and use of treating a subject at risk of developing LID, the amount of pridopidine administered is greater than 100 mg/day up to 400 mg/day. In certain embodiments, the amount of pridopidine administered is 112.5 mg/day, 125 mg/day, 135 mg/day, 150 mg/day, 175 mg/day, 180 mg/day, 200 mg/day, 225 mg/day, 250 mg/day, 300 mg/day, 350 mg/day, or 400 mg/day.

In embodiments of the method and use for treating LID, or of the method and use of treating a subject at risk of developing LID, the AUC0-inf 24 achieved is 12,000 h*ng/ml to 60,000 h*ng/ml, or 20,000 h*ng/ml-60,000 h*ng/ml, or 25,000 h*ng/ml-60,000 h*ng/ml or at least 29,000 h*ng/ml up to about 60,000 h*ng/ml.

This invention also provides a package comprising (a) a first pharmaceutical composition comprising an amount of levodopa and a pharmaceutically acceptable carrier; (b) a second pharmaceutical composition comprising an amount of pridopidine and a pharmaceutically acceptable carrier. In a further embodiment, the package also comprises (c) instructions for use of the first and second pharmaceutical compositions together to treat a human subject afflicted with LID or DIMD. In some embodiments the pridopidine is provided as pridopidine base. In some embodiments the pridopidine is provided as a pridopidine salt, e.g. pridopidine HCl.

This invention additionally provides use of an amount of levodopa and an amount of composition comprising pridopidine or a pharmaceutically acceptable salt thereof in the preparation of a combination for treating a human subject afflicted with a levodopa induced dyskinesia wherein the levodopa or pharmaceutically acceptable salt thereof and the pridopidine are administered simultaneously, consecutively or contemporaneously. This invention additionally provides use of an amount of amantadine, or levodopa and amantadine, and an amount of pridopidine in the preparation of a combination for treating a human subject afflicted with a levodopa induced dyskinesia wherein the levodopa, or levodopa and amantadine, and the pridopidine are administered simultaneously, consecutively or contemporaneously.

This invention also provides a pharmaceutical composition comprising an amount of levodopa for use in treating a subject afflicted with levodopa induced dyskinesia as an add-on therapy or in combination with a composition comprising pridopidine by periodically administering the pharmaceutical composition comprising levodopa and the pharmaceutical composition comprising pridopidine to the subject.

This invention also provides a pharmaceutical composition comprising an amount of pridopidine for use treating a subject afflicted with levodopa induced dyskinesia as an add-on therapy or in combination with levodopa and/or amantadine by periodically administering the pharmaceutical composition to the subject.

The present invention further provides a method of alleviating or reducing a symptom associated with the levodopa treatment in a subject in need thereof, comprising administering to the subject a pharmaceutically effective amount of pridopidine and one or more additional therapeutic agents. In one embodiment, the symptom is abnormal movements, myoclonic jerks, irregular movements of extremities, gait, facial grimacing, ataxia, inability to sustain motor act, hand movement or balance, choreiform peak dose dyskinesia, or dystonic peak dose dyskinesia. In one embodiment, the symptom is bad quality on-time evoked by levodopa.

In one embodiment, in the method of the invention, the one or more additional therapeutic agent is selected from the group consisting of Amantadine, Dipraglurant (ADX48621), Foliglurax, mesdopetam (IRL790), Eltoprazine, Buspirone, Levetiracetam, and Nuedexta (dextromethorphan/Quinidine), or a combination thereof.

In yet another embodiment of the methods, uses and compositions, the dyskinesia in a subject afflicted with PD is quantified by the Movement Disorder Society Unified Parkinson's Disease Rating Scale (MDS-UPDRS) score, wherein an increase in the MDS-UPDRS score represents progression of Parkinson's disease symptoms, and the increment of the increase in total UPDRS score over a period of time represents the rate of progression of Parkinson's disease symptoms (Goetz 2007, Goetz 2008a, the entire contents of which are hereby incorporated by reference). In some embodiments, the dyskinesia in a subject afflicted with PD is quantified using the PD Home Diary scale. In other embodiment of the methods, uses and compositions, the dyskinesia in a subject not afflicted with PD is quantified by, for example, the Unified Dyskinesia Rating Scale (UdysRS) or AIMS rating scale (Goetz 2008b, Ecdeu 1976, the entire contents of which are hereby incorporated by reference).

BRIEF DESCRIPTION OF THE FIGURES

FIGS. 1-3 show the effect of pridopidine in historic studies of Huntington's disease.

In FIG. 1A, at 26 weeks, patients receiving placebo show a ~1 point increase in TMS, indicating worsening, and patients on 45 mg bid show a ~2 points decrease compared to baseline, indicating an improvement which is significantly different from the placebo group (p=0.004). In FIG. 1B, low dose 45 mg bid group shows a significant improvement vs. placebo at 12 weeks (p=0.039).

FIG. 2: Bar graph showing low dose pridopidine (45 mg bid) but not high dose (112.5 mg bid) pridopidine improves motor function from baseline as measured by Total Motor Score (TMS) in early-stage HD Patients (baseline TFC≥11) at week 52 in the PRIDE-HD study. A decrease in TMS from baseline indicates improvement (table below the graph).

FIG. 3: bar graph showing the pridopidine low dose (45 mg bid) but not high dose (112.5 mg bid) improves Total Functional Capacity (TFC) in HD patients at week 52 in the PRIDE-HD study. The 45 mg bid group shows an increase in TFC score from baseline, indicating improvement compared to placebo (p=0.0032). The 112.5 does not show any beneficial effect vs. placebo group (table below the graph).

FIG. 4 demonstrates occupancy of pridopidine at the Sigma-1 (S1R) and Dopamine D2/D3 receptors in the human brain.

FIGS. 5-10 show the effect of pridopidine in combination with a high levodopa (L-DOPA) dose in a 1-methyl-4-phenyl-1,2,3,6-tetrahydropyridine (MPTP)-lesioned non-human primate (NHP) model with established motor complications resulting from L-DOPA administration in two studies. In FIGS. 5, 6 and 9 pridopidine at doses of 15, 20 and 30 mg/kg were evaluated. In FIGS. 7, 8 and 10 the pridopidine doses of 7 and 20 mg/kg were evaluated. The figures provide data showing that pridopidine reduces levodopa induced dyskinesia, including choreiform and dystonic dyskinesia evoked by high-dose levodopa without affecting the beneficial anti-parkinsonian effects of levodopa.

FIG. 12A presents change in levels of AIMS over 3 hours measured every 20 minutes at different doses of pridopidine 3 mg/kg, 15 mg/kg, 30 mg/kg and 60 mg/kg vs. vehicle. FIG. 12B presents the cumulated values of the results presented in FIG. 12A within the time period of 20-120 minutes. FIG. 12C presents net contraversive rotations (NCR) of the rats during 3 hours measured every 20 minutes at different doses of pridopidine 3 mg/kg, 15 mg/kg, 30 mg/kg and 60 mg/kg vs. vehicle. FIG. 12D presents the cumulated values of the results presented in FIG. 12C within the time period of 20-120 minutes. P-values are presented in the corresponding tables. The higher doses of pridopidine, 30 and 60 mg/kg, significantly reduce NCRs ~3 and ~6-fold, respectively (p<0.05).

FIG. 13A presents the Limb AIMS results. FIG. 13B presents the Axial AIMS results. FIG. 13C presents the Orolingual AIMS results.

FIG. 14A presents the Limb results. Pridopidine reduces limb AIMS in a dose-dependent manner, significantly at the 15 (p<0.05), 30 (p<0.01) and the 60 (p<0.005) mg/kg doses. FIG. 14B presents the Axial results. Pridopidine reduces axial AIMS in a dose-dependent manner, with the most significant effect observed at the high dose of 60 mg/kg (p<0.01). FIG. 14C presents the Orolingual results. Pridopidine reduces orolingual AIMS significantly at the high dose of 60 mg/kg dose (p<0.05).

FIG. 15A presents change in levels of AIMS during 3 hours measured every 20 minutes. The combination of pridopidine with amantadine shows synergistic effect on AIMS, the most pronounced at 10 mg/kg AMT. FIG. 15B bar graphs presenting cumulative AIMS levels during 20-120 min, of results presented in FIG. 15A. Both doses of AMT alone show mild, non-significant effects on L-DOPA-induced AIMS. However, in combination with pridopidine 15 mg/kg, both doses have a significant synergistic effect, reducing AIMS levels (p<0.05, pridopidine +5 mg/kg AMT; p<0.01 pridopidine +10 mg/kg AMT). FIG. 15C presents net contraversive rotations (NCRs) of the rats over 3 hours measured every 20 minutes. A synergistic effect is viewed with the combination of pridopidine and AMT, most pronounced with pridopidine and AMT 10 mg/kg. FIG. 15D presents a 20-120 min total AIMS accumulated during the time period of 20-120 minutes of results presented in FIG. 15C. The combination of pridopidine and AMT shows a greater trend towards diminishing of NCRs than either drug administered on its own. These data indicate that AMT and pridopidine have a synergistic effect in reducing dyskinesia in PD models.

DETAILED DESCRIPTION OF THE INVENTION

Figure 1A:
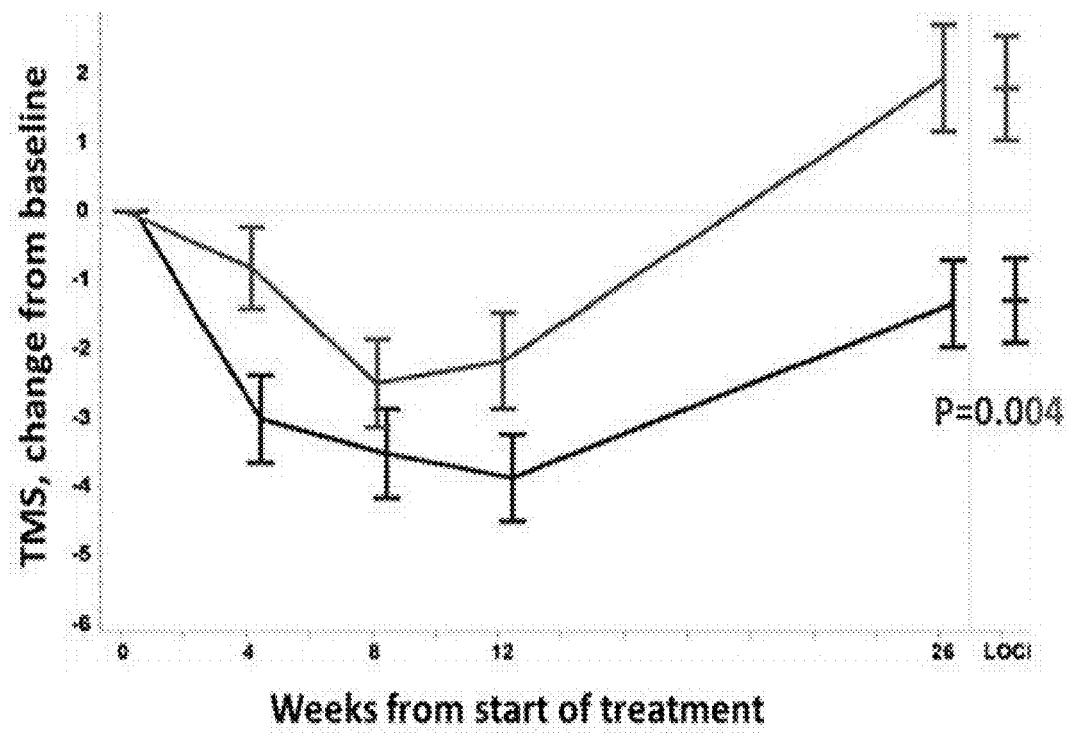
FIGS. 1A and 1B: Graphs showing the effect of low dose 45 mg bid pridopidine on Total Motor Score (TMS), full analysis set from MermaiHD (FIG. 1A) and HART (FIG. 1B) studies, respectively. In both graphs, the upper line (grey) shows results with placebo treatment, the lower line (black) shows results with low dose of 45 mg bid treatment. A decrease in TMS indicates improvement.

The present invention provides a method of treating a subject afflicted with a drug-induced movement disorder (DIMD) comprising periodically administering to the subject an amount of pridopidine effective to treat the subject. The invention further provides a method for the treatment of a DIMD comprising periodically administering to a subject in need thereof an amount of pridopidine effective to treat the DIMD. In some embodiments, the DIMD comprises dyskinesia.

In an embodiment, the dyskinesia is Levodopa-Induced Dyskinesia (LID).

The invention also provides a method of treating a subject afflicted with a side effect of levodopa treatment comprising administering to the subject an amount of pridopidine effective to treat the subject.

In another embodiment, treating comprises reducing a side effect of levodopa. In one embodiment, the side effect is dyskinesia.

In some embodiments, the subject is a patient afflicted with parkinsonism. In one embodiment, the subject is a Parkinson's disease patient. In another embodiment, the subject is an advanced stage Parkinson's disease patient. In a further embodiment, the subject is a patient afflicted with parkinsonism other than Parkinson's disease.

In one embodiment, the subject is concurrently being treated with levodopa.

In an embodiment, the amount of pridopidine and the levodopa are administered simultaneously. In another embodiment, the amount of pridopidine and the levodopa are co-formulated. In another embodiment, the amount of pridopidine and the levodopa are administered sequentially and in separate pharmaceutical formulations.

In one embodiment, the amount of pridopidine is effective to alleviate or reduce a symptom associated with the levodopa treatment. In some embodiments, the symptom is dyskinesia, abnormal movements, myoclonic jerks, irregular movements of extremities, gait, facial grimacing, ataxia, inability to sustain motor act, hand movement or balance. In another embodiment, the symptom is choreiform peak dose dyskinesia, or dystonic peak dose dyskinesia. In another embodiment, the symptom is bad quality on-time evoked by levodopa.

In an embodiment, the administration of pridopidine improves the symptom of the levodopa induced dyskinesia by at least 8%, by at least 10%, by at least 15%, by at least 20%, by at least 30% or by at least 50% as measured by the Unified Dyskinesia Rating Scale (UDysRS) (Unified Dyskinesia Rating Scale (UDysRS) 2008, the entire content of which is hereby incorporated by reference).

In one embodiment, the anti-parkinsonian effect of levodopa is not affected by the amount of pridopidine.

In an embodiment, the dyskinesia in the subject is assessed by one or more of the following rating scales: UDysRS, UPDRS or Abnormal Involuntary Movement Scale (AIMS) (Unified Dyskinesia Rating Scale (UDysRS) 2008; Unified Parkinson's Disease Rating Scale (UPDRS): status and recommendations. 2003, Ecdeu 1976, the entire content of each of which is hereby incorporated by reference). In another embodiment, the patient had a UDysRS score or UPDRS score of 10 or greater at baseline.

In some embodiments, the DIMD is induced by a drug selected from an antidepressant, an antipsychotic, an antiepileptic, an antimicrobial, an antiarrhythmic, a mood stabilizer, a gastrointestinal drug or any combination thereof. The DIMD may be selected from parkinsonism, tardive dyskinesia, chorea, dystonia, tremor, akathisia, athetosis, myoclonus or tics. In some embodiments the DIMD is parkinsonism. In some embodiments the DIMD is tardive dyskinesia. In some embodiments the DIMD is drug-induced dystonia. In some embodiments the DIMD is tremor. In some embodiments the DIMD is akathisia. In some embodiments the DIMD is athetosis. In some embodiments the DIMD is myoclonus. In some embodiments the DIMD is tics.

In one embodiment, the pridopidine is administered via oral administration. In another embodiment, the pridopidine is administered once or twice daily. In another embodiment, pridopidine is administered twice daily. In another embodiment, pridopidine is administered thrice daily. In another embodiment, the pridopidine is a pridopidine base. In another embodiment, the pridopidine is a pridopidine salt. In another embodiment, the pridopidine salt is provided as pridopidine hydrochloride (pridopidine HCl).

In embodiments of the method or use for treating LID in PD patients, the amount of pridopidine administered to a subject in need thereof is 112.5 mg/day, 125 mg/day, 135 mg/day, 150 mg/day, 180 mg/day, 200 mg/day, 225 mg/day, 250 mg/day, 300 mg/day, 350 mg/day, 375 mg/day or 400 mg/day. In another embodiment, the amount of pridopidine administered is from above 100 mg per day to 400 mg per day. In another embodiment, the amount of pridopidine administered is from above 200 mg per day to 350 mg per day. In another embodiment, the amount of pridopidine administered is from above 100 mg per day to 350 mg per day. In another embodiment, the amount of pridopidine administered is more than 100 mg per day to 400 mg per day. In another embodiment, the amount of pridopidine administered is 200 mg per day. In another embodiment, the amount of pridopidine administered is 300 mg per day. In another embodiment, the amount of pridopidine administered is 350 mg per day. In some embodiments, the amount of pridopidine is administered once daily. In some embodiments, the amount of pridopidine is administered twice daily. In some embodiments, the amount of pridopidine administered is 75 mg tid (thrice daily), 90 mg tid, 100 mg tid, or 125 mg tid. In another embodiment, the amount of pridopidine administered is 100 mg bid (twice daily), 125 mg bid, 150 mg bid, 175 mg bid, or 200 mg bid. In preferred embodiments, the pridopidine is administered as pridopidine HCl, twice daily.

In embodiments of the method or use for treating LID in PD patients, the amount of pridopidine administered is from about 75 mg bid to about 200 mg bid. In one embodiment, the amount of pridopidine administered is from about 80 mg bid to about 200 mg bid. In one embodiment, the amount of pridopidine administered is from about 90 mg bid to about 200 mg bid. In one embodiment, the amount of pridopidine administered is from about 100 mg bid to about 200 mg bid. In one embodiment, the amount of pridopidine administered is from about 125 mg bid to about 200 mg bid. In one embodiment, the amount of pridopidine administered is from about 150 mg bid to about 200 mg bid. In one embodiment, the amount of pridopidine administered is from about 175 mg bid to about 200 mg bid.

In one embodiment, the amount of pridopidine administered is from about 75 mg bid to about 175 mg bid. In one embodiment, the amount of pridopidine administered is from about 75 mg bid to about 150 mg bid. In one embodiment, the amount of pridopidine administered is from about 75 mg bid to about 125 mg bid. In one embodiment, the amount of pridopidine administered is from about 75 mg bid to about 100 mg bid.

In one embodiment, the amount of pridopidine administered is from about 90 mg bid to about 175 mg bid. In one embodiment, the amount of pridopidine administered is from about 100 mg bid to about 175 mg bid. In one embodiment, the amount of pridopidine administered is from about 100 mg bid to about 150 mg bid. In one embodiment, the amount of pridopidine administered is from about 125 mg bid to about 150 mg bid. In one embodiment, the amount of pridopidine administered is from about 125 mg bid to about 175 mg bid. In one embodiment, the amount of pridopidine administered is from about 150 mg bid to about 200 mg bid.

In one embodiment, the pridopidine is administered about 100 mg bid. In one embodiment, the pridopidine is administered about 125 mg bid. In one embodiment, the pridopidine is administered about 150 mg bid. In one embodiment, the pridopidine is administered about 175 mg bid. In one embodiment, the pridopidine is administered about 200 mg bid.

In one embodiment, the pridopidine is administered orally. In one embodiment, the pridopidine is administered about 100 mg bid orally. In one embodiment, the pridopidine is administered about 125 mg bid orally. In one embodiment, the pridopidine is administered about 150 mg bid orally. In one embodiment, the pridopidine is administered about 175 mg bid orally. In one embodiment, the pridopidine is administered about 200 mg bid orally In embodiments of the method or use for treating LID in PD patients, pridopidine is administered at a daily dose of about 200 mg given in the form of pridopidine salt. A person of skill in the art would know that when pridopidine is administered at a daily dose of 200 mg given in the form of pridopidine salt, the 200 mg of the daily dose refers to 200 mg of pridopidine in its neutral/base form. A skilled artisan would know how much pridopidine salt is needed to contain 200 mg of pridopidine. In embodiments of the method or use for treating LID in PD patients, pridopidine is administered at a daily dose of about 225 mg given in the form of pridopidine salt. In embodiments of the method or use for treating LID in PD patients, pridopidine is administered at a daily dose of about 250 mg given in the form of pridopidine salt. In embodiments of the method or use for treating LID in PD patients, pridopidine is administered at a daily dose of about 275 mg given in the form of pridopidine salt. In embodiments of the method or use for treating LID in PD patients, pridopidine is administered at a daily dose of 300 mg given in the form of pridopidine salt. In embodiments of the method or use for treating LID in PD patients, pridopidine is administered at a daily dose of about 325 mg given in the form of pridopidine salt. In embodiments of the method or use for treating LID in PD patients, pridopidine is administered at a daily dose of about 350 mg given in the form of pridopidine salt. In embodiments of the method or use for treating LID in PD patients, pridopidine is administered at a daily dose of about 375 mg given in the form of pridopidine salt. In embodiments of the method or use for treating LID in PD patients, pridopidine is administered at a daily dose of about 400 mg given in the form of pridopidine salt. In preferred embodiments of the method or use for treating LID in PD patients, the specified dosage of pridopidine is administered in two equal doses.

In preferred embodiments of the method or use for treating LID in PD patients, the AUC0-24 achieved is about 25,000 h*ng/ml to about 60,000 h*ng/ml.

In certain embodiments of the method of treating LID in PD patients, pridopidine is administered to a subject in need thereof in an amount to achieve an $AUC_{0-24}$ plasma level of greater than 12,000 h*ng/ml to about 60,000 h*ng/ml, 20,000 h*ng/ml to 60,000 h*ng/ml, 25,000 h*ng/ml to 60,000 h*ng/ml, 29,000 h*ng/ml to 60,000 h*ng/ml, 15,000 h*ng/ml to 45,000 h*ng/ml, 15,000 h*ng/ml to 40,000 h*ng/ml, 20,000 h*ng/ml to 55,000 h*ng/ml, 20,000 h*ng/ml to 50,000 h*ng/ml, 20,000 h*ng/ml to 45,000 h*ng/ml, 20,000 h*ng/ml to 40,000 h*ng/ml, 20,000 h*ng/ml to 35,000 h*ng/ml, 20,000 h*ng/ml to 30,000 h*ng/ml, or about 13,000 h*ng/ml, 14,000 h*ng/ml, 15,000 h*ng/ml, 16,000 h*ng/ml, 17,000 h*ng/ml, 18,000 h*ng/ml, 19,000 h*ng/ml, 20,000 h*ng/ml, 21,000 h*ng/ml, 22,000 h*ng/ml, 23,000 h*ng/ml, 24,000 h*ng/ml, 25,000 h*ng/ml, 26,000 h*ng/ml, 27,000 h*ng/ml, 28,000 h*ng/ml, 29,000 h*ng/ml, 30,000 h*ng/ml, 31,000 h*ng/ml, 32,000 h*ng/ml, 33,000 h*ng/ml, 34,000 h*ng/ml, 35,000 h*ng/ml, 36,000 h*ng/ml, 37,000 h*ng/ml, 38,000 h*ng/ml, 39,000 h*ng/ml, 40,000 h*ng/ml, 41,000 h*ng/ml, 42,000 h*ng/ml, 43,000 h*ng/ml, 44,000 h*ng/ml, 45,000 h*ng/ml, 46,000 h*ng/ml, 47,000 h*ng/ml, 48,000 h*ng/ml, 49,000 h*ng/ml, 50,000 h*ng/ml, 51,000 h*ng/ml, 52,000 h*ng/ml, 53,000 h*ng/ml, 54,000 h*ng/ml, 55,000 h*ng/ml, 56,000 h*ng/ml, 57,000 h*ng/ml, 58,000 h*ng/ml, 59,000 h*ng/ml, or 60,000 h*ng/ml, In some embodiments, pridopidine is administered to a subject in need thereof in an amount to achieve an $AUC_{0-24}$ plasma level of 25,000 h*ng/ml to 60,000 h*ng/ml, 29,000 h*ng/ml to 59,000 h*ng/ml, or 29,000 h*ng/ml to 50,000 h*ng/ml, or about 25,000 h*ng/ml, 26,000 h*ng/ml, 27,000 h*ng/ml, 28,000 h*ng/ml, 29,000 h*ng/ml, 44,000 h*ng/ml, 45,000 h*ng/ml, 46,000 h*ng/ml, 50,000 h*ng/ml, 51,000 h*ng/ml, or 52,000 h*ng/ml.

In some embodiments wherein the patient is suffering from LID, the method further comprises administering to the subject a therapeutically effective amount of levodopa.

In embodiments of the method or use for treating DIMD other than LID in PD patients, the amount of pridopidine administered to the subject is 22.5 mg/day, 45 mg, 67.5 mg/day, 75 mg/day, 90 mg/day, 100 mg/day, 112.5 mg/day, 125 mg/day, 135 mg/day, 150 mg/day, 180 mg per day, 225 mg/day, 250 mg/day, 270 mg/day, 275 mg/day, 300 mg/day, 350 mg/day, 360 mg/day, 375 mg/day or 400 mg/day.

In embodiments of the method or use for treating DIMD other than LID in PD patients, pridopidine is administered at a daily dose of 45 mg given in the form of pridopidine salt. In embodiments of the method or use for treating DIMD other than LID in PD patients, pridopidine is administered at a daily dose of 90 mg given in the form of pridopidine salt. In embodiments of the method or use for treating DIMD other than LID in PD patients, pridopidine is administered at a daily dose of 135 mg given in the form of pridopidine salt. In embodiments of the method or use for treating DIMD other than LID in PD patients, pridopidine is administered at a daily dose of 180 mg given in the form of pridopidine salt. In embodiments of the method or use for treating DIMD other than LID in PD patients, pridopidine is administered at a daily dose of 200 mg given in the form of pridopidine salt. In embodiments of the method or use for treating DIMD other than LID in PD patients, pridopidine is administered at a daily dose of 225 mg given in the form of pridopidine salt. In embodiments of the method or use for treating DIMD other than LID in PD patients, pridopidine is administered at a daily dose of 250 mg given in the form of pridopidine salt. In embodiments of the method or use for treating DIMD other than LID in PD patients, pridopidine is administered at a daily dose of 300 mg given in the form of pridopidine salt. In embodiments of the method or use for treating DIMD other than LID in PD patients, pridopidine is administered at a daily dose of 350 mg given in the form of pridopidine salt. In embodiments of the method or use for treating DIMD other than LID in PD patients, pridopidine is administered at a daily dose of 400 mg given in the form of pridopidine salt. In preferred embodiments of the method or use for treating DIMD other than LID in PD patients, the daily dose of pridopidine is administered in two equal doses.

In some embodiments, for example where the subject is afflicted with LID, the method further comprises administering to the subject a therapeutically effective amount of a second compound which is levodopa and/or amantadine. In some embodiments, the subject is administered pridopidine and levodopa. In some embodiments, the subject is administered pridopidine and amantadine. In some embodiments, the subject is administered pridopidine, levodopa and amantadine. In an embodiment, the pridopidine and the second compound (e.g. levodopa, amantadine or levodopa and amantadine) are administered in one unit. In another embodiment, the pridopidine and the second compound are administered in more than one unit.

In one embodiment, the second compound is amantadine. In another embodiment, the amount of amantadine is 10 mg-400 mg. In another embodiment, the amount of amantadine is 10 mg, 20 mg, 30 mg, 40 mg, 50 mg, 100 mg, 137 mg, 150 mg, 200 mg, 250 mg, 274 mg, 300 mg, 350 mg, or 400 mg per day in one dose or divided doses. In another embodiment, the amantadine is administered orally.

In an embodiment, the second compound is levodopa. In another embodiment, the amount of levodopa may be administered at a dose of, for example, 250 mg-6000 mg per day in one or more divided doses. In another embodiment, the amount of Levodopa is 250 mg, 300 mg, 500 mg, 750 mg, 1,000 mg, 1,500 mg, 2,000 mg, 2,500 mg, 3,000 mg, 3,500 mg, 4,000 mg, 4,500 mg, 5,000 mg, 5,500 mg, or 6,000 mg per day in one dose or divided doses.

In one embodiment, the amount of pridopidine and the amount of the second compound are administered simultaneously. In another embodiment, the administration of the second compound substantially precedes the administration of pridopidine. In another embodiment, the administration of pridopidine substantially precedes the administration of the second compound. In another embodiment, the subject is receiving amantadine therapy or levodopa therapy prior to initiating pridopidine therapy. In another embodiment, the subject is receiving amantadine therapy or levodopa therapy for at least 24 weeks, 28 weeks, 48 weeks, or 52 weeks prior to initiating pridopidine therapy. In another embodiment, the subject is receiving pridopidine therapy prior to initiating receiving amantadine therapy or levodopa therapy. In another embodiment, the subject is receiving pridopidine therapy for at least 24 weeks, 28 weeks, 48 weeks, or 52 weeks prior to initiating receiving amantadine therapy or levodopa therapy.

In one embodiment, each of the amount of the second compound when taken alone and the amount of pridopidine when taken alone is effective to treat the subject. In another embodiment, either the amount of the second compound when taken alone, the amount of pridopidine when taken alone, or each such amount when taken alone is not effective to treat the subject. In another embodiment, either the amount of the second compound when taken alone, the amount of pridopidine when taken alone, or each such amount when taken alone is less effective to treat the subject.

In one embodiment, the pridopidine is administered adjunctively to the second compound. In other embodiments, the second compound is administered adjunctively to the pridopidine.

In an embodiment, a loading dose of an amount different from the intended dose is administered for a period of time at the start of the periodic administration. In another embodiment, the loading dose is double the amount of the intended dose. In another embodiment, the loading dose is half the amount of the intended dose.

This invention provides a method of treating a human subject afflicted with a levodopa induced dyskinesia comprising periodically administering to the subject an amount of levodopa and an amount of pridopidine, wherein the amounts when taken together are effective to treat the human subject.

In one embodiment, the levodopa induced dyskinesia is a peak dose dyskinesia. In another embodiment, the levodopa induced dyskinesia is diphasic dyskinesia.

In one embodiment, the amount of levodopa and the amount of pridopidine when taken together are effective to reduce a symptom of the levodopa induced dyskinesia in the human subject. In another embodiment, the symptom is abnormal movements, myoclonic jerks, irregular movements of extremities, gait, facial grimacing, ataxia, inability to sustain motor act, hand movement or balance. In another embodiment, the subject is afflicted with PD and the subject's motor function is assessed using the total motor score (TMS) or the modified motor score (mMS) derived from the Unified Parkinson's Disease Rating Scale (UPDRS). In yet another embodiment, the patient had an mMS score of 10 or greater at baseline. In another embodiment, the subject is afflicted with parkinsonism other than PD parkinsonism and the subject's motor function is assessed by the UDysRS.

In an embodiment of the present invention, the administration of levodopa and pridopidine improves a symptom of the levodopa induced dyskinesia by at least 10%. In an embodiment of the present invention, the administration of levodopa and pridopidine improves a symptom of the levodopa induced dyskinesia by at least 20%. In another embodiment, the administration of levodopa and pridopidine improves a symptom of the levodopa induced dyskinesia by at least 30%. In another embodiment, the administration of levodopa and pridopidine improves a symptom of the levodopa induced dyskinesia by at least 50%. In another embodiment, the administration of levodopa and pridopidine improves a symptom of the levodopa induced dyskinesia by more than 100%. In another embodiment, the administration of levodopa and pridopidine improves a symptom of the levodopa induced dyskinesia by more than 300%.

In one embodiment, the human subject is receiving levodopa therapy prior to initiating pridopidine therapy. In another embodiment, the administration of levodopa and/or amantadine precedes the administration of pridopidine by at least one week, at least one month, at least three months, at least six months, or at least one year.

In one embodiment, the levodopa is administered via oral administration. In another embodiment, the levodopa is administered daily. In another embodiment, the levodopa is administered more often than once daily. In another embodiment, the levodopa is administered less often than once daily.

In one embodiment, the amount of levodopa administered is about 50 mg to 8,000 mg/day. In one embodiment, pridopidine is administered orally. In another embodiment, pridopidine is administered through a nasal, inhalation, subcutaneous, intravenous, intraperitoneal, intramuscular, intranasal, buccal, vaginal, rectal, intraocular, intrathecal, topical or intradermal route. In another embodiment, the pridopidine is administered daily. In another embodiment, the pridopidine is administered more often than once daily. In another embodiment, the administration of pridopidine is administered twice a day. In another embodiment, the pridopidine is administered less often than once daily.

In embodiments for the treatment of LID or for the use in the treatment of LID, the amount of pridopidine administered is greater than 100 to 1000 mg/day. In another embodiment, the amount of pridopidine administered is between 45-400 mg/day. In another embodiment, the amount of pridopidine administered is 112.5-400 mg/day. In another embodiment, the amount of pridopidine administered is 180-400 mg/day. In another embodiment, the amount of pridopidine administered is 150-400 mg/day. In another embodiment, the amount of pridopidine administered is 150-350 mg/day. In another embodiment, the amount of pridopidine administered is 180-400 mg/day. In another embodiment, the amount of pridopidine administered is 200-400 mg/day. In another embodiment, the amount of pridopidine administered is 180 mg/day. In another embodiment, the amount of pridopidine administered is 200 mg/day. In another embodiment, the amount of pridopidine administered is 225 mg/day. In another embodiment, the amount of pridopidine administered is 250 mg/day. In another embodiment, the amount of pridopidine administered is 300 mg/day. In another embodiment, the amount of pridopidine administered is 350 mg/day. In another embodiment, the amount of pridopidine administered is 400 mg/day.

In embodiments for the treatment of DIMD other than LID or for the use in the treatment of DIMD other than LID, the amount of pridopidine administered is 10-1,000 mg/day. In another embodiment, the amount of pridopidine administered is 45-400 mg/day. In another embodiment, the amount of pridopidine administered is 20-180 mg/day. In another embodiment, the amount of pridopidine administered is 50-180 mg/day. In another embodiment, the amount of pridopidine administered is 30-120 mg/day. In another embodiment, the amount of pridopidine administered is 150-1000 mg/day. In another embodiment, the amount of pridopidine administered is 180-1000 mg/day. In another embodiment, the amount of pridopidine administered is 150-400 mg/day. In another embodiment, the amount of pridopidine administered is 150-350 mg/day. In another embodiment, the amount of pridopidine administered is 180 mg/day. In another embodiment, the amount of pridopidine administered is 90 mg/day. In another embodiment, the amount of pridopidine administered is about 45 mg/day. In another embodiment, the amount of pridopidine administered is about 90 mg/day. In one embodiment, the method further comprises administration of a second compound which is an antidepressant, a psychotropic drug, an antipsychotic, amisulpride, haloperidol, olanzapine, risperidone, sulpiride, or tiapride. In an embodiment, the periodic administration of the second compound and pridopidine continues for at least 3 days. In another embodiment, the periodic administration of the second compound and pridopidine continues for more than 30 days. In another embodiment, the periodic administration of the second compound and pridopidine continues for more than 42 days. In another embodiment, the periodic administration of the second compound and pridopidine continues for 8 weeks or more. In another embodiment, the periodic administration of the second compound and pridopidine continues for at least 12 weeks. In another embodiment, the periodic administration of the second compound and pridopidine continues for at least 24 weeks. In another embodiment, the periodic administration of the second compound and pridopidine continues for more than 24 weeks. In yet another embodiment, the periodic administration of the second compound and pridopidine continues for 6 months, or 12 months or more.

This invention also provides a package comprising (a) a first pharmaceutical composition comprising an amount of levodopa and a pharmaceutically acceptable carrier; (b) a second pharmaceutical composition comprising an amount of pridopidine and a pharmaceutically acceptable carrier; and optionally (c) instructions for use of the first and second pharmaceutical compositions together to treat a human subject afflicted with levodopa induced dyskinesia. In some embodiments the pridopidine is pridopidine HCl or other pharmaceutically acceptable salt.

In one embodiment of the package, the first pharmaceutical composition, the second pharmaceutical composition, or both the first and the second pharmaceutical composition are in tablet form. In one embodiment, the first pharmaceutical composition, the second pharmaceutical composition, or both the first and the second pharmaceutical composition are in the form of an aerosol or inhalable powder. In another embodiment, the first pharmaceutical composition, the second pharmaceutical composition, or both the first and the second pharmaceutical composition are in liquid form. In another embodiment, the first pharmaceutical composition, the second pharmaceutical composition, or both the first and the second pharmaceutical composition are in solid form. In another embodiment, the first pharmaceutical composition, the second pharmaceutical composition, or both the first and the second pharmaceutical composition are in capsule form.

In an embodiment of the package, the amount of pridopidine in the second composition is 45 to 400 mg. In another embodiment, the amount of pridopidine in the second composition is 75-400 mg. In another embodiment, the amount of pridopidine in the second composition is 90-400 mg. In another embodiment, the amount of pridopidine in the second composition is 112.5-400 mg. In another embodiment, the amount of pridopidine in the second composition is 150-350 mg. In another embodiment, the amount of pridopidine in the second composition is 180-400 mg. In another embodiment, the amount of pridopidine in the second composition is 225-400 mg. In another embodiment, the amount of pridopidine in the second composition is 45 mg. In another embodiment, the amount of pridopidine in the second composition is 75 mg. In another embodiment, the amount of pridopidine in the second composition is about 90 mg. In another embodiment, the amount of pridopidine in the second composition is about 112.5 mg. In another embodiment, the amount of pridopidine in the second composition is 125 mg. In another embodiment, the amount of pridopidine in the second composition is 150 mg. In yet another embodiment, the amount of pridopidine in the second composition is 200 mg.

This invention also provides amantadine for use as an add-on therapy or in combination with pridopidine in treating a human subject afflicted with a neurodegenerative disorder.

This invention also provides a pharmaceutical composition comprising an amount of levodopa and/or amantadine and an amount of pridopidine. In one embodiment, the pharmaceutical composition is in the form of an aerosol or inhalable powder. In an embodiment, the pharmaceutical composition is in liquid form. In an embodiment, the pharmaceutical composition is in solid form. In an embodiment, the pharmaceutical composition is in capsule form. In an embodiment, the pharmaceutical composition is in tablet form.

In an embodiment of the present invention, the daily amount of pridopidine administered is greater than 100 mg and up to 400 mg. In another embodiment, the amount of pridopidine administered is 45-400 mg. In another embodiment, the amount of pridopidine administered is 110-400 mg. In another embodiment, the daily amount of pridopidine administered is 135-400 mg. In another embodiment, the daily amount of pridopidine administered is 250-400 mg. In another embodiment, the daily amount of pridopidine is 135-180 mg. In another embodiment, the daily amount of pridopidine administered is 180-350 mg. In another embodiment, the daily amount of pridopidine administered is 135 mg. In another embodiment, the daily amount of pridopidine administered is 180 mg. In another embodiment, the daily amount of pridopidine is 200 mg. In another embodiment, the daily amount of pridopidine administered is 225 mg. In another embodiment, the daily amount of pridopidine administered is 250 mg. In another embodiment, the daily amount of pridopidine administered is 300 mg. In another embodiment, the daily amount of pridopidine administered is 350 mg. In another embodiment, the daily amount of pridopidine administered is 400 mg. This invention also provides use of an amount of levodopa and/or amantadine and an amount of pridopidine in the preparation of a combination for treating a human subject afflicted with a levodopa induced dyskinesia wherein the levodopa and/or amantadine or pharmaceutically acceptable salt thereof and the pridopidine are administered simultaneously or contemporaneously.

This invention also provides a pharmaceutical composition comprising an amount of levodopa and/or amantadine for use in treating a subject afflicted with levodopa induced dyskinesia as an add-on therapy or in combination with pridopidine by periodically administering the pharmaceutical composition and the pridopidine to the subject.

This invention also provides a pharmaceutical composition comprising an amount of pridopidine for use treating a subject afflicted with levodopa induced dyskinesia as an add-on therapy or in combination with levodopa and/or amantadine by periodically administering the pharmaceutical composition and the levodopa and/or amantadine to the subject.

For the foregoing embodiments, each embodiment disclosed herein is contemplated as being applicable to each of the other disclosed embodiments. For instance, the elements recited in the method embodiments can be used in the pharmaceutical composition, package, and use embodiments described herein and vice versa.

All combinations, sub-combinations, and permutations of the various elements of the methods and uses described herein are envisaged and are within the scope of the invention.

Terms

As used herein, and unless stated otherwise, each of the following terms shall have the definition set forth below.

The articles "a", "an" and "the" are non-limiting. For example, "the method" includes the broadest definition of the meaning of the phrase, which can be more than one method.

As used herein, "effective" as in an amount effective to achieve an end means the quantity of a component that is sufficient to yield an indicated therapeutic response. For example, an amount effective to reduce a symptom of LID in a Parkinson's disease (PD) patient. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives. In a preferred embodiment, administration of an effective amount of a therapeutic compound is without undue adverse side effects (such as toxicity, irritation, or allergic response), commensurate with a reasonable benefit/risk ratio when used in the manner of this disclosure.

In some embodiments, compositions, uses and methods can be used to treat levodopa-induced dyskinesia (LID). LID can be present in PD patients who have been on levodopa for extended periods of time. 'Off-time' is when a PD patient's levodopa medication is no longer working well for them, and at least some of their Parkinson's symptoms have returned. The return of PD symptoms may include e.g.; slowness, stiffness or tremor; and sometimes total (akinesia) or partial (bradykinesia) immobility. 'On-time' is the time when a PD patient's levodopa medication is having benefit, and their Parkinson's symptoms are generally well controlled. Bad quality on-time is period of time when a PD patient's medication is not effective, for example, the patient is medicated and afflicted with disabling dyskinesia.

Three forms of dyskinesia have been classified on the basis of their course and presentation following treatment with levodopa: i) peak-dose dyskinesia (the most common form of LID; it correlates with high levodopa plasma level); ii) diphasic dyskinesia (occurs with rising and falling plasma levodopa levels; this form is usually dystonic or ballistic; does not respond to levodopa reduction); and iii) off-period dystonia (correlated to the akinesia that occurs before the full effect of levodopa sets in, when the plasma levels of levodopa are low) (Bargiotas 2013).

As used herein, to "treat" or "treating" encompasses reducing a symptom, inducing inhibition, regression, or stasis of the disorder and/or disease. As used herein, "inhibition" of disease progression or disease complication in a subject means preventing or reducing the disease progression and/or disease complication in the subject. In one embodiment "treating" or "treatment" refers to ameliorating at least one physical parameter, which may not be discernible by the subject. In yet another embodiment, "treating"" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Subject" includes humans. The terms "human," "patient," and "subject" are used interchangeably herein unless the context clearly indicates the contrary (e.g. in reference to healthy human volunteers). In an embodiment, the subject is a human adult. In an embodiment, the subject is a human adult having a mass of 70 kg.

"Administering to the subject" or "administering to the (human) patient" means the giving of, dispensing of, or application of medicines, drugs, or remedies to a subject/ patient to relieve, cure, or reduce the symptoms associated with a condition, e.g., a pathological condition. Oral administration is one way of administering the instant compounds to the subject. The administration can be periodic administration.

As used herein, "periodic administration" means repeated/recurrent administration separated by a period of time. The period of time between administrations is preferably consistent from time to time. Periodic administration can include administration, e.g., once daily, twice daily, three times daily, four times daily, weekly, twice weekly, three times weekly, four times a week and so on, etc.

As used herein, "adjunctively" means treatment with or administration of an additional compound, with a primary compound, for example for increasing the efficacy or safety of the primary compound or for facilitating its activity.

As used herein, "pridopidine" means pridopidine base or a pharmaceutically acceptable salt thereof, as well as its analogues or combination of pridopidine and its analogues or derivatives, for example deuterium-enriched version of pridopidine and salts. Examples of deuterium-enriched pridopidine and salts and their methods of preparation may be found in U.S. Application Publication Nos. 2013-0197031, 2016-0166559 and 2016-0095847, the entire content of each of which is hereby incorporated by reference. Examples of acid addition salts of pridopidine include, but is not limited to, the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. In certain embodiments, pridopidine is a pharmaceutically acceptable salt, such as the HCl salt or tartrate salt. Preferably, in any embodiments of the invention as described herein, the pridopidine is in the form of its hydrochloride salt.

In one embodiment, the pridopidine analogue's are represented by the following structures (compounds 1-7):

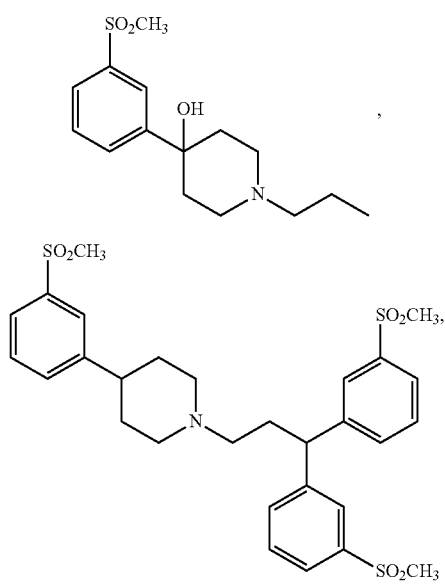

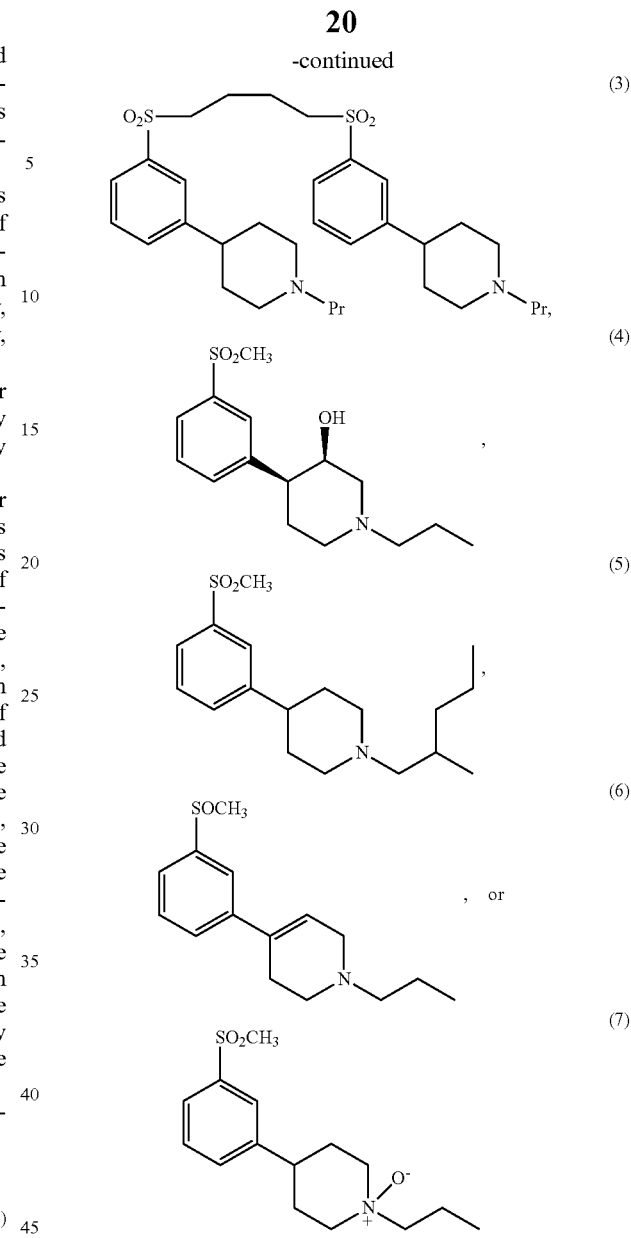

In some embodiments, the methods of this invention comprise administering a composition comprising pridopidine or pharmaceutically acceptable salt. In other embodiments, the composition comprises pridopidine or a pharmaceutically acceptable salt thereof and at least one of compounds 1-7 or a pharmaceutically acceptable salt thereof. In other embodiments, the composition comprises pridopidine or a pharmaceutically acceptable salt thereof and compound 1 or a pharmaceutically acceptable salt thereof. In other embodiments, the composition comprises pridopidine or a pharmaceutically acceptable salt thereof and compound 2 or a pharmaceutically acceptable salt thereof. In other embodiments, the composition comprises pridopidine or a pharmaceutically acceptable salt thereof and compound 3 or a pharmaceutically acceptable salt thereof. In other embodiments, the composition comprises pridopidine or a pharmaceutically acceptable salt thereof and compound 3 or a pharmaceutically acceptable salt thereof. In other embodiments, the composition comprises pridopidine or a pharmaceutically acceptable salt thereof and compound 5 or a pharmaceutically acceptable salt thereof. In other embodiments, the composition comprises pridopidine or a pharmaceutically acceptable salt thereof and compound 6 or a pharmaceutically acceptable salt thereof. In other embodiments, the composition comprises pridopidine or a pharmaceutically acceptable salt thereof and compound 7 or a pharmaceutically acceptable salt thereof. In other embodiments, the composition comprises pridopidine or a pharmaceutically acceptable salt thereof, compound 1 and compound 4 or pharmaceutically acceptable salt thereof. In other embodiments, at least one of compounds 1-7 is within the composition in a weight ratio of between 0.01 wt % to 1 wt % relative to the concentration of pridopidine.

Preferably, in any embodiments of the invention as described herein, the pridopidine is in the form of its hydrochloride salt. Pridopidine mixtures, compositions, the process for the manufacture thereof, the use thereof for treatment of various conditions, and the corresponding dosages and regimens are described in, e.g., PCT International Application Publication Nos. WO 2001/46145, WO 2011/107583, WO 2006/040155, U.S. Patent Application Publication No. 2011/0206782, U.S. Patent Application Publication No. 2010/0197712, the entire content of each of which is hereby incorporated by reference.

As used herein, an "amount" or "dose" of pridopidine as measured in milligrams refers to the milligrams of underivatized pridopidine base present in a preparation, dose or daily dose, regardless of the form of the preparation. A "dose of 200 mg pridopidine" means the amount of pridopidine in a preparation is sufficient to provide 200 mg of underivatized pridopidine base having a naturally occurring isotope distribution, regardless of the form of the preparation. Thus, when in the form of a salt, e.g. a pridopidine hydrochloride, the mass of the salt form necessary to provide a dose of 200 mg underivatized pridopidine base would be greater than 200 mg due to the presence of the additional salt ion. Similarly, when in the form of a deuterium-enriched derivative, the mass of the derivatized form necessary to provide a dose of 200 mg underivatized pridopidine base having a naturally occurring isotope distribution would be greater than 200 mg due to the presence of the additional deuterium. To exemplify, the factor for converting mass of pridopidine HCl to mass of pridopidine base is 0.885 (e.g. 1 mg pridopidine HCl×0.885 mg pridopidine base). Accordingly, 112.99 mg/day dose of pridopidine HCl is equivalent to a 100 mg dose of pridopidine base.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1; 0.2 . . . 0.9; and 1, 2 . . . 49 mg unit amounts are included as embodiments of this invention. By any range of time disclosed herein (i.e. weeks, months, or years), it is meant that all lengths of time of days and/or weeks within the range are specifically disclosed as part of the invention. Thus, for example, 3-6 months means that 3 months and 1 day, 3 months and 1 week, and 4 months are included as embodiments of the invention.

It is to be appreciated that certain features of the disclosure which are, for clarity, described herein in the context of separate embodiments, may also be provided in combination in a single embodiment. Conversely, various features of the disclosure that are, for brevity, described in the context of a single embodiment, may also be provided separately or in any subcombination. Further, reference to values stated in ranges includes each and every value within that range.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

As used herein, "levodopa" means L-3,4-dihydroxyphenylalanine (levodopa or L-DOPA) levodopa or a pharmaceutically acceptable salt thereof, as well as derivatives.

As used herein, the term "Cmax" refers to the maximum plasma, serum or blood concentration of a drug, following administration of the drug, e.g. pridopidine, or a pharmaceutically acceptable salt thereof.

As used herein, the term "Cmin" refers to the minimum plasma, serum or blood concentration of a drug, following administration of the drug, e.g. pridopidine, or a pharmaceutically acceptable salt thereof.

As used herein, the term "Tmax" refers to the time required to reach the maximal plasma, serum or blood concentration ("Cmax") of the drug, following administration of the drug, e.g. pridopidine, or a pharmaceutically acceptable salt thereof.

As used herein, the term "AUC" refers to the area under the plasma, serum or blood concentration versus time curve. "AUC0-t" refers to the area under the plasma, serum or blood concentration versus time curve wherein t (hours) is the last measured time point. "AUCinfinity" refers to the area under the plasma, serum or blood concentration versus time curve extrapolated to infinity. $AUC_{24-ss}$ refers to area under the concentration-time curve from 0 to 24 hours at steady state. Units are presented as h*ng/ml.

Pharmaceutically Acceptable Salts

The active compounds for use according to the invention may be provided in any form suitable for the intended administration. Suitable forms include pharmaceutically acceptable salts, and pre- or prodrug forms of the compound of the invention.

A "salt thereof" is a salt of the instant compound which has been modified by making acid or base salts of the compound. The term "pharmaceutically acceptable salt" in this respect, refers to the relatively non-toxic, inorganic and organic acid or base addition salts of compound of the present invention suitable for pharmaceutical use. Pharmaceutically acceptable salts may be formed by procedures well known and described in the art. One means of preparing such a salt is by treating a compound of the present invention with an inorganic base.

Examples of pharmaceutically acceptable addition salts include, without limitation, the non-toxic inorganic and organic acid addition salts such as the hydrochloride, the hydrobromide, the L-tartrate, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methane-sulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art. In certain embodiments, pridopidine is provided as a pharmaceutically acceptable salt, such as the HCl salt or tartrate salt. Preferably, in any embodiments of the invention as described herein, the pridopidine is in the form of its hydrochloride salt. "Deuterium-enriched" means that the abundance of deuterium at any relevant site of the compound is more than the abundance of deuterium naturally occurring at that site in an amount of the compound. The naturally occurring distribution of deuterium is about 0.0156%. Thus, in a "deuterium-enriched" compound, the abundance of deuterium at any of its relevant sites is more than 0.0156% and can range from more than 0.0156% to 100%, for example 50%, 60%, 70%, 75%, 8-%, 85%, 90%, 95%, 98% or 100%. Deuterium-enriched compounds may be obtained by exchanging hydrogen with deuterium or synthesizing the compound with deuterium-enriched starting materials. In some embodiments, the methods, uses, packages and kits include deuterated pridopidine.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection, for example infusion. The pharmaceutical composition of the invention can be manufactured by the skilled person by use of standard methods and conventional techniques appropriate to the desired formulation. When desired, compositions adapted to give sustained release of the active ingredient may be employed.

Add-On/Combination Therapy

In some embodiments, the present invention provides a pharmaceutically effective amount of pridopidine and one or more additional therapeutic agent for use in treating drug induced movement disorder (DIMD) in a subject in need thereof. In one embodiment, the one or more additional therapeutic agent is selected from the group consisting of Amantadine, Dipraglurant (ADX48621), Foliglurax, mesdopetam (IRL790), Eltoprazine, Buspirone, Levetiracetam, and Nuedexta (dextromethorphan/Quinidine), or a combination thereof. In another embodiment, the one or more additional therapeutic agent is Amantadine.

In one embodiment, the subject is concurrently being treated with levodopa.

In one embodiment, the pharmaceutically effective amount of pridopidine and one or more additional therapeutic agent are administered simultaneously with the levodopa.

In one embodiment, the pharmaceutically effective amount of pridopidine and one or more additional therapeutic agent and the levodopa are co-formulated. In another embodiment, the pharmaceutically effective amount of pridopidine and one or more additional therapeutic agent and the levodopa are administered sequentially and in separate pharmaceutical formulations.

In one embodiment, the pharmaceutically effective amount of pridopidine and one or more additional therapeutic agent are administered after the levodopa is administered for a period of time. In one embodiment, the period of time is from 10 min to 18 hours. In another embodiment, the period of time is 10 min, 20 min, 30 min, 45 mon, 1.0 hour, 2.0 hours, 6.0 hours, 12 hours or 18 hours.

In one embodiment, the levodopa is administered after the pridopidine and one or more additional therapeutic agent are administered for a period of time.

In one embodiment, the pharmaceutically effective amount of pridopidine and one or more additional therapeutic agent further alleviate or reduce a symptom associated with the levodopa treatment. In one embodiment, the symptom is abnormal movements, myoclonic jerks, irregular movements of extremities, gait, facial grimacing, ataxia, inability to sustain motor act, hand movement or balance, choreiform peak dose dyskinesia, or dystonic peak dose dyskinesia. In another embodiment, the symptom is bad quality on-time evoked by levodopa.

In one embodiment, the administration of pridopidine and one or more additional therapeutic agent improves the symptom of the levodopa induced dyskinesia by at least 10%, by at least 20%, by at least 30% or by at least 50% as measured by MDS-UPDRS or UDysRS.

In one embodiment, the pridopidine and one or more additional therapeutic agent are administered via oral administration.

In one embodiment, the pridopidine and one or more additional therapeutic agent are administered simultaneously or sequentially.

In one embodiment, the pridopidine and one or more additional therapeutic agent are administered once daily, twice daily, three times daily, four times daily, or less than once a day.

In one embodiment, the pridopidine is administered in a form of pridopidine salt. In one embodiment, the pridopidine salt is pridopidine hydrochloride.

In one embodiment, the pridopidine is administered at a dose of between 10 mg to 500 mg. In one embodiment, the pridopidine is administered at a dose of between 10 mg to 400 mg. In another embodiment, the pridopidine is administered at a dose of 10 mg once daily, twice daily, three times daily, or four times daily. In another embodiment, the pridopidine is administered at a dose of 22.5 mg once daily, twice daily, three times daily, or four times daily. In another embodiment, the pridopidine is administered at a dose of 45 mg once daily, twice daily, three times daily, or four times daily. In another embodiment, the pridopidine is administered at a dose of 67.5 mg once daily, twice daily, three times daily, or four times daily. In another embodiment, the pridopidine is administered at a dose of 75 mg once daily, twice daily, three times daily, or four times daily. In another embodiment, the pridopidine is administered at a dose of 100 mg once daily, twice daily, three times daily, or four times daily. In another embodiment, the pridopidine is administered at a dose of 112.5 mg once daily, twice daily, three times daily, or four times daily. In another embodiment, the pridopidine is administered at a dose of 120 mg once daily, twice daily, three times daily, or four times daily. In another embodiment, the pridopidine is administered at a dose of 150 mg once daily, twice daily, three times daily, or four times daily. In another embodiment, the pridopidine is administered at a dose of 175 mg once daily, twice daily, three times daily, or four times daily. In another embodiment, the pridopidine is administered at a daily dose of 150-400 mg/day. In another embodiment, the pridopidine is administered at a daily dose of 10-500 mg/day. In another embodiment, the pridopidine is administered at a daily dose of 10-400 mg/day.

In one embodiment, the pridopidine is administered at a daily dose of 200 mg given in the form of pridopidine HCl. In another embodiment, the pridopidine is administered at a daily dose of from 45 mg to 400 mg given in the form of pridopidine HCl.

In one embodiment, the pridopidine is administered in equal doses, twice daily.

In one embodiment, the pridopidine $AUC_{0-24}$ achieved is about 25,000 h*ng/ml to about 60,000 h*ng/ml.

In one embodiment, the one or more additional therapeutic agent comprises Amantadine at a dose of between 10 mg to 400 mg. In another embodiment, the amantadine is administered at a dose of 10, 20, 30, 40, 50, 100, 137, 150, 200, 250, 274, 300, 350, or 400 mg.

In one embodiment, the amantadine is administered once daily, twice daily, three times daily, or four times daily.

In one embodiment, the weight ratio between the pridopidine and the one or more additional therapeutic agent is from about 1:20 to about 20:1. In another embodiment, the weight ratio between the pridopidine and the one or more additional therapeutic agent is about 1:20, about 1:15, about 1:10, about 1:7.5, about 1:5.0, about 1:2.5, about 1:1, about 2.5:1, about 5:1, about 7.5:1, about 10:1, about 15:1 or about 20:1.

In some embodiments, the present invention provides a method of treating drug-induced movement disorder (DIMD) in a subject in need thereof, comprising administering to the subject a pharmaceutically effective amount of pridopidine and one or more additional therapeutic agent.

In one embodiment, the one or more additional therapeutic agent is selected from the group consisting of Amantadine, Dipraglurant (ADX48621), Foliglurax, mesdopetam (IRL790), Eltoprazine, Buspirone, Levetiracetam, and Nuedexta (dextromethorphan/Quinidine), or a combination thereof.

In some embodiments, the present invention provides a method of treating a subject at risk of developing levodopa-induced dyskinesia (LID) comprising periodically administering to the subject an amount of pridopidine effective to delay the onset of LID or reduce the risk of developing LID and one or more additional therapeutic agent. In one embodiment, the subject is receiving levodopa for treatment of Parkinson's disease. In another embodiment, the subject is receiving levodopa for treatment of parkinsonism other than Parkinson's disease.

When the invention comprises a combination of the active compound and an additional one, or more, therapeutic and/or prophylactic ingredients, the combination of the invention may be formulated for its simultaneous or contemporaneous administration, with at least a pharmaceutically acceptable carrier, additive, adjuvant or vehicle. This has the implication that the combination of two or three or more active compounds may be administered:

- as a combination that is part of the same medicament formulation, the two or more active compounds being then administered simultaneously, or
- as a combination of two or more units, each with one of the active substances giving rise to the possibility of simultaneous, or contemporaneous administration.

In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999).

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry 1999).

In one example, combined administration of glatiramer acetate (GA) and interferon (IFN) has been experimentally shown to abrogate the clinical effectiveness of either therapy. (Brod 2000). In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Therefore, the state of the art at the time of filing is that the effects of an add-on or combination therapy of two drugs, in particular levodopa and pridopidine or amantadine and pridopidine, could not have be predicted until the results of a formal combination study were available.

As used herein, "combination" means an assemblage of reagents for use in therapy either by simultaneous or contemporaneous administration. Simultaneous administration refers to administration of an admixture (whether a true mixture, a suspension, an emulsion or other physical combination) of pridopidine and a second compound (for example, levodopa, amantadine or combination of levodopa and amantadine). In this case, the combination may be the admixture or separate containers of pridopidine the second compound that are combined just prior to administration. Contemporaneous administration, or concomitant administration refers to the separate administration of pridopidine and the second compound at the same time, or at times sufficiently close together that a synergistic activity relative to the activity of either pridopidine alone the second compound alone is observed or in close enough temporal proximately to allow the individual therapeutic effects of each agent to overlap.

As used herein, "add-on" or "add-on therapy" means a therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine or pridopidine and amantadine therapy to a Parkinson's disease patient already receiving levodopa therapy. The FDA has recently approved extended release amantadine (Gocovri™; previously ADS-5102) for treating LID in patients with Parkinson's disease.

As used herein, "amantadine" means amantadine or a pharmaceutically acceptable salt thereof, as well as derivatives, for example deuterium-enriched version of amantadine and salts. Amantadine is descried in Prescribers' Digital Reference which is hereby incorporated by reference (for example, Amantadine PDR 2017). Amantadine as used herein refers to amantadine base or any pharmaceutically acceptable salt thereof.

In one example, an extended release formulation of amantadine may be administered to the subject in the evening and pridopidine may be given twice or three times during the day, for example morning and afternoon. In one example, immediate release formulations of amantadine are administered in the morning and afternoon and pridopidine is administered in the morning, afternoon and/or early evening. Optionally, levodopa is administered to the subject.

Parkinson's disease (PD) is a progressive disorder of the nervous system that affects movement. PD is the second most common progressive neurodegenerative disorder affecting older American adults and is predicted to increase in prevalence as the United States population ages. The disease is a result of pathophysiologic loss or degeneration of dopaminergic neurons in the substantia nigra (SN) of the midbrain and the development of neuronal Lewy Bodies. PD is characterized by both motor and non-motor symptoms. PD patients classically display rest tremor, rigidity, bradykinesia, and stooping posture, but can also exhibit neurobehavioral disorders (depression, anxiety), cognitive impairment (dementia), and autonomic dysfunction (e.g., orthostasis and hyperhidrosis). The underlying molecular pathogenesis involves multiple pathways and mechanisms: α-synuclein proteostasis, mitochondrial function, oxidative stress, calcium homeostasis, axonal transport and neuroinflammation. Dyskinesia refers to hyperkinetic movement disorders in which a variety of abnormal involuntary movements can manifest as single or multiple phenomenologies, which are typically present during wakefulness and cease during sleep.

Along with rigidity and bradykinesia, certain types of dyskinesia, e.g. tremor, can be a feature that is associated with PD and that differentiates PD from other disorders, where they are much less common. Dyskinesia and other features of PD are measured as part of the Unified Parkinson's Disease Rating Scale (UPDRS) (Goetz 2007; Movement Disorder Society Task Force 2003; the entire contents of which are hereby incorporated by reference).

The dopamine (DA) precursor levodopa (also known as L-DOPA) has been the most effective treatment for PD for over 40 years, however the response to this treatment changes with disease progression and most patients develop dyskinesias and motor fluctuations, resulting from levodopa, within a few years of therapy.

The symptoms of PD are most commonly treated with levodopa. However, use of levodopa is often complicated with dyskinesia that is caused by levodopa, mitigating its beneficial effects. The features of Levodopa-Induced Dyskinesia (LID) are different from those of PD dyskinesia and include chorea, dystonia, akathisia, athetosis and tics. Dyskinesia in PD can sometimes, in a general sense, refer to the movement disorder associated with PD. LID, on the other hand, is related to administration of levodopa and incorporates chorea, dystonia, akathisia, athetosis, tics, myoclonus. Akathisia and dystonia are not seen in PD patients not treated with levodopa. These specific dyskinetic features of LID are measured by the Unified Dyskinesia Rating Scale (UDysRS). The UDysRS, having both subjective and objective dyskinesia ratings, rate all aspects of LID including features such as chorea and dystonic movements (Goetz 2013, the entire contents of which are hereby incorporated by reference).

The mechanisms underlying development of LID involve interplay between progressive degeneration of neurons in the basal ganglia and chronic dopaminergic stimulation by levodopa treatment. Mechanisms underlying LID are not completely understood, however both pre- and postsynaptic disturbances of dopamine (DA) transmission are involved. Presynaptic factors contribute to generating fluctuating levels of levodopa and DA in the brain and include loss of Dopamine Transporters (DAT) and loss of physiological DA storage and release sites. Postsynaptic molecular mechanisms include changes in dopamine receptor trafficking, signaling and supersensitivity, structural and molecular changes in striatal neurons and altered activity in the basal ganglia. Non-dopaminergic modulatory systems such as the glutamatergic system, serotonergic neurons as well as other neuromodulators (Noradrenaline, acetylcholine, opioids and cannabinoids) also play a role in LID. Additional functional and structural changes involved in the pathogenesis of dyskinesia include modulation of vascular endothelial growth factor expression level by astrocytes and over activation of the adenosine A2A receptors. Changes in the extracellular levels of glutamate and altered levels of the glutamate transporter gene expression have been observed in basal ganglia structure of dyskinetic animals. Taken together, these functional alterations point towards a complex multi factorial mechanism behind the generation and expression of dyskinesia which could explain the difficulty of managing these motor complications (reviewed in Daneault 2013).

LID is the most common cause of medication-induced movement disorder. However, drug-induced movement disorders (DIMDs) can be elicited by several kinds of pharmaceutical agents which modulate dopamine neurotransmission as well as other neurotransmission in the central nervous system such as serotonin, adrenaline and acetylcholine. The major groups of drugs responsible for DIMDs include antidepressants, antipsychotics (neuroleptics), antiepileptics, antimicrobials, antiarrhythmics, mood stabilizers and gastrointestinal drugs among others. These movement disorders can include: Parkinsonism, Tardive dyskinesia, Chorea, Dystonia, Tremor, Akathisia, Myoclonus or Tics. The term "Parkinson's disease levodopa-induced dyskinesia;" "levodopa-induced dyskinesia," or "LID" refers to an abnormal muscular activity disorder that results from levodopa therapy, the disorder being characterized by either disordered or excessive movement (referred to as "hyperkinesia" or "dyskinesia"), slowness, or a lack of movement (referred to as "hypokinesia," "bradykinesia," or "akinesia"). LID includes any involuntary movement that results from levodopa therapy, such as chorea, ballism, dystonia, athetosis, tic, or myoclonus. The most common types of levodopa-induced dyskinesia are chorea and dystonia, which often coexist. (Johnston 2001). Based on their relationship with levodopa dosing, levodopa-induced dyskinesias are classified as peak-dose, diphasic, off state, on state, and yo yo dyskinesias. Peak-dose dyskinesias are the most common forms of LID and are related to peak plasma (and possibly high striatal) levels of levodopa. They involve the head, trunk, and limbs, and sometimes respiratory muscles. Dose reduction can ameliorate them, frequently at the cost of deterioration of parkinsonism. Peak-dose dyskinesias are usually choreiform, though in the later stages dystonia can superimpose. Diphasic dyskinesias develop when plasma levodopa levels are rising or falling, but not with the peak levels. They are also called D-I-D (dyskinesia-improvement-dyskinesia). D-I-D are commonly dystonic in nature, though chorea or mixed pattern may occur. They do not respond to levodopa dose reduction and may rather improve with high dose of levodopa. "Off" state dystonias occur when plasma levodopa levels are low (for example, in the morning). They are usually pure dystonia occurring as painful spasms in one foot. They respond to levodopa therapy. Rare forms of LID include "on" state dystonias (occurring during higher levels of levodopa) and yo-yo dyskinesia (completely unpredictable pattern).

Other Drug-Induced Movement Disorders (DIMD)

Drug-induced dystonia is a twisting movement or abnormal posture (or a combination thereof) may manifest as acute or tardive involuntary limb movements, facial grimacing, cervical dystonia, oculogyric crisis, rhythmic tongue protrusion, jaw opening or closing, spasmodic dysphonia, and, rarely, stridor and dyspnea.

Drug-induced tardive dyskinesia includes involuntary movements that resemble multiple movement disorders. The term tardive means "late" to indicate that the condition occurs sometime after drug exposure, and the terms dyskinesia and dystonia describe the types of movements involved. Although the pathophysiologic mechanism of TD is unknown, it is believed that prolonged administration of neuroleptics, which act by blocking dopamine receptors (e.g., amoxapine, chlorpromazine, fluphenazine, haloperidol, one notable exception being clozapine), results in hypersensitivity or up-regulation of dopamine receptors in the basal ganglia of the brain (see e.g., Jankelowitz 2013). Drugs that increase or enhance the dopamine response, especially indirect dopamine agonists, can aggravate the disorder and the use of such drugs in neuroleptic therapy is typically avoided. (Bezchibnyk-Butler & Remington, Can J. Psych. 39:74, 1994).

Drug-induced akathisia (restlessness and characteristic movements of the legs) is one of the most disagreeable extrapyramidal side effects often caused by use of antipsychotic and antidepressant drugs.

Drug-induced Tourette syndrome (TS) is a neurological disorder with repetitive, involuntary movements or vocalizations. These involuntary movements are known as tics. Some of the most common tics are eye blinking, among other eye movements and facial grimacing, shoulder shrugging, and head or shoulder jerking. Some of these can be combined with one another to make more complex tics. Some tics involve self-harm but only in a small percentage (10% to 15%) of individuals Non-limiting examples of drugs that can induce movement disorders (DIMD) include any one of (US trade name in parentheses): acetohenazine (Tindal), amoxapine (Asendin), chlorpromazine (Thorazine), fluphenazine (Permitil, Prolixin), haloperidol (Haldol), loxapine (Loxitane, Daxolin), mesoridazine (Serentil), metaclopramide (Reglan), molinndone (Lindone, Moban), perphanzine (Trilafrom, Triavil), piperacetazine (Quide), prochlorperzine (Compazine, Combid), promazine (Sparine), promethazine (Phenergan), thiethylperazine (Torecan), thioridazine (Mellaril), thiothixene (Navane), trifluoperazine (Stelazine), triflupromazine (Vesprin), and trimeprazine (Temaril).

As used herein, "effective" when referring to an amount of pridopidine (or pridopidine and a second compound) refers to the quantity of pridopidine (or the quantities of pridopidine and a second compound) that is sufficient to yield a desired therapeutic response.

In some embodiments, pridopidine is administered with acetophenazine (Tindal). In some embodiments, pridopidine is administered with amoxapine (Asendin). In some embodiments, pridopidine is administered with chlorpromazine (Thorazine). In some embodiments, pridopidine is administered with fluphenazine (Permitil, Prolixin). In some embodiments, pridopidine is administered with haloperidol (Haldol). In some embodiments, pridopidine is administered with loxapine (Loxitane, Daxolin). In some embodiments, pridopidine is administered with mesoridazine (Serentil). In some embodiments, pridopidine is administered with metaclopramide (Reglan). In some embodiments, pridopidine is administered with molinndone (Lindone, Moban). In some embodiments, pridopidine is administered with perphanzine (Trilafrom, Triavil). In some embodiments, pridopidine is administered with piperacetazine (Quide). In some embodiments, pridopidine is administered with prochlorperzine (Compazine, Combid). In some embodiments, pridopidine is administered with promazine (Sparine). In some embodiments, pridopidine is administered with promethazine (Phenergan). In some embodiments, pridopidine is administered with thiethylperazine (Torecan). In some embodiments, pridopidine is administered with thioridazine (Mellaril). In some embodiments, pridopidine is administered with thiothixene (Navane). In some embodiments, pridopidine is administered with trifluoperazine (Stelazine). In some embodiments, pridopidine is administered with triflupromazine (Vesprin). In some embodiments, pridopidine is administered with trimeprazine (Temaril).

Parkinson's Disease Rating Scales

Several rating scales have been developed to measure involuntary movements in subjects afflicted with movement disorders, including parkinsonism, and PD patients. For example, the Unified Dyskinesia Rating Scale (UDysRS) was developed to evaluate involuntary movements often associated with treated Parkinson's disease. (Unified Dyskinesia Rating Scale (UDysRS), 2008, the entire content of which is hereby incorporated by reference). The UDysRS measures the intensity of dyskinesias in different body areas, the degree of impairment caused by dyskinesias when patients perform tasks of daily living, and the patient's perception of disability from dyskinesias. There are two primary sections:

Historical [Part 1 (On-Dyskinesia) and Part 2 (Off-Dystonia)]

Objective [Part 3 (Impairment) and Part 4 (Disability)]

On-Dyskinesia refers to the choreic and dystonic movements described to the patient as "jerking or twisting movements that occur when your medicine is working."

Off-Dystonia is described to the patient as "spasms or cramps that can be painful and occur when Parkinson's disease medications are not taken or are not working".

The MDS-UPDRS, Movement Disorder Society-Sponsored revision of the Unified Parkinson's Disease Rating Scale is another example of a rating scale often used in evaluating a PD patient's symptoms pre and post treatment (Goetz, 2008a; the entire content of which is hereby incorporated by reference).

The Total Unified Parkinson's Disease Rating Scale (UPDRS) score represents the level or severity of Parkinson's disease symptoms. It is used for measuring the change from baseline in efficacy variables during the treatment. UPDRS consists of a four-part test. A total of 42 items are included in Parts I-IV. Each item in parts I-III receives a score ranging from 0 to 4 where 0 represents the absence of impairment and 4 represents the highest degree of impairment. The sum of Parts I-IV at each study visit provides a Total UPDRS score. Parts I, II and IV are historical information. Part I is designed to rate mentation, behavior and mood (items 1-4). Part II (items 5-17) relates to Activities of Daily Living and refers to speech, swallowing, handwriting and the like. Part III (items 18-31) is a motor examination at the time of a visit and relates to facial expressions, tremor, rigidity and the like. Part IV (Items 32-42) relates to complications of the therapy and include questions relating to the disability and pain of the dyskinesia, on-off periods and the like.

The following measures may be used to assess efficacy of pridopidine in treating DIMD: change in Abnormal Involuntary Movement Scale (AIMS) score (items 1 through 7) from baseline to end of long-term therapy (Week 54) as assessed by blinded central video rating; proportion of subjects who are a treatment success at the end of long-term therapy (Week 54), based on the Clinical Global Impression of Change (CGIC) (in which a treatment success is defined as Much or Very Much Improved); change in the modified Craniocervical Dystonia (CDQ-24) score from baseline of this study to the end of long-term therapy (Week 54); proportion of subjects who have a 50% or greater reduction in AIMS score from baseline of this study to the end of long term therapy (Week 54); proportion of subjects who are a treatment success at the end of long-term therapy (Week 54), based on the Patient Global Impression of Change (PGIC) (in which a treatment success is defined as Much or Very Much Improved); percent change in AIMS score from Baseline of this study to the end of long term therapy (Week 54); and based on the change in AIMS score from baseline of this study to the end of long-term therapy (Week 54), as assessed by blinded central video rating, the cumulative proportion of responders ranging from a 10% improvement from baseline to a 90% improvement from baseline in steps of 10 percentage points. The Hauser PD diary is a valuable tool to assess on/off time in PD patients (Hauser 2004), including ON time with dyskinesia.

Rating scales including UPDRS, AIMS and UDysRS are available, for example, through the International Parkinson and Movement Disorder Society globally and from persons skilled in the art of movement disorder.

For all studies, the patient and independent rater may be independently blinded or not blinded. In some embodiment, patient and rater are blinded.

A "symptom" associated with a levodopa induced dyskinesia includes any clinical or laboratory manifestation associated with the levodopa induced dyskinesia and is not limited to what the subject can feel or observe. For example, a symptom of LID includes, but is not limited to involuntary movement, such as chorea, ballism, dystonia, tic, or myoclonus. The subject may experience one or more of the symptoms. For example, chorea and dystonia often coexist. Other symptoms may become apparent including tics or stereotypy.

"Improvement of" or "improving" or "ameliorating" a symptom as used herein refers to a favorable change in the patient's symptom as compared to baseline or as compared to a control subject not receiving the treatment. As used herein, "substantially precedes administration" means that the administration of one agent precedes another agent; and the two agents are not administered simultaneously or contemporaneously.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1-2.5 mg/day" includes 0.1 mg/day, 0.2 mg/day, 0.3 mg/day, etc. up to 2.5 mg/day.

The following numbered clauses define various aspects and features of the present invention:

1. A method of treating a subject afflicted with a drug-induced movement disorder (DIMD) comprising periodically administering to the subject an amount of pridopidine effective to treat the subject.
2. The method of clause 1, wherein the DIMD comprises dyskinesia.
3. The method of clause 2, wherein the dyskinesia is levodopa-induced dyskinesia (LID).
4. A method of treating levodopa-induced dyskinesia (LID) in a subject in need thereof, comprising a combination therapy of administering to the subject pridopidine or pharmaceutically acceptable salt thereof, and amantadine.
5. The method of clause 3 or clause 4, wherein treating comprises reducing a side effect of levodopa.
6. The method of any one of clauses 1-5, wherein the subject is a Parkinson's disease patient.
7. The method of clause 6, wherein the subject is an advanced stage Parkinson's disease patient.
8. The method of any one of clauses 1-7, wherein the subject is afflicted with parkinsonism other than Parkinson's disease.
9. The method of any one of clauses 1-7, wherein the subject is concurrently being treated with levodopa.
10. The method of clause 9, wherein the amount of pridopidine and the levodopa are administered simultaneously or contemporaneously.
11. The method of clause 9, wherein the pridopidine, amantadine and the levodopa are administered sequentially or contemporaneously.
12. The method of clause 9, wherein the pridopidine and amantadine are administered after the levodopa is administered for a period of time.
13. The method of clause 12, wherein the period of time is from 10 min to 18 hours.
14. The method of clause 13, wherein the period of time is 10 min, 20 min, 30 min, 45 min, 1.0 hour, 2.0 hours, 6.0 hours, or 12 hours or 18 hours.
15. The method of clause 4, wherein the pridopidine and amantadine are administered sequentially or contemporaneously.
16. The method of clause 4, wherein the pridopidine and amantadine are co-formulated.
17. The method of clause 3, wherein the pridopidine and the amantadine are administered in a separate pharmaceutical formulation.
18. The method of clause 9, wherein the levodopa is administered after the pridopidine and amantadine are administered for a period of time.
19. The method of clause 9, wherein the amount of pridopidine and the levodopa are co-formulated.
20. The method of clause 9, wherein the amount of pridopidine and the levodopa are administered sequentially and in separate pharmaceutical formulations.
21. The method of clause 5, wherein the amount of pridopidine is effective to alleviate or reduce a symptom associated with the levodopa treatment.
22. The method of clause 21, wherein the symptom is abnormal movements, myoclonic jerks, irregular movements of extremities, gait, facial grimacing, ataxia, inability to sustain motor act, hand movement or balance.

23. The method of clause 21, wherein the symptom is choreiform peak dose dyskinesia, or dystonic peak dose dyskinesia.
24. The method of clause 21, wherein the symptom is bad quality on-time evoked by levodopa.
25. The method of clause 21-24, wherein the administration of pridopidine improves the symptom of the levodopa induced dyskinesia by at least 8%, 10%, 20%, by at least 30% or by at least 50%. The method of any one of clauses 1-24, wherein the anti-parkinsonian effect of levodopa is not affected by the amount of pridopidine.
26. The method of clause 1, wherein the DIMD is induced by a drug selected from an antidepressant, an antipsychotic, an antiepileptic, an antimicrobial, an antiarrhythmic, a mood stabilizer, a gastrointestinal drug or any combination thereof.
27. The method of clause 26, wherein the DIMD is selected from parkinsonism, tardive dyskinesia, chorea, dystonia, tremor, akathisia, athetosis, myoclonus or tics.
28. The method of clause 26, wherein the DIMD is Tardive dyskinesia.
29. The method of clause 26, wherein the DIMD is drug-induced dystonia.
30. The method of clause 1 or clause 2, wherein the dyskinesia in the subject is assessed by the UDysRS or UPDRS.
31. The method of clause 30, wherein the patient had a UDysRS score or UPDRS score of 10 or greater at baseline.
32. The method of any one of clauses 1-31 wherein the amount of pridopidine is administered via oral administration.
33. The method of any one of clauses 1-32, wherein the amount of pridopidine is administered once daily.
34. The method of any one of clauses 1-32, wherein the amount of pridopidine is administered twice daily or three times daily.
35. The method of any one of clauses 1-35, wherein the pridopidine is in form of base or in form of salt.
36. The method of clause 35, wherein the pridopidine salt is pridopidine hydrochloride.
37. The method clause 1-37, wherein the amount of pridopidine administered is greater than the equivalent of 100 mg pridopidine HCl per day.
38. The method of clause 37, wherein the amount of pridopidine administered is greater than 100 mg/day to 400 mg/day.
39. The method of any one of clauses 1-38, wherein the amount of pridopidine is between 150 mg/day to 400 mg/day.
40. The method of any one of clauses 1-38, wherein the amount of pridopidine is 135 mg/day, 180 mg/day, 225 mg/day, 300 mg/day, 350 mg/day, or 400 mg/day.
41. The method of any one of clauses 1-38, wherein the amount of pridopidine administered is from 135 mg per day to 225 mg per day.
42. The method of clause 38, wherein the amount of pridopidine administered is from 45 mg per day to 180 mg per day, from 135 mg per day to 400 mg per day or 150 mg per day to 300 mg per day.
43. The method of clause 38, wherein the amount of pridopidine administered is 22.5 mg, 45 mg, 67.5, mg, 90 mg, 100 mg, 112.5 mg, 125 mg, 135 mg, 150 mg, 180 mg per day, 225 mg/day, 250 mg/day, 270 mg/day, 275 mg/day, 300 mg/day, 350 mg/day, 360 mg/day, 375 mg/day or 400 mg/day.
44. The method of any one of clauses 1-43, wherein pridopidine or pharmaceutically acceptable salt thereof further comprises at least one of pridopidine's analog compounds 1-7:

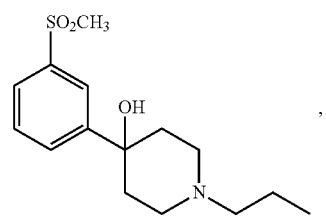
(1)

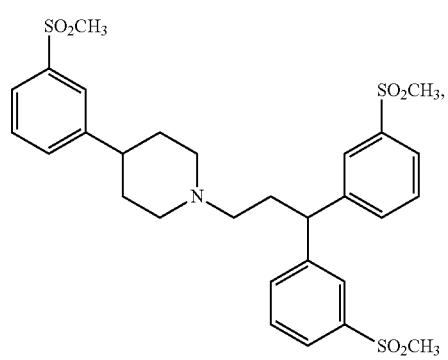
(2)

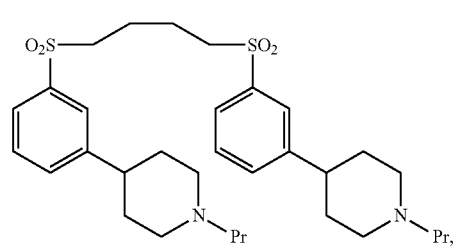
(3)

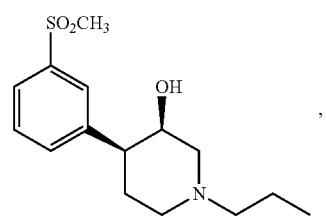
(4)

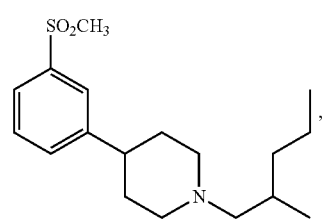
(5)

-continued

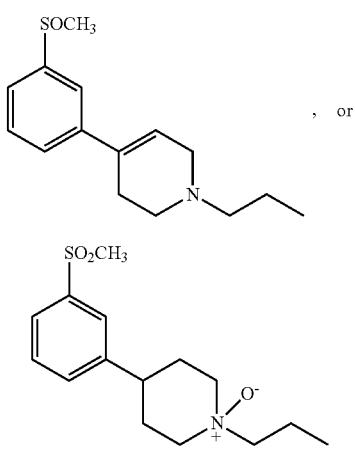

(6), or (7)

45. The method of clause 44, wherein the pridopidine and at least one of pridopidine's analog are co-formulated with pridopidine.

46. The method of any one of clauses 4-45, wherein the amount of amantadine is 10-400 mg.

47. The method of clause 46, wherein the amount of amantadine is 10, 50, 100, 137, 150, 200, 250, 274, 300, 350, or 400 mg.

48. The method of clause 45 or clause 47, wherein the amantadine is administered orally.

49. The method of any one of clauses 4-48, wherein the administration of pridopidine substantially precedes the administration of amantadine.

50. The method of any one of clauses 4-48, wherein the subject is receiving amantadine therapy prior to initiating pridopidine therapy.

51. The method of clause 50, wherein the subject is receiving amantadine therapy for at least 24 weeks, 28 weeks, 48 weeks, or 52 weeks prior to initiating pridopidine therapy.

52. The method of clause 49, wherein the subject is receiving pridopidine therapy prior to initiating receiving amantadine therapy.

53. The method of clause 52, wherein the subject is receiving pridopidine therapy for at least 24 weeks, 28 weeks, 48 weeks, or 52 weeks prior to initiating receiving amantadine therapy.

54. The method of any one of clauses 4, 46-54, wherein either the amount of amantadine when taken alone, the amount of pridopidine when taken alone, or each such amount when taken alone is less effective to treat the subject.

55. The method of any one of clauses 4, 46-54, wherein the pridopidine is administered adjunctively to amantadine.

56. The method of any one of clauses 4, 46-54, wherein the second compound is administered adjunctively to the pridopidine.

57. A pharmaceutical composition comprising an effective amount of pridopidine for use in treating a subject afflicted with a drug-induced movement disorder (DIMD).

58. Use of an amount of pridopidine for the manufacture of a medicament for use in treating a subject afflicted with a drug-induced movement disorder (DIMD).

59. A package comprising:
a) a pharmaceutical composition comprising an amount of pridopidine; and optionally
b) instructions for use of the pharmaceutical composition to treat a subject afflicted with a drug-induced movement disorder (DIMD).

60. A therapeutic package for dispensing to, or for use in dispensing to, a subject, which comprises:
c) one or more unit doses, each such unit dose comprising an amount of pridopidine thereof, wherein the amount of said pridopidine in said unit dose is effective, upon administration to said subject, to treat a drug-induced movement disorder (DIMD) in the subject, and
d) a finished pharmaceutical container therefor, said container containing said unit dose or unit doses, said container further containing or comprising labeling directing the use of said package in the treatment of a subject afflicted with the DIMD.

61. A package comprising:
e) a first pharmaceutical composition comprising an amount of pridopidine and a pharmaceutically acceptable carrier;
f) a second pharmaceutical composition comprising an amount of a second compound and a pharmaceutically acceptable carrier; and optionally
g) instructions for use of the first and second pharmaceutical compositions together to treat a subject afflicted with a drug-induced movement disorder (DIMD).

62. The package of clause 61, wherein the amount of the second compound and the amount of pridopidine are prepared to be administered simultaneously, contemporaneously or concomitantly.

63. A therapeutic package for dispensing to, or for use in dispensing to, a subject afflicted with a drug-induced movement disorder (DIMD), which comprises:
h) one or more unit doses, each such unit dose comprising:
i) an amount of pridopidine and
ii) an amount of a second compound;
wherein the respective amounts of said pridopidine and the second compound in said unit dose are effective, upon concomitant administration to said subject, to treat the subject, and
b) a finished pharmaceutical container therefor, said container containing said unit dose or unit doses, said container further containing or comprising labeling directing the use of said package in the treatment of said subject.

64. A pharmaceutical composition comprising an amount of pridopidine and an amount of amantadine.

65. The pharmaceutical composition of clause 64 for use in treating a subject afflicted with a drug-induced movement disorder (DIMD), wherein the pridopidine and the amantadine are prepared to be administered simultaneously, contemporaneously or concomitantly.

66. A pharmaceutical composition in unit dosage form, useful in treating a subject afflicted with a drug-induced movement disorder (DIMD), which comprises:
a) an amount of pridopidine;
b) an amount of second compound; wherein the respective amounts of amantadine and said pridopidine in said composition are effective, upon concomitant administration to said subject of one or more of said unit dosage forms of said composition, to treat the subject.

67. A pharmaceutical composition comprising an amount of pridopidine for use in treating a subject afflicted with a drug-induced movement disorder (DIMD) as an add-on therapy to second compound.

Throughout this application, various publications are referred to by first author and year of publication. Full citations for these publications are presented in a References section immediately before the claims. Disclosures of the documents and publications cited and those in the References section are hereby incorporated by reference in their entireties into this application in order to more fully describe the state of the art as of the date of the invention described herein.

This invention will be better understood by reference to the Experimental Details which follow, but those skilled in the art will readily appreciate that the specific experiments detailed are only illustrative of the invention as described more fully in the claims which follow thereafter.

EXAMPLES

Figure 1B:
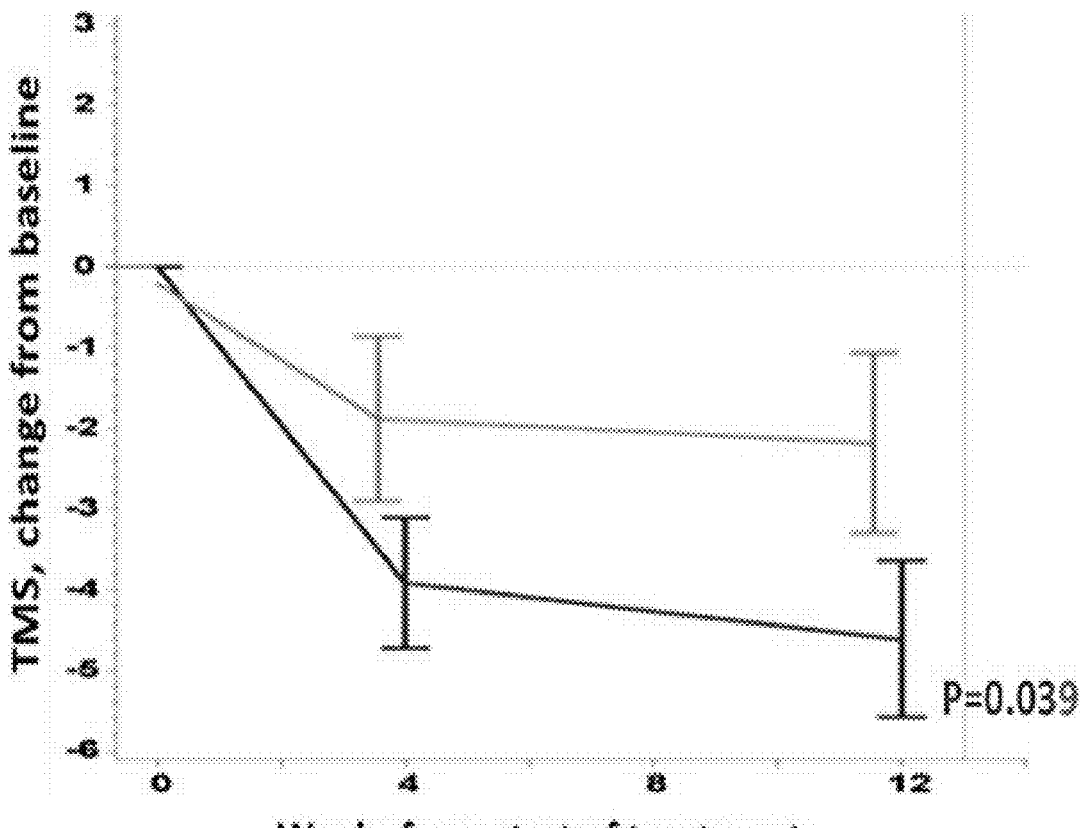

Example 1: Pridopidine Improves Motor Function and Functional Capacity in Huntington's Disease Patients at Low Doses but not at High Doses: Historic Results from MermaiHD, HART and PRIDE-HD Clinical Trials Pridopidine has been evaluated for the treatment of motor symptoms in patients with Huntington's Disease (HD), in three large scale clinical trials. The first two trials, MermaiHD and HART demonstrated that pridopidine, at a dose of 45 mg twice daily (bid) (90 mg/day) improves motor function in HD patients compared to placebo, as measured by the Unified Huntington Disease Rating Scale (UHDRS) Total Motor Score (TMS) (FIGS. 1A and 1B, MermaiHD and HART, respectively. Upper grey line placebo, lower black line 45 mg bid pridopidine)(de Yebenes 2011. Huntington Study Group HART investigators 2013; the entire contents of which are hereby incorporated by reference).

Based on these results, it was hypothesized that high doses of pridopidine would be more efficacious than low doses in alleviating HD motor symptoms. The PRIDE-HD study was conducted as an exploratory, phase 2 dose-ranging, 52-week, double-blind, placebo-controlled study, to evaluate efficacy and safety of pridopidine at doses higher than those used in prior studies, ranging from 45 mg to 112.5 mg bid and further disclosed in PCT Patent Publication No. WO2014/205229 and WO2018/039477. The primary outcome was pridopidine effect on motor function as assessed by the UHDRS-TMS, and exploratory endpoints including Total Functional Capacity (TFC), the most widely accepted tool for assessing disease stage were measured (Shoulson and Fahn 1979; Marder 2000). In the PRIDE-HD study, patients treated with 45 mg bid pridopidine showed a similar improvement in TMS as in HART and MermaiHD. However, none of the high doses of pridopidine (≥67.5 bid) showed improved efficacy compared to placebo or the 45 mg bid dose.

Figure 2:
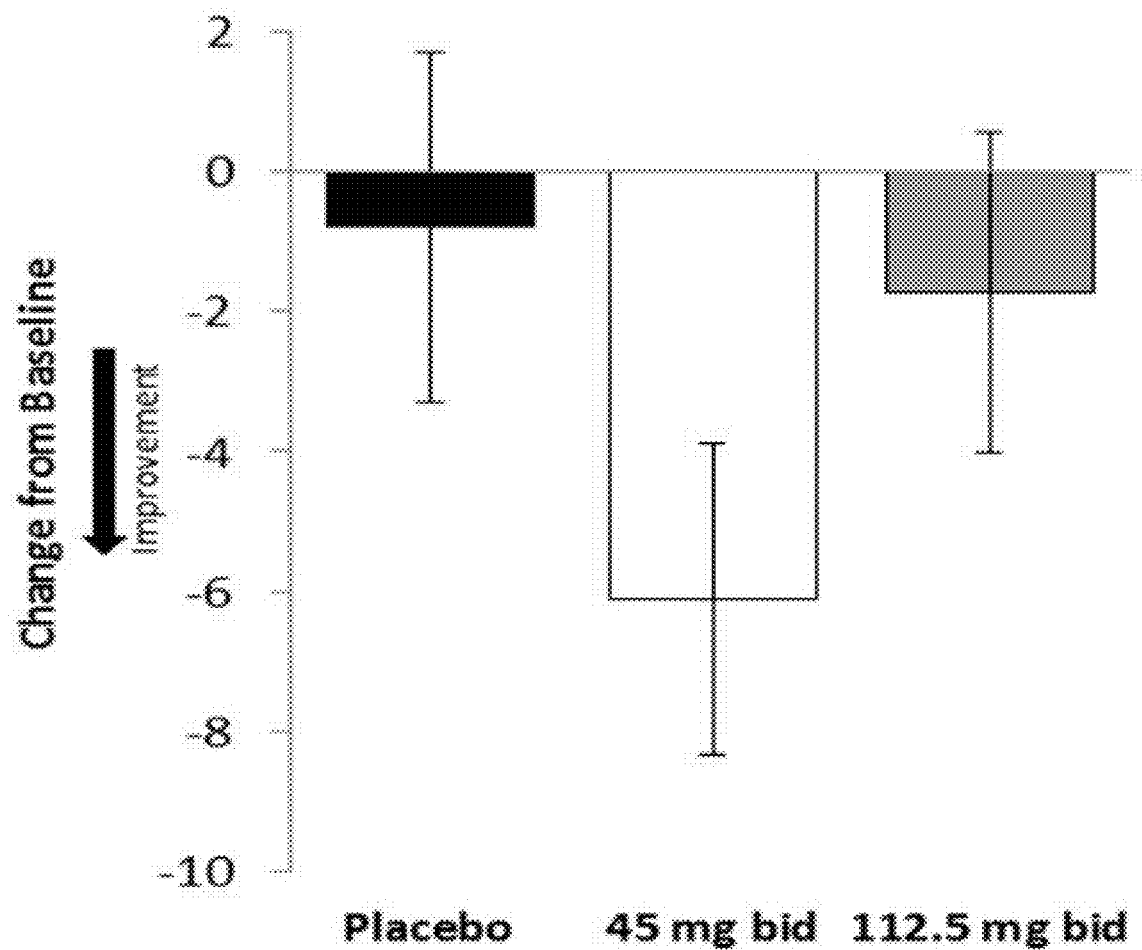

Post hoc analysis, at week 52, in early stage HD patients (HD stage 1, baseline TFC≥11) revealed there was a trend towards improvement in TMS change from baseline in the 45 mg bid dose treatment compared with placebo at weeks 26 or 52. However, no improvement with the high dose (112.5 mg bid) vs placebo was observed (FIG. 2, 52 weeks). A decrease in TMS (i.e. greater negative value) indicates improvement.

Figure 3:
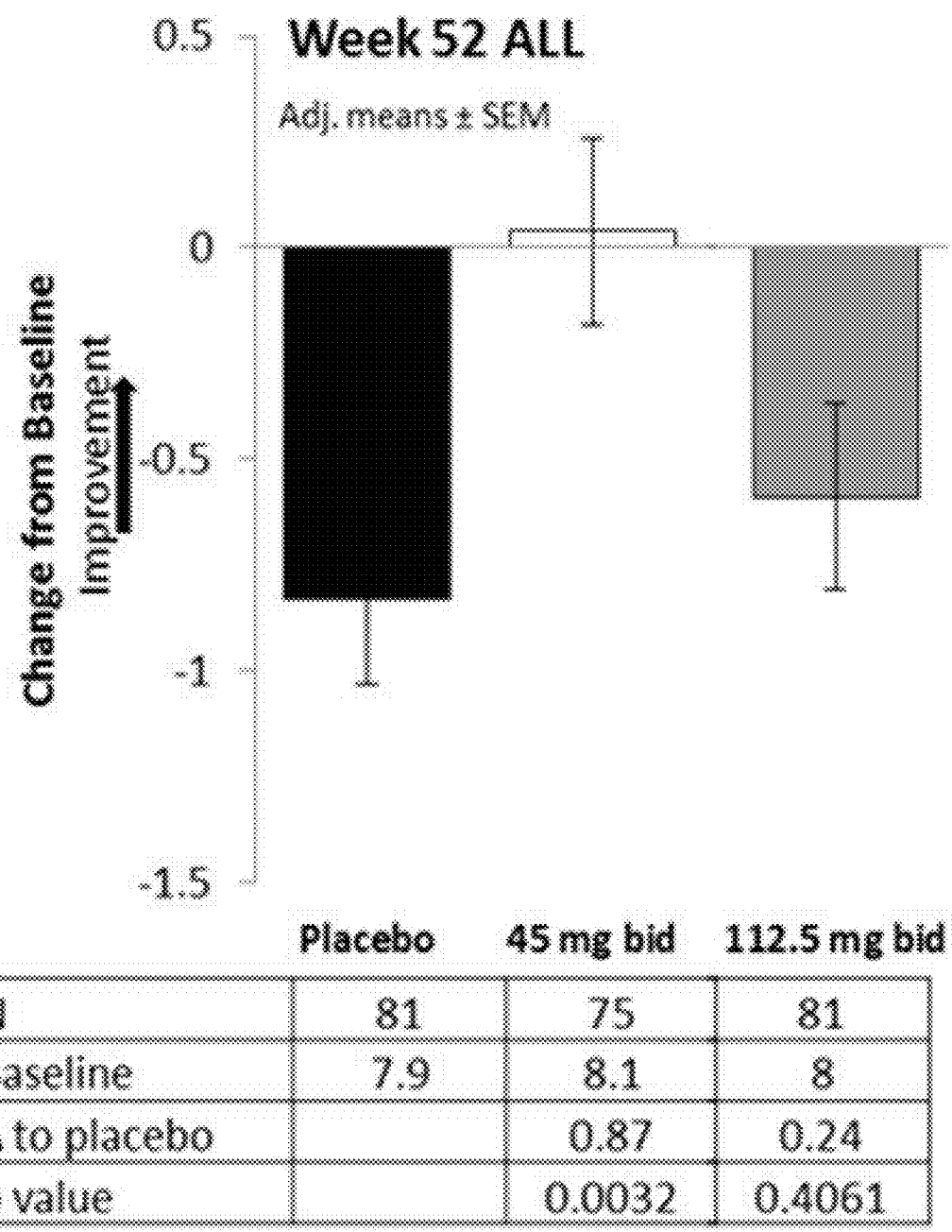

In the TFC pre-specified exploratory endpoint, patients receiving 45 mg bid pridopidine demonstrate significant maintenance or less decline in the TFC score compared with those receiving placebo at 52 weeks [difference: 0.87 (95% confidence interval: 0.29-1.45), nominal p=0.0032] (FIG. 3).

Again, the high dose (>90 mg bid) failed to show improvement in TFC decline. An increase in TFC (i.e. higher values) indicates improvement.

It was concluded from the PRIDE-HD study, that the effective dose is the low dose 45 mg bid and higher doses are less efficacious in motor and functional endpoints. The therapeutic effects in HD patients were lost at the high dose, which was similar to placebo.

Example 2: Pridopidine has Near Complete Occupancy of the Sigma-1 Receptor at Low Doses as Shown in Human Positron Emission Tomography (PET) Study Pridopidine occupancy of the Sigma-1 receptor (S1R) and the Dopamine-D2/D3 receptors in the human brain was assessed in a PET imaging study with healthy volunteers (HV) and Huntington's disease (HD) patients.

The radiotracer (S)-(−)-[18F]fluspidine (Brust 2014) was used to evaluate S1R target engagement and occupancy and [18F]fallypride (Slifstein 2010) tracer was used to evaluate D2/D3R engagement and occupancy. Occupancy was calculated as the difference between the pre- and post-treatment scans.

To minimize variability associated with the potential impact of circadian corticoid plasma level changes, individual scan and re-scan sessions were performed at comparable times of the day for all subjects.

The study consisted of a screening period of up to 8 weeks prior to first dosing of tracer, including a T1 three-dimensional magnetization-prepared rapid acquisition gradient echo (MPRAGE 3D) magnetic resonance imaging (MRI) scan (visit 1), a study period of up to 4 weeks (including visits 2 and 3), and a follow-up visit (visit 4). During the study period, the subjects underwent a baseline PET investigation (PET session 1) at visit 2, and subsequently a post-treatment PET investigation (PET session 2) following a single oral dose of pridopidine at visit 3. Each dose cohort comprised up to 4 subjects. Although every subject of each dose cohort was expected to receive the same dose, it was also possible to change the dose level within a cohort due to the adaptive design of the study.

Results:

The results of the imaging analysis show a S1R occupancy in healthy volunteers of almost 100% with 90 mg pridopidine, This is unexpectedly high S1R occupancy at even very low doses.

Figure 4A:
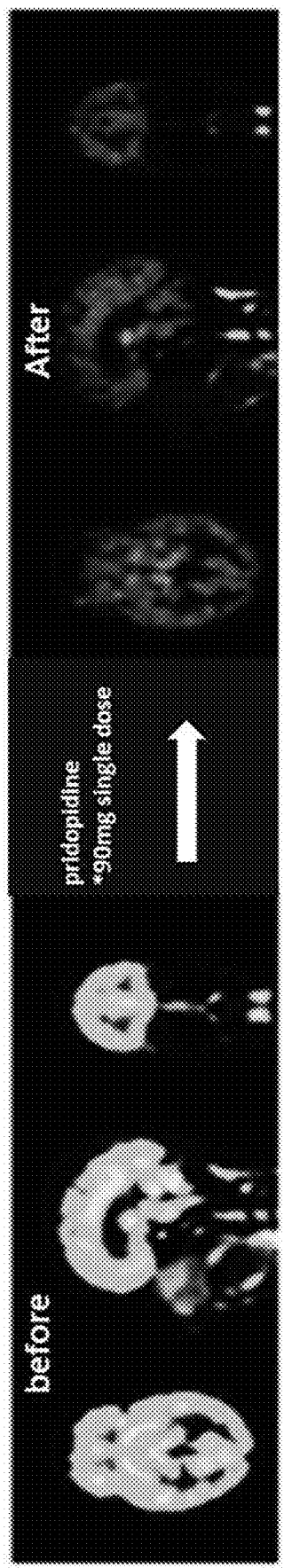
FIG. 4A: Reproduction of a PET scan showing levels of S1R occupancy by the radioligand 18F-fluspidine in the human brain before (left panel) and after (right panel) a single dose of 90 mg pridopidine, (exposure is equivalent to 45 mg bid at steady state). Pridopidine prevents the binding of fluspidine to the S1R, indicating a robust S1R occupancy by pridopidine (>90%).
Figure 4B:
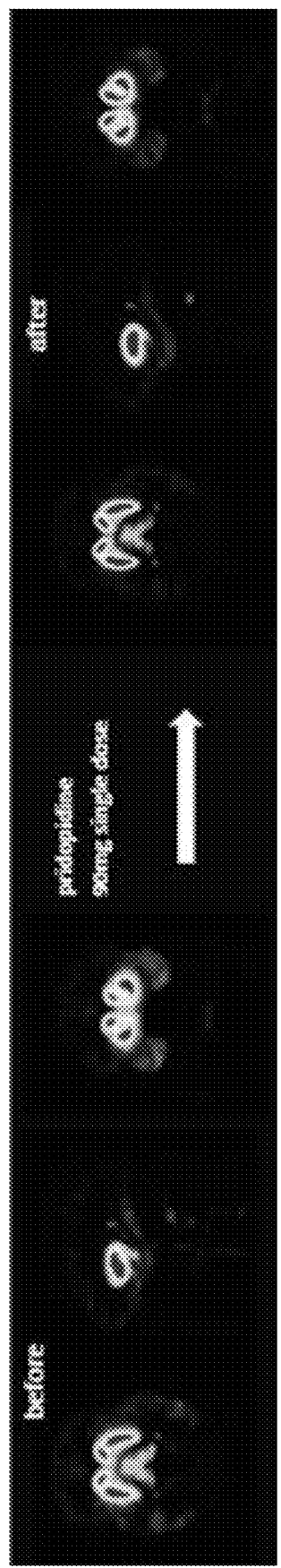
FIG. 4B: Reproduction of a PET scan showing levels of D2/D3R occupancy by the radioligand [18F]fallypride in the brain of healthy volunteers before (left panel) and after (right panel) a single dose of 90 mg pridopidine, (exposure is equivalent to 45 mg bid at steady state). Pridopidine has a negligible effect on the binding of [18F]fallypride to the S1R, indicating negligible D2/D3R occupancy by pridopidine (~3%).

FIG. 4A is a PET scan showing levels of S1R occupancy by pridopidine in the brain of healthy volunteers before (bright tissue, upper panel) and after (lower panel) a single dose of 90 mg pridopidine. This dose yields plasma exposure similar to the exposure at steady state with 45 mg bid, There was only minimal D2/D3R blockage (3%) at the 90 mg pridopidine dose, which was only borderline significant, and quantitatively negligible (FIG. 4B).

The beneficial effects of pridopidine in complex pathologies such as DIMD may be mediated by its interaction with both the S1Rs and the low affinity dopamine receptors (i.e. D2R).

Example 3: Pridopidine at High Doses but not Low Doses Improve Levodopa-Induced Dyskinesia without Reducing its Anti-Parkinsonism Effects in a Non-Human Primate (NHP) Model of Parkinson's Disease The potential of pridopidine to reduce motor complications of levodopa (L-DOPA) in PD was reported using the 6-OHDA-lesioned rat model (Ponten 2013). Pridopidine, dosed at 25 µmole/kg (corresponding to 8 mg/kg), decreased the L-DOPA-induced sensitization of contraversive-rotation while showing no decrease in the anti-parkinsonian benefit of L-DOPA. A pridopidine dose of 8 mg/kg in the rat results in $AUC_{0-24}$ levels of ~12000 h*ng/ml which correspond closely to the $AUC_{0-24}$ levels reached by the 67.5 mg bid dose in humans (12865 h*ng/ml). The human 67.5 mg bid dose is estimated, based on human PET data and PK profile of pridopidine, to exhibit effects similar to the 45 mg bid dose and to fully occupy the S1Rs with minimal occupancy of the dopamine receptors (DARs).

The pharmacokinetic (PK) profile and effects of pridopidine (7, 15, 20 and 30 mg/kg, PO) on parkinsonism, dyskinesia (chorea and dystonia) and quality of on-time (time in which parkinsonian symptoms are reduced), in combination with L-DOPA, were assessed in eight female 1-methyl-4-phenyl-1,2,3,6-tetrahydropyridine (MPTP)-lesioned macaques with stable and reproducible Levodopa-induced dyskinesia (LID). The correlation between plasma levels of pridopidine and S1R and D2/D3R receptor occupancies was assessed using both PK data and in-vitro/in-vivo binding data.

The study was conducted in two separate experiments. Study 1 evaluated the effects of pridopidine at 7 and 20 mg/kg in combination with L-DOPA on MPTP-lesioned macaques. In study 2, pridopidine at 15, 20 and 30 mg/kg in combination with L-DOPA was tested. In the first study (study 1) pridopidine was administered 1 hour before L-DOPA. In the second study (study 2) pridopidine was administered 2 hours before L-DOPA.

Material and Methods

Pridopidine hydrochloride (HCl) (4-[3-(Methylsulfonyl) phenyl]-1-propylpiperidine hydrochloride), MW 317.87 g/mol, highly soluble in water was obtained. For in-vivo PK and behavioral studies, pridopidine was formulated in sterile water with no correction made for the hydrochloride salt. Pridopidine was administered at a dose-volume of 1 ml/kg body weight.

In vitro binding: In vitro binding studies were performed at Eurofins Panlabs Taiwan, Ltd to evaluate IC50/Ki values for affinity of pridopidine to sites including σ1, σ2, adrenergic α2C, α2A, dopamine D3, dopamine D2, serotoninergic 5-HT1A, 5-HT2A, 5-HT7, histamine H3, muscarinic M2, NMDA, 5-HT6 and tachykinin NK1 receptors along with the dopamine transporter (DAT), norepinephrine transporter (NET) and serotonin transporter (SERT). The specific ligand binding to the receptors was defined as the difference between the total binding and the nonspecific binding determined in the presence of an excess of unlabeled ligand. IC50 values were determined by a non-linear, least squares regression analysis using MathIQ™ (ID Business Solutions Ltd., UK). Inhibition constants (Ki) values were calculated using the equation of Cheng and Prusoff using the observed IC50 of the tested compound, the concentration of radio ligand employed in the assay, and the historical values for the KD of the ligand (obtained experimentally at Eurofins Panlabs, Inc.). Hill coefficient (nH), defining the slope of the competitive binding curve, was calculated using MathIQ™. Hill coefficients significantly different than 1.0, may suggest that the binding displacement does not follow the laws of mass action with a single binding site.

Pharmacokinetic Profiling of Pridopidine in the Macaque

Blood sampling: On days of treatment, administration and plasma sampling, macaques were transferred from their home cages and seated in individual primate chairs. Four doses of pridopidine (7, 15, 20 and 30 mg/kg, N=8 per dose), were administered via oral gavage and nine blood samples for drug level analysis collected at 10 minutes prior to drug administration (t=−10 min) and then 10 and 30 min, 1, 2, 4, 6, 8 and 24 h post drug administration. All eight animals received each of the four treatments according to a non-randomized ascending dose design, each separated by a period of one-week. Plasma from blood samples was analyzed for pridopidine via LC/MS/MS.

Bioanalysis of pridopidine in macaque plasma: Pridopidine and its internal standard, 4-(3-methylsulfonyl)phenyl)-1-(propyld7)-piperidin-1-ium chloride, were extracted from EDTA plasma by liquid-liquid extraction into acetonitrile as follows: An aliquot of 20 µl of plasma was added to 80 µl of acetonitrile containing 1-10 ng/ml of the internal standard (IS). After centrifuging at 13000 rpm for 8 min, 70 µl of supernatant was isolated and added to 70 µl of sterile water. Finally, an aliquot of 1-10 µl of the mixture was injected into the LC-MS/MS system. For all bioanalytical work 4-(3-methylsulfonyl)phenyl)-1-(propyld7)-piperidin-1-ium chloride was used as the internal standard. In brief, LC-MS/MS analyses were performed on a Shimadzu LC-10AD pump equipped with a CTC-HTS auto-sampler (Zwingen, Switzerland) and a column oven. The MS/MS system was an MDS Sciex API-4000 mass spectrometer with an electrospray ionization-probe (Toronto, Canada). Chromatographic separation of the analytes was achieved on an Agilent Zorbax SB-C18 column. The linearity was from 2 ng/ml to 1000 ng/ml with LLOQ of 2 ng/ml. Accuracy values for pridopidine was lower than 15% for all calibration curves and for >75% of each QC sample sets. All PK parameters were calculated per individual animal according to nominal time, that is, within ±5% from schedule time-point by non-compartmental modelling for extravascular administration using WinNonlin 6.3. Below the Limit of Quantification (BLQ) value at time 0 or at a sampling time before the first quantifiable concentration, were treated as zero. BLQ values occurring at the end of the profile were treated as missing. Terminal elimination half-life ($t_{1/2}$) was calculated as $\ln(2)/\lambda z$. The maximum observed plasma concentration ($C_{max}$) and time to reach $C_{max}$ ($t_{max}$) were obtained directly from the concentration-time data. Area under the plasma concentration-versus-time curve from time 0 to 24 h post dose ($AUC_{0-24}$) was calculated by means of linear trapezoidal linear log interpolation regression analysis.

The pharmacokinetic profile of pridopidine was also characterized in plasma samples collected at multiple time-points up to 24 h after oral administration. These and other PK data across rodent and primate species were used to assess the relationship between plasma pridopidine levels and central S1R/D2/3R receptor occupancy.

Behavioral Assessment in the MPTP-Lesioned Macaques

Animals: Eight cynomolgus monkeys (*Macaca fascicularis*, 8-14 years of age, 3.0-4.8 kg, Suzhou Xishan-Zhongke Laboratory Animal Company, PRC) were used in this study. Fresh fruit, primate pellets and water were available ad libitum other than at times of overnight fasting (from 5 pm) prior to days of behavioral assessment. The housing rooms were subject to a 12-hour light-dark cycle (lights on 7 a.m.), 20-25° C. in a room containing only animals of the same sex.

MPTP administration and development of motor complications: Animals received once-daily subcutaneous injection of MPTP (0.2 mg/kg in 0.9% sterile-saline, Sigma-Aldrich, Oakville, ON, Canada) for 8-30 days. A parkinsonian syndrome was then allowed to develop over at least a 90-day period, during which time additional MPTP administrations were given as necessary, until animals reached moderate to marked levels of disability. Average cumulative MPTP dose was 33.3 mg. MPTP lesions were allowed to stabilize for a minimum of a further 60-day prior to commencing induction of L-DOPA-induced motor complications. LID, including both choreiform and dystonic dyskinesia, were evoked by chronic L-DOPA treatment (25 mg/kg, Madopar™, Roche, L-DOPA: benserazide, ratio 4:1) for at least 4-months. During this same period animals were acclimatized to the experimental setting, trained to provide blood samples (while restrained in chair) and to receive administration of treatment by oral, intravenous or subcutaneous routes.

L-DOPA dose-finding: Dose-finding observations were conducted to identify a dose of L-DOPA (LDh) intended to produce optimal anti-parkinsonian actions but which was compromised by disabling dyskinesia (range 30-35 mg/kg, mean 32.1 mg/kg). The response to this dose of L-DOPA was assessed to ensure stability and reproducibility within each animal on successive L-DOPA administrations.

Treatments: The assessment of the anti-dyskinetic potential of pridopidine was undertaken in two independent experiments, both of which utilized acute challenge randomized designs. In study 1, L-DOPA (PO) was assessed alone or in combination with two doses of pridopidine (7 and 20 mg/kg, PO). In study 2, L-DOPA (PO) was assessed alone or in combination with three doses of pridopidine (15, 20 and 30 mg/kg, PO). For both studies, on the day before behavioral observations, food was removed overnight, from 5 p.m. On days of behavioral assessment, treatments were administered to the animals in their home cages. Animals were then transferred to an observation cage for behavioral assessment. Based on the outcome of the PK arms it was decided that vehicle/pridopidine would be given 60 min (study 1) or 120 min (study 2) prior to vehicle/L-DOPA, relative to one another and to start of behavioral observations. The effects of treatments on parkinsonian disability, dyskinesia, duration and quality of anti-parkinsonian benefit (on-time) and activity were assessed and analyzed for a period of 6 hours (h).

Assessment of parkinsonian disability, dyskinesia (chorea and dystonia) and activity: Animals were transferred to individual observation cages (1.5×1.0×1.1 m) and their behavior recorded on HD-video. Rating scales for parkinsonism and dyskinesia adapted from their clinical counterparts (UPDRS pt. III and UDysRS respectively) were used to assess recordings via post-hoc analysis by a movement disorders neurologist blinded to treatment. A measure of total parkinsonian disability as described previously (Johnston 2013) was derived by adding scores for range of movement (score 0-4), bradykinesia (0-3), posture (0-2) and alertness (0-1). Dyskinesia, representative of the maximum of either chorea or dystonia was scored as 0—absent, 1—mild, 2—moderate, 3—marked or 4—severe. Parkinsonian disability and dyskinesia were assessed for 5-min every 10-min, the score given being most representative of each 5-min observation period. Scores were summed for each hour for time-course analyses and across the entire observation period (0-6 h). Thus, for measures parkinsonian disability and dyskinesia, the maximum scores possible (equating to severe) over the 0-6 h period were 360 and 144 respectively.

The duration of anti-parkinsonian action, on-time, was defined as the number of minutes for which the bradykinesia score was zero. In addition, the duration of on-time associated with dyskinesia of varying severity was calculated as follows. On-time with disabling dyskinesia, 'bad'—on-time was calculated the number of minutes for which the bradykinesia score was zero while the dyskinesia score was greater than 2. Meanwhile, on-time without disabling dyskinesia, 'good'—on-time represents the number of minutes for which the bradykinesia score is zero while the dyskinesia score is 2 or less.

Statistical analyses: Data derived from assessment of duration and quality of on-time were plotted as mean±s.e.m. Statistical analyses for these data were performed using parametric repeated measures one- or two-way ANOVA as appropriate, followed by Holm-Sidak multiple comparison's tests. Data for measures of parkinsonian disability and dyskinesia were graphed, where appropriate, as median scores alone (time course) or box and whisker plots (cumulated totals). Time course data for parkinsonian disability and dyskinesia were first ranked within each animal across all treatments using Excel's RANKAVG function. These transformed data were then analyzed in GraphPad Prism (v 7.02) and subjected to non-repeated measures 2-way ANOVA followed by Holm-Sidak multiple comparison tests. Cumulated disability and dyskinesia data were analyzed using a Friedman test followed by a Dunn's Multiple Comparisons test.

Results

In Vitro Pridopidine Receptor Binding Profile.

Pridopidine binding was evaluated in radioligand binding assays as described in the materials and methods. In-vitro binding assays were performed against novel receptors and as validation of previously reported targets for pridopidine. Pridopidine was found to have highest affinity for the S1R with an IC50 of 0.14 μM (140 nM). Pridopidine also shows low-affinity binding to additional receptors, in the micromolar range including serotonin (or 5-hydroxytryptamine [5-HT]) 5-HT1A, 5-HT2A, and 5-HT7; adrenergic alpha-1, adrenergic alpha-2A and alpha-2C; dopamine D3; muscarinic M2; and histamine H3 (see Table 1, below). Only negligible or no binding of pridopidine against the dopamine D2 receptors (D2R) was detected. Additional targets were tested including NMDAR, 5-HT6, Tachykinin NK1, Dopamine transporter (DAT), Norepinephrine transporter (NET) and the Serotonin transporter (SERT) with no observed binding.

TABLE 1

| Target receptor | $IC_{50}$ (μM) | $K_i$ (μM) | nH |
| --- | --- | --- | --- |
| Sigma-1 ($S_1R$) | 0.14 | 0.057 | 0.87 |
| Adrenergic $\alpha_{2C}$ | 3.56 | 1.58 | 0.76 |
| Dopamine $D_3$ | 4.79 | 1.63 | 0.90 |
| Serotonin 5-$HT_{1A}$ | 6.36 | 3.63 | 0.72 |
| Sigma-2 ($\sigma_2R$) | 7.16 | 5.45 | 0.80 |
| Serotonin 5-$HT_{2A}$ | 24.5 | 7.00 | 0.81 |
| Serotonin 5-$HT_7$ | 14.8 | 8.51 | 1.02 |
| Adrenergic $\alpha_{2A}$ | 22.0 | 11.0 | 0.98 |
| Histamine $H_3$ | 37.6 | 18.3 | 0.85 |
| Muscarinic $M_2$ | 58.1 | 24.4 | 0.62 |
| Dopamine $D_2$ | 88.4 | 29.5 | 0.94 |

$IC_{50}$ = half maximum inhibitory concentration
$K_i$ = inhibition constant calculated using the equation of Cheng and Prusoff.
nH = Hill coefficient, defining the slope of the competitive binding curve, was calculated using MathIQTM.

Pharmacokinetic Profile of Pridopidine in the MPTP-Lesioned Macaque

All doses of pridopidine assessed (7, 15, 20 and 30 mg/kg) were well tolerated. Oral administration of pridopidine 7, 15, 20 and 30 mg/kg, was associated with geometric mean Cmax values of 384, 952, 1487 and 2676 ng/ml (corresponding to 1.4, 3.4, 5.3 and 9.5 μM, respectively) and $AUC_{0-24}$ values of 1214, 4905, 8207 and 22987 ng*h/ml (corresponding to 4.3, 17.5, 29.2 and 81.8 h*μM, respectively)

S1R and moderate affinity receptor occupancies were assessed as indicated in Table 2, below, using (i) known binding affinities of pridopidine to human and rodent receptors in vitro (ii) published in vivo PET imaging in rats (Sahlholm 2015) and non-human primate (NHP), and (iii) the extensive pharmacokinetic profiling of pridopidine in the different species.

TABLE 2

Expected Occupancy of Rodent and NHP S1R and D2R at Pridopidine Doses

| Species | Dose (PO) | $C_{max}$ (ng/ml) | $C_{max}$ (µM) | $AUC_{0-24}$ (h*ng/ml) | $AUC_{0-24}$ (h*µM) | % $S_1R$ occupancy | % $D_2R$ occupancy |
|---|---|---|---|---|---|---|---|
| Rat | 3 mg/kg | 281 | 1 | 2276 | 8 | 60 | 0 |
| | 15 mg/kg | 1407 | 5 | 11380 | 41 | 85 | 0 |
| | 60 mg/kg | 5628 | 20 | 45519 | 162 | >85 | 45 |
| NHP | 7 mg/kg | 384 | 1.4 | 1214 | 4.3 | 60-80 | <15 |
| | 15 mg/kg | 952 | 3.4 | 4905 | 17.5 | >80 | 15 |
| | 20 mg/kg | 1487 | 5.3 | 8207 | 29.2 | >80 | 25 |
| | 30 mg/kg | 2676 | 9.5 | 22987 | 81.8 | >80 | 40 |

The non-human primate (NHP) data is most relevant to the following discussion. Cmax values for rat and NHP as a function of oral pridopidine dose are based on internally accumulated PK data in addition to data presented here. Rat S1R and D2R occupancy data are based on in vivo measurements at 3 and 15 mg/kg (Sahlholm 2015), NHP D2R occupancy data is based on in vivo PET imaging with the specific D2R ligand 11C-raclopride. NHP S1R occupancy data are extrapolated from in vitro binding investigations with 3H-fluspidine, a known and specific S1R tracer, against human S1R.

It is speculated that at low doses (7, 15 mg/kg), pridopidine's effect is mainly mediated by the S1R, while at higher doses (20 mg/kg and 30 mg/kg, pridopidine binds the S1R as well as a more complex activity of pridopidine is initiated by binding to the additional low affinity receptors.

Orally administered pridopidine was well tolerated at all doses assessed. The effects of acute combination of pridopidine with L-DOPA on parkinsonian disability, dyskinesia (including dystonic and choreiform), and duration and quality of on-time are shown in FIGS. 5-10.

Pridopidine Reduces Established L-DOPA-Induced Dyskinesia in the MPTP-Lesioned Macaque Pridopidine produces a significant and dose-dependent reduction in dyskinesia evoked by L-DOPA. Examining the whole 6 hr time-course reveals a significant effect of combination treatment (F (3, 28)=4.981, P=0.0068) but not time (F (5, 140)=0, P>0.9999) or the interaction of treatment and time (F (15, 140)=0.9595, P=0.5011) on levels of dyskinesia (2-way, RM-ANOVA). Compared to L-DOPA-vehicle treatment, there was a significant decrease in dyskinesia during the first hour (20 mg/kg) and first and second hours (30 mg/kg) after start of observation in response to L-DOPA when combined with pridopidine, with median levels remaining between moderate and marked (20 mg/kg) or mild to moderate (30 mg/kg)(all P<0.05) (Table 3). Assessing levels of dyskinesia cumulated over the two-hour period after start of observations (0-2 h period) revealed a significant effect of pridopidine combination treatment (0-2 h; Friedman Statistic (FS)=11.66, P=0.0087, FIG. 5B) on levels of dyskinesia evoked by L-DOPA. Median levels of dyskinesia in L-DOPA-treated animals combined with high-dose pridopidine (30 mg/kg) were reduced by 71% compared to those seen following L-DOPA-vehicle such that median levels were below mild (non-disabling) (P<0.01).

Figure 5A:
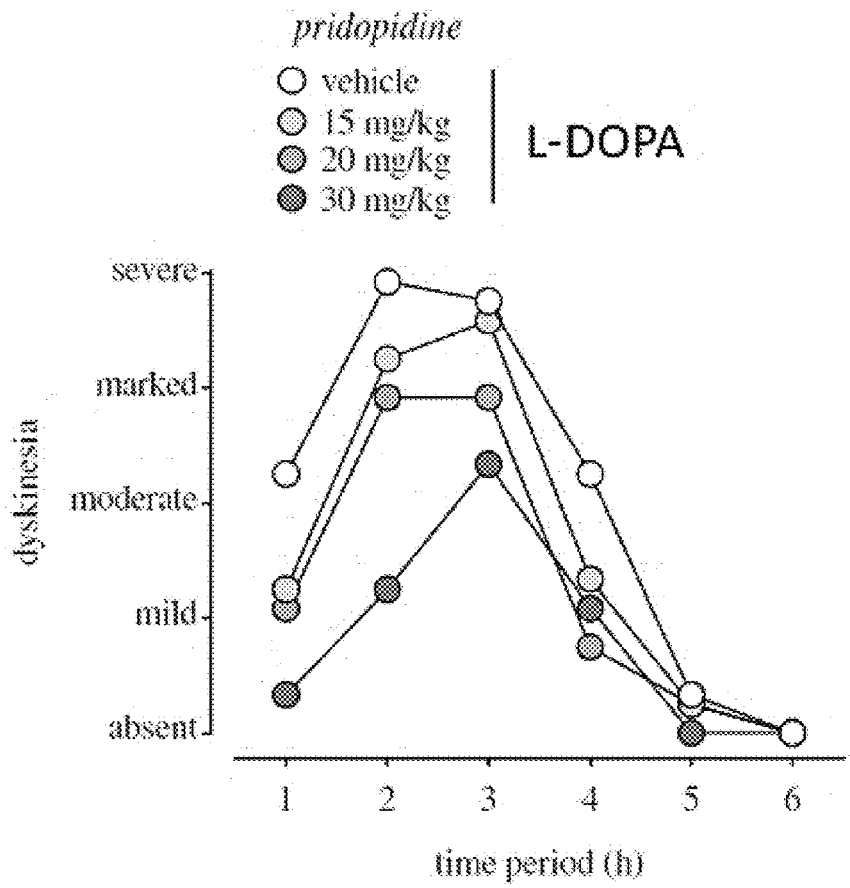
FIG. 5A: Graph showing dyskinesia (time course 0-6 hr) (study 2). Pridopidine high dose reduces established dyskinesia evoked by high L-DOPA. Y axis is severity of dyskinesia, X axis shows time course, 0-6 hr.

Table 3 shows the p-values associated with the 6 hour data presented in FIG. 5A for Dyskinesia (time course) in study 2. Pridopidine reduces established dyskinesia evoked by high L-DOPA.

TABLE 3

| | L-DOPA-vehicle (hr) | |
|---|---|---|
| pridopidine | 1 | 2 |
| 15 mg/kg | ns | ns |
| 20 mg/kg | * | ns |
| 30 mg/kg |  | * | ns: not significant.
*//* represents P < 0.05, P < 0.01 or P < 0.001 cf. vehicle-treatment. 2-way RM ANOVA with Holm-Sidak's test or Friedman test with DUNN'S test.

Figure 6A:
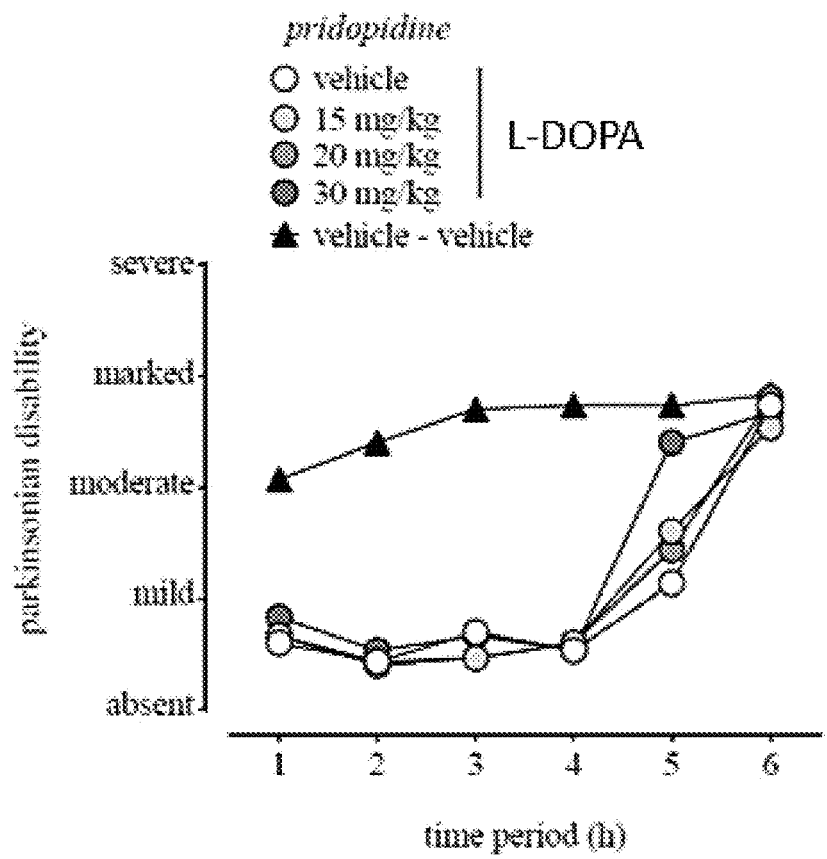
FIG. 6A: Graph showing Parkinsonian disability (time course 0-6 hr): L-DOPA administration reduces the parkinsonian disability for approximately 4 hours. Pridopidine does not reduce the anti-parkinsonian benefit of L-DOPA (study 2). Y axis is severity of parkinsonian disability, X axis shows time course in hours. Triangles: vehicle/vehicle (no L-DOPA and no pridopidine) treated animals; circles: L-DOPA/vehicle or L-DOPA/pridopidine treated animals.

Pridopidine does not Reduce the Beneficial Effect of L-DOPA on Parkinsonian Disability MPTP NHPs demonstrate moderate to marked levels of parkinsonian disability when untreated. L-DOPA treatment reduces parkinsonian disability to absent to mild levels for 3-4 hours. Pridopidine does not reduce L-DOPA's beneficial effect on parkinsonian disability. FIG. 6A time course (0-6 hr) and FIG. 6B bar graph (0-2 hour accumulated) show levels of Parkinsonian disability. Pridopidine does not reduce the anti-parkinsonian benefit of L-DOPA (study 2).

Table 4 presents the p-values corresponding to the data shown in FIG. 6A, showing that pridopidine has no adverse effect on parkinsonism in L-DOPA treated animals, resulting from additional therapy with pridopidine at all doses (study 2).

TABLE 4

Pridopidine had no adverse effect on the anti-parkinsonian benefit of L-DOPA

| | L-DOPA-vehicle (hr) | | | | | |
|---|---|---|---|---|---|---|
| pridopidine | 1 | 2 | 3 | 4 | 5 | 6 |
| 15 mg/kg | ns | ns | ns | ns | ns | ns |
| 20 mg/kg | ns | ns | ns | ns | ns | ns |
| 30 mg/kg | ns | ns | ns | ns | ns | ns |

Figure 5B:
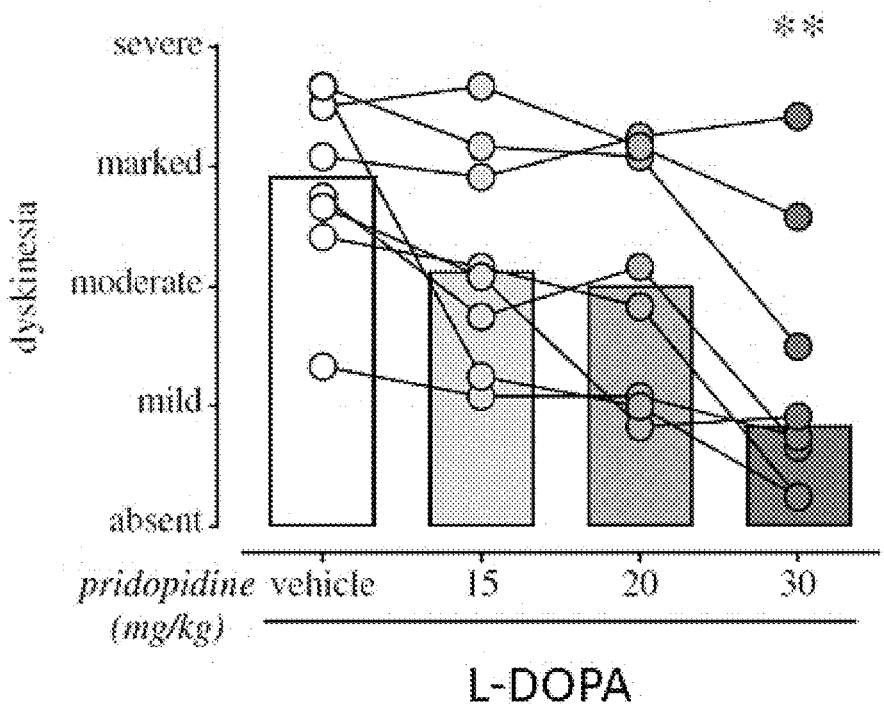
FIG. 5B: Bar graph showing dyskinesia (0-2 hr accumulated) (study 2): Dyskinesia is evoked by high dose L-DOPA. Pridopidine reduces L-DOPA induced dyskinesia in a dose dependent manner. At the high dose of 30 mg/kg this effect is pronounced and statistically significant (p<0.01). Y axis is severity of dyskinesia, X axis shows pridopidine doses.
Figure 6B:
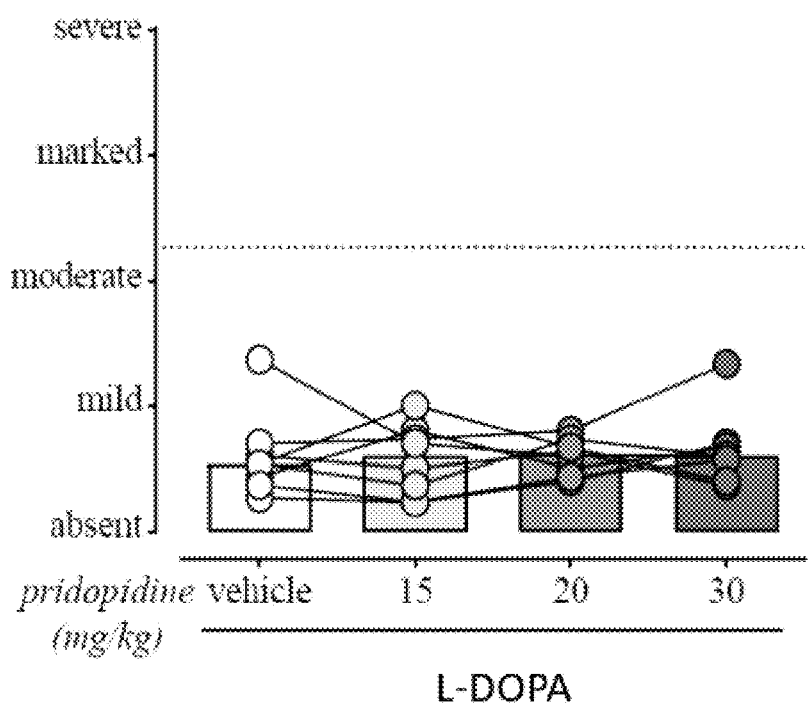
FIG. 6B: Bar graph showing Parkinsonian disability (0-2 hr accumulated). Pridopidine does not reduce the anti-parkinsonian benefit of L-DOPA (study 2). Y axis is severity of parkinsonian disability, X axis shows pridopidine doses.

Levels of dyskinesia (FIGS. 5A-5B) and parkinsonism disability (FIGS. 6A-6B) were assessed over a 6 hour period (FIGS. 5A and 6A) or cumulated across the 0-2 hour period of peak-effect (FIGS. 5B and 6B). Data are median (Tables 3 and 4) with individual values (FIGS. 5A-5B and 6A-6B).
N = 8 for all treatment groups.
*//* represents P < 0.05, P < 0.01 or P < 0.001, ns—non-significant cf. vehicle-treatment. 2-way RM ANOVA (Tables 3 and 4) with Holm-Sidak's test or Friedman test with DUNN'S test (FIGS. 5A-5B and 6A-6B).

Figure 7A:
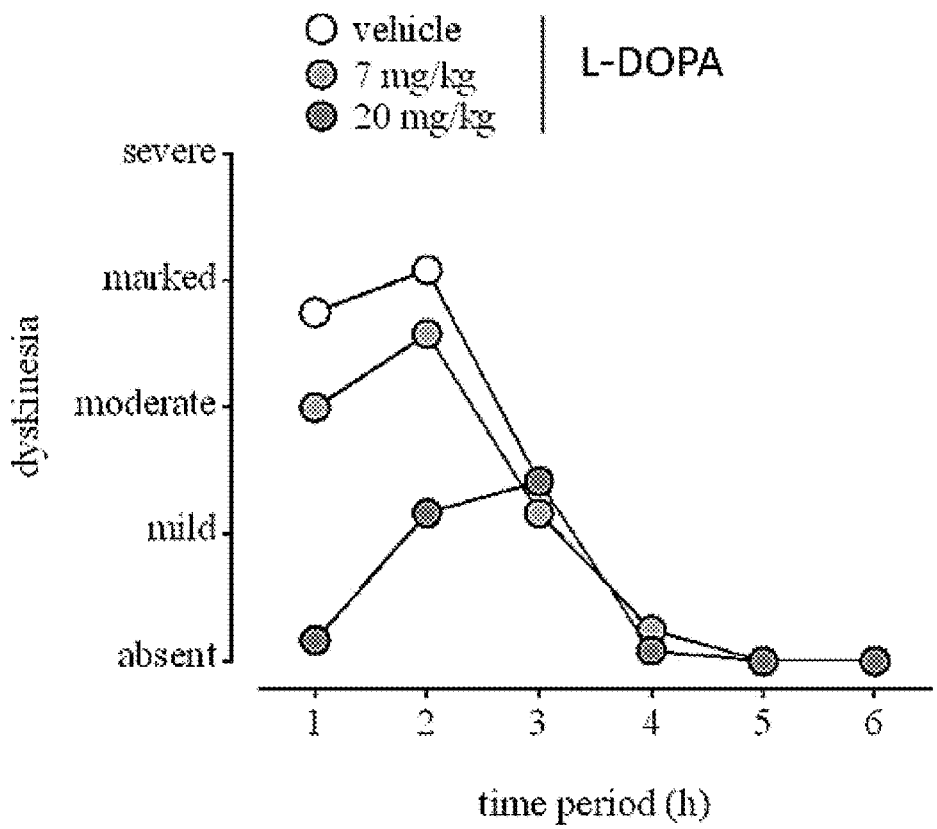
FIG. 7A: Graph showing dyskinesia (time course 0-6 hr) (study 1): High dose L-DOPA induces dyskinesia. Pridopidine reduces established dyskinesia at the high dose. Y axis is severity of dyskinesia, X axis shows time course in hours.
Figure 7B:
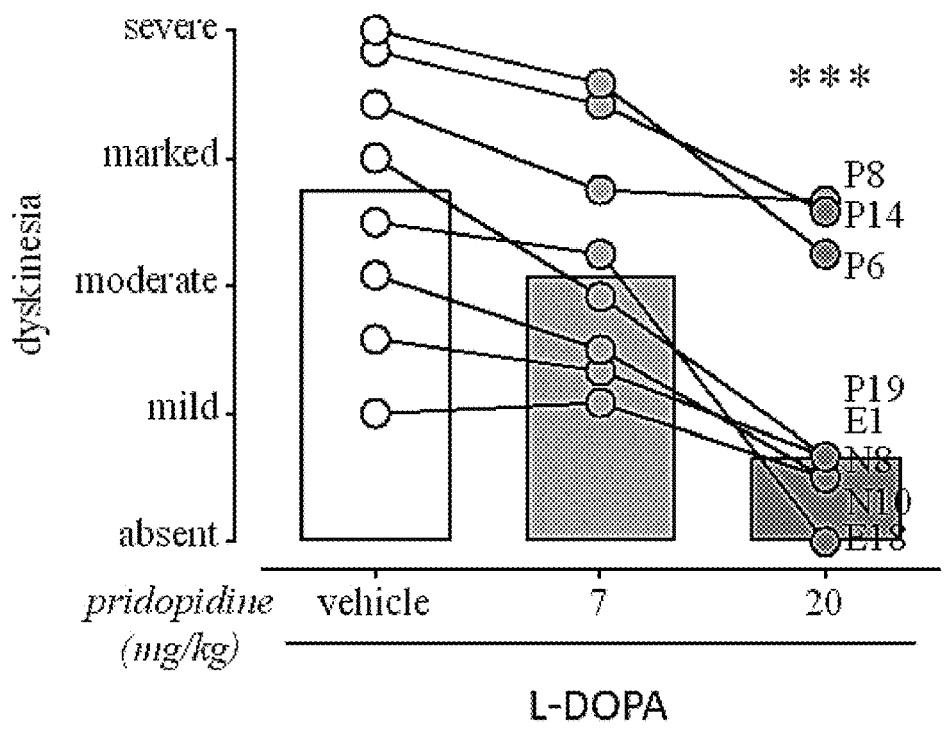
FIG. 7B: Bar graph showing dyskinesia (0-2 hr accumulated) (study 1): Pridopidine high dose reduces established dyskinesia evoked by high dose L-DOPA. Y axis is severity of dyskinesia, X axis shows pridopidine doses.
Figure 8A:
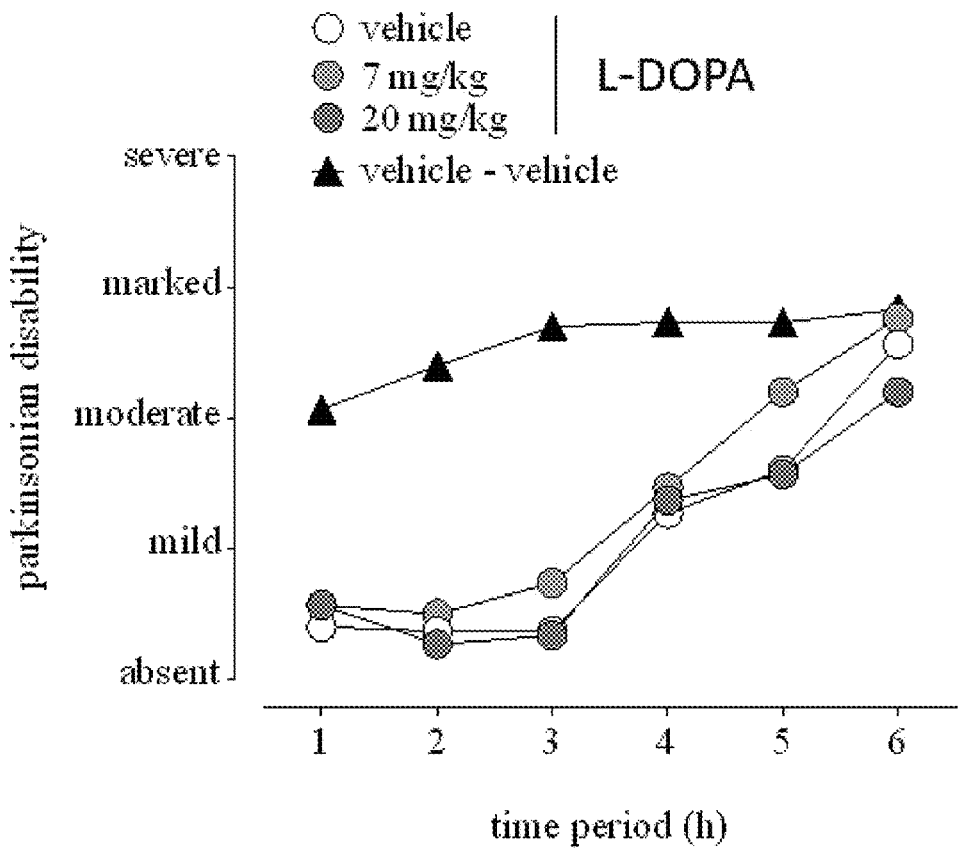
FIG. 8A: Graph showing Parkinsonian disability (time course 0-6 hr): L-DOPA reduces parkinsonian disability from moderate to nearly absent in the MPTP NHP model. Pridopidine does not reduce the anti-parkinsonian benefit of L-DOPA. (study 1). Y axis is severity of parkinsonism (parkinsonian disability), X axis shows time course in hours.

Data from study 1: Pridopidine produces a significant and dose dependent reduction in dyskinesia evoked by L-DOPA in study 1 (FIGS. 7A-7B). L-DOPA induces moderate to marked dyskinesia. The lower dose of pridopidine (7 mg/kg) produces a modest decrease, and the higher dose of 20 mg/kg a more significant one—reducing dyskinesia to absent to mild levels. FIG. 7A examining the whole 6 hr time course and FIG. 7B bar graph showing individual animals at 0-2 hours accumulated after L-DOPA administration. This decrease was observed in the absence of any change to the total duration of on-time or extent of anti-parkinsonian benefit of L-DOPA (FIGS. 8A-8B).

L-DOPA demonstrates anti-parkinsonian effects, reducing the moderate to marked parkinsonian disability levels to absent to mild levels. Pridopidine has no adverse effect on parkinsonian disability levels in L-DOPA treated animals (FIGS. 8A-8B). FIG. 8A examining the whole 6 hr time course and FIG. 8B is a bar graph showing individual animals at 0-2 hours after L-DOPA.

Figure 8B:
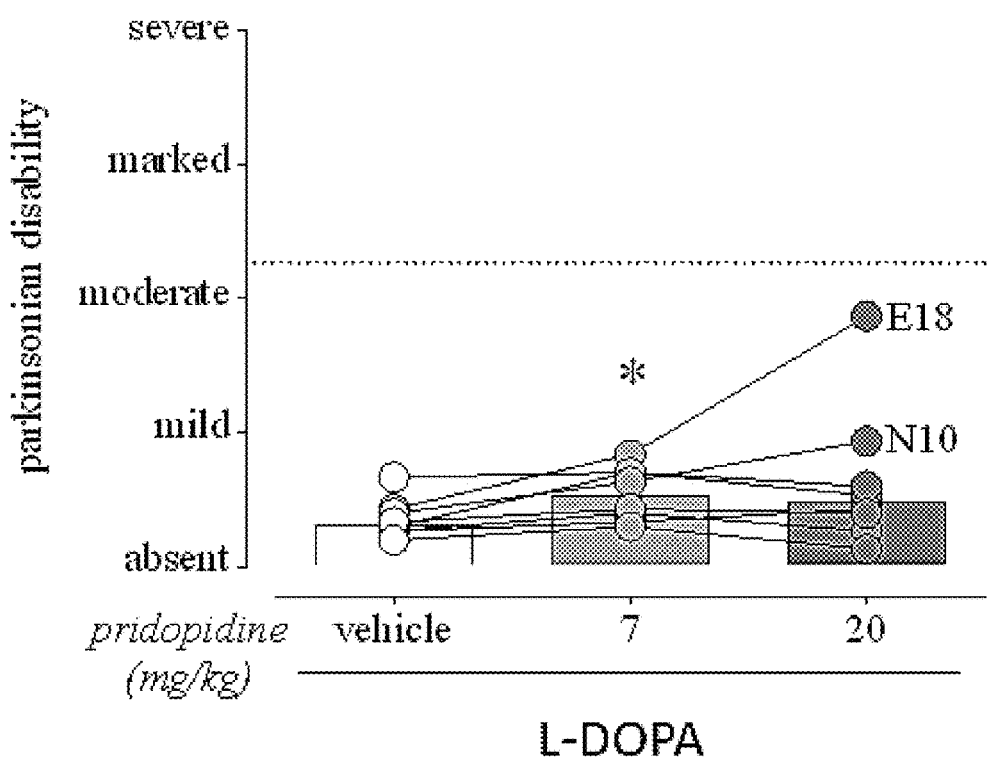
FIG. 8B: Bar graph showing Parkinsonian disability (0-2 hr accumulated). Pridopidine does not reduce the anti-parkinsonian benefit of L-DOPA (study 1). Y axis is severity of parkinsonian disability, X axis shows pridopidine doses.
Figure 9A:
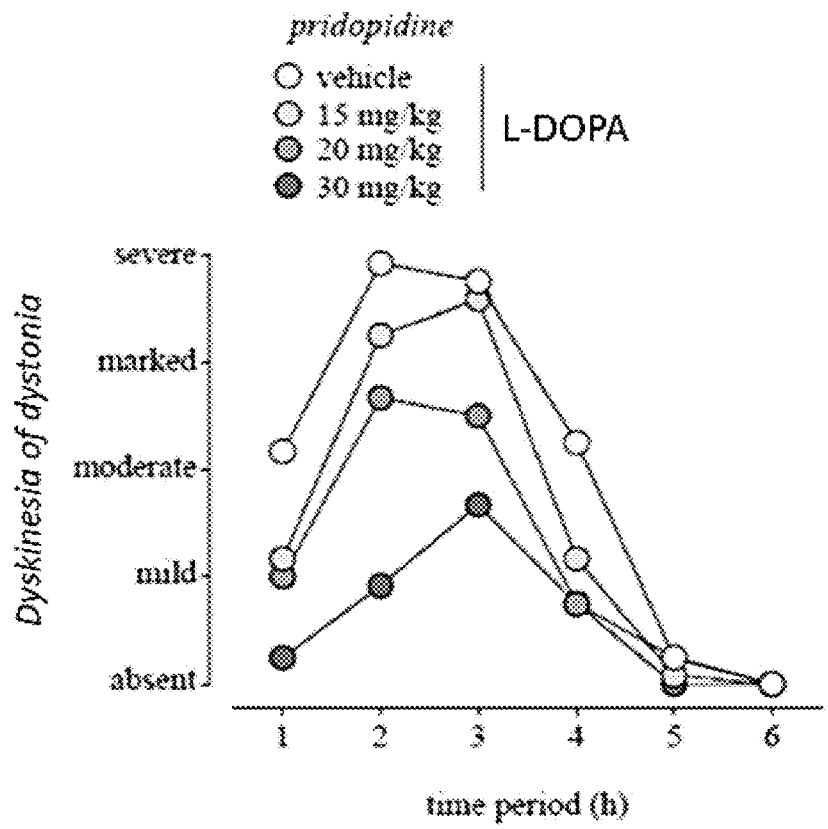
FIG. 9A: Graph showing that pridopidine high dose reduces L-DOPA induced dyskinesia of dystonia (study 2). Y axis is severity of dystonia, X axis time course 0-6 hours.
Figure 9B:
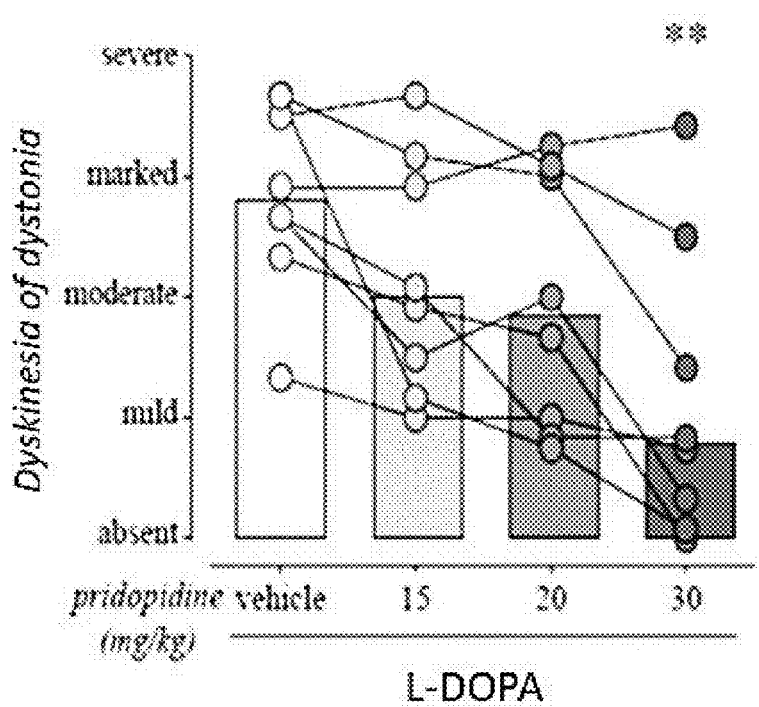
FIG. 9B. Bar graph showing pridopidine effect on L-DOPA induced dyskinesia of dystonia (0-2 hr accumulated) (study 2): Pridopidine high dose (30 mg/kg dose) reduces dystonia significantly (p<0.01). Y axis is severity of dystonia, X axis shows pridopidine doses.

Data are medians (FIGS. 7A, 8A) with individual values (FIGS. 7B, 8B). N=8 for all treatment groups. *//* represents P<0.05, P<0.01 or P<0.001 cf vehicle-treatment, 2-way ANOVA with Holm-Sidak PHT (FIGS. 7A, and 8A), Friedman's test with Dunn's PHT (FIGS. 7B, 8B). For reference (but not included in statistical analyses, ▲ describes data in response to vehicle-vehicle treatment).

Pridopidine Reduces L-DOPA Induced Dystonia Levels in the MPTP NHP Model of PD.

L-DOPA treatment induces marked to severe levels of dystonia in MPTP NHPs. Pridopidine produces a significant and dose-dependent reduction in levels of L-DOPA-induced dystonia. Pridopidine demonstrates a significant decrease in L-DOPA-induced dystonia during the first hour (20 and 30 mg/kg) and second and third hours (30 mg/kg) after start of observation, with median levels remaining between moderate and marked (20 mg/kg) or mild to moderate (30 mg/kg) (all P<0.05). Examination of the whole 6 hr time-course reveals a significant effect of combination treatment (F (3, 28)=7.017, P=0.0012) but not time (F (5, 140)=0, P>0.9999) or the interaction of treatment and time (F (15, 140)=0.9735, P=0.4863) on levels of dystonia (2-way, RM-ANOVA, FIG. 9A, Table 5). Table 5 presents the p-values associated with the results shown in FIG. 9A.

TABLE 5

Effect of escalating doses of pridopidine on L-DOPA induced Dystonia

| pridopidine | L-DOPA-vehicle (hr) | | |
|---|---|---|---|
| | 1 | 2 | 3 |
| 15 mg/kg | ns | ns | ns |
| 20 mg/kg | * | ns | ns |
| 30 mg/kg |  | * | * | ns: not significant.
*//* represents P < 0.05, P < 0.01 or P < 0.001 cf. vehicle-treatment. 2-way RM ANOVA with Holm-Sidak's test or Friedman test with DUNN'S test Assessing levels of dystonia cumulated over the 0-2 h period reveals a significant effect of pridopidine combination treatment (0-2 h; Friedman Statistic (FS)=11.88, P=0.0078, FIG. 9B) on levels of dystonia evoked by L-DOPA administration. Median levels of dystonia in animals treated with L-DOPA combined with high-dose pridopidine (30 mg/kg) were reduced (by 72%) compared to that seen following L-DOPA-vehicle such that median levels of dyskinesia were below mild (non-disabling) (P<0.01).

Figure 10A:
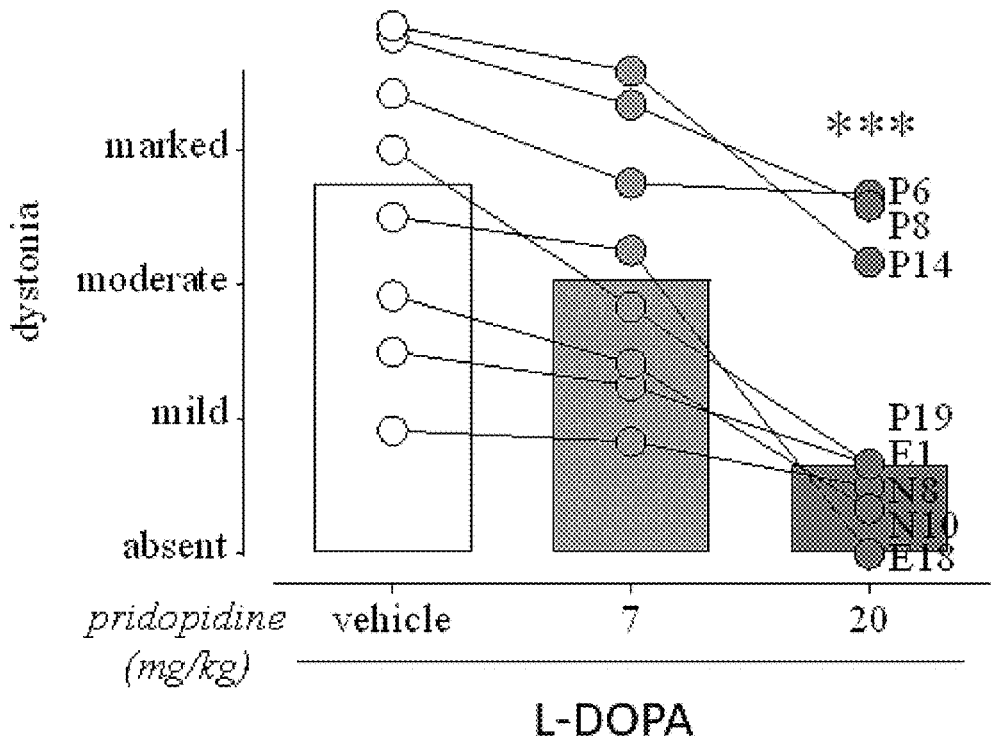
FIG. 10A: Bar graph showing pridopidine high dose reduces L-DOPA-induced dyskinesia of dystonia (0-2 hr accumulated) (study 1): L-DOPA invoked moderate to marked dystonia in the MPTP NHP model of PD. Pridopidine high dose reduces L-DOPA induced dyskinesia of dystonia. Y axis is severity of dystonia, X axis shows pridopidine doses.

The effect of pridopidine on L-DOPA induced dystonia were also assessed in study 1. Pridopidine significantly reduces L-DOPA induced dystonia (study 1), in a dose dependent manner. FIG. 10A, shows cumulated dystonia levels at 0-2 hours post L-DOPA administration and a significant and dose-dependent reduction of L-DOPA-induced dystonia levels over a 0-2 hr time period with pridopidine.

Figure 10B:
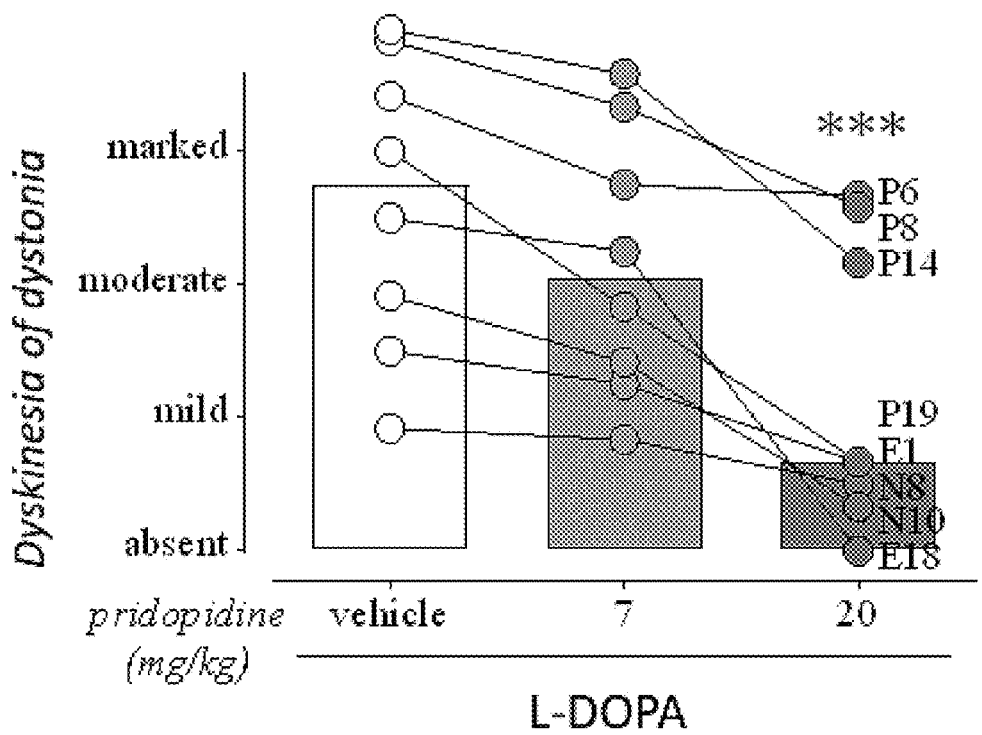
FIG. 10B: Bar graph showing pridopidine effect on L-DOPA induced dyskinesia of chorea (0-2 hr accumulated) (study 1): L-DOPA invokes moderate dyskinesia of chorea in the MPTP NIP model. Pridopidine reduces L-DOPA induced dyskinesia of chorea at the high dose, but not at the low dose. Y axis is severity of chorea, X axis shows pridopidine doses.

L-DOPA treatment also induces levels of chorea in MPTP NHPs. High dose pridopidine significantly reduces L-DOPA induced chorea. FIG. 10B (study 1) shows cumulated chorea levels at 0-2 hours post L-DOPA administration and a significant and dose-dependent reduction of L-DOPA-induced chorea levels over a 0-2 hr time period with pridopidine.

Pridopidine Increases the Duration of "Good" On-Time (Defined as on Time without Dyskinesia or with Non-Disabling Dyskinesia).

Figure 11:
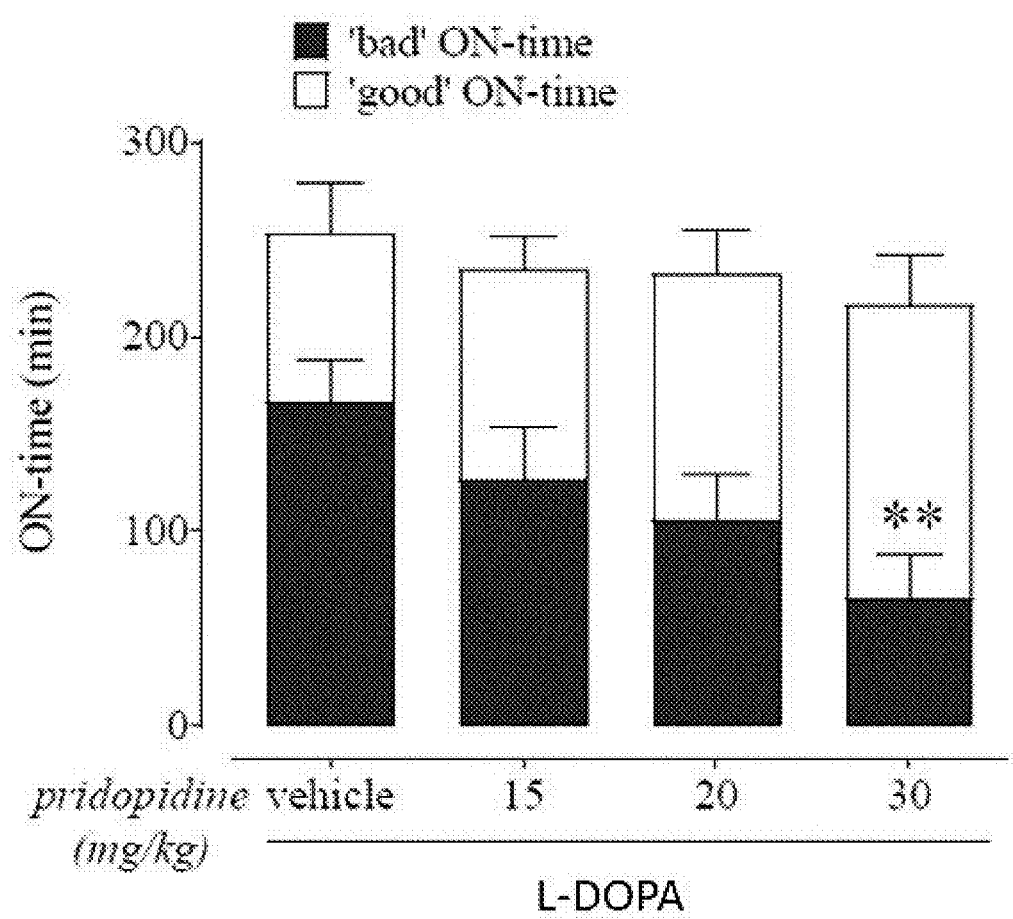
FIG. 11: Bar graph showing the effects of pridopidine on duration and quality of on-time (study 2). Pridopidine demonstrates a dose dependent lowering bad "on-time", defined as on-time with dyskinesia. The effect is pronounced and significant at high dose (30 mg/kg dose), reducing bad "on-time" by ~50% compared to untreated controls.

Pridopidine produced no change in the total duration of on-time Pridopidine improves the quality of on-time associated with L-DOPA, increasing "good" on time and decreasing "bad" on time (good on time is on-time without disabling dyskinesia; bad on time is on time with disabling dyskinesia) in a dose-dependent manner. The most significant effect is observed at the highest dose of 30 mg/kg, with a 60% reduction in bad on time compared to vehicle (66 min cf. 168 min respectively, p<0.01) (FIG. 11; "bad" on time black, "good" on time white, y axis=minutes). Specifically, assessed over the six-hour period of observation while there was no effect of treatment (F (3, 21)=1.659, P=0.2062), there was significant effect of on-time subtype (total, good or bad; F (2, 14)=18.29, P=0.0001) and the interaction of treatment and subtype (F (6, 42)=2.887, P=0.0190) on duration and quality of on-time (2-way, RM-ANOVA, FIG. 11).

Discussion

Parkinsonism was induced in cynomolgus macaques by MPTP injection. The extent of lesion produced by this regimen (Johnston 2013) is comparable to that observed in advanced Parkinson's patients and typical of MPTP-lesioned animals with robust parkinsonism. The doses of L-DOPA employed as part of the current study provided maximal anti-parkinsonian benefit for a typical duration of ~3 hours. This benefit was compromised by disabling dyskinesia induced by L-DOPA (greater than moderate levels). Indeed, the duration of L-DOPA efficacy was mirrored by the duration of L-DOPA-induced dyskinesia. Although those doses of L-DOPA administered in clinical settings are generally lower, on a mg/kg basis than those administered to the MPTP-lesioned macaque even corrected for human equivalent dosing (HED), we show that they deliver equivalent plasma pharmacokinetic profiles to those achieved with clinically relevant L-DOPA doses as given to PD patients (Dizdar 1999; Huot 2012).

The cellular target of pridopidine was evaluated in various in vitro binding assays. Pridopidine binds with highest affinity to the Sigma-1 receptor (S1R, binding IC50~100 nM), >100 fold higher affinity compared to an earlier described target, the Dopamine D2 receptor (D2R) (IC50~10-29.5 µM) and to several other central nervous system (CNS) receptor targets, including, serotonin (5-hydroxytryptamine [5-HT]) 5-HT1A, 5-HT2A, and 5-HT7; adrenergic alpha-1, adrenergic alpha-2A and alpha-2C; dopamine D3; and muscarinic M2, all in the mid micromolar range.

All doses of pridopidine assessed (7, 15, 20 and 30 mg/kg) were well tolerated. Oral administration of pridopidine 7, 15, 20 and 30 mg/kg, was associated with geometric mean $C_{max}$ values of 384, 952, 1487 and 2676 ng/ml (corresponding to 1.4, 3.4, 5.3 and 9.5 µM, respectively) and $AUC_{0-24}$ values of 1214, 4905, 8207 and 22987 ng*h/ml (corresponding to 4.3, 17.5, 29.2 and 81.8 h*μM). Receptor occupancy was estimated using (i) known binding affinities of pridopidine to human and rodent S1R and D2R in vitro (ii) in vivo PET imaging in rats, NHP and human, and (iii) pharmacokinetic PK profiling in the different species. Plasma exposures observed following the low, ineffective doses (7 mg/kg and 15 mg/kg (study 1), is expected to be associated with full S1R occupancy >80% but with negligible engagement of low affinity dopamine receptors. Plasma exposures following the high, effective dose (30 mg/kg (or 20 mg/kg in study 1)) is expected to saturate the S1R (>80% occupancy) and have a higher (about 40%) occupancy of the low affinity dopamine receptors.

In summary, in MPTP-lesioned NHPs, high-dose pridopidine produced a significant and meaningful decrease in LID without compromising the anti-parkinsonian benefit of L-DOPA.

Contrary to what was observed in HD, surprisingly—administration of pridopidine at low doses was ineffective against LID whereas high doses of pridopidine exhibited beneficial effects in reducing in LID in a PD NHP model. In HD, by contrast, pridopidine is beneficial at low doses but no benefit is observed at high doses. These studies provide data to support the use of high-dose pridopidine for the treatment of dyskinesia and DIMD, including LID in PD patients.

Example 4: Combination Therapy of Pridopidine with Amantadine (AMT) Demonstrates a Synergistic Effect for Reducing Abnormal Involuntary Movements (AIMS) in a Preclinical Rat Model of PD This study assessed whether the combination of pridopidine and amantadine could enhance the anti-dyskinetic benefit for levodopa induced dyskinesia achieved by either drug given alone AMT is the gold standard for treating levodopa induced dyskinesia in PD patients.

The first Experiment in this study assayed a dose-dependent response of pridopidine on L-DOPA induced AIMS and net contraversive rotations in a rat model of PD. The effects of acute administration of vehicle$_1$ or 4 doses of pridopidine (3, 15, 30 or 60 mg/kg) given in combination with L-DOPA were determined via assessment of AIMS and rotational behavior prior to, and every twenty minutes for 3 h after administration of L-DOPA for a total of 10 assessments (FIGS. 12A-12D to 14A-14C).

The second Experiment assessed the anti-dyskinetic benefit of a single dose of pridopidine (15 mg/kg, PO) previously shown to produce subthreshold results, given alone and in combination with two suboptimal doses of AMT (5 and 10 mg/kg, SC) (FIGS. 15A-15D) that were characterized previously to produce subthreshold (5 mg/kg) and an approximate 50% reduction (10 mg/kg) in AIMS and net contraversive rotations (NCRs).

Experimental:

The anti-dyskinetic activity of acute administration of each treatment alone and in combination on L-DOPA-induced abnormal involuntary movements (AIMS) was assessed in the 6-hydroxydopamine (6-OHDA)-lesioned rat model of PD. AIMS represent a rodent correlate of LID.

Twenty female Sprague Dawley rats received unilateral injections of 6-OHDA into the medial forebrain bundle. From these animals, those showing a robust rotational response following administration of apomorphine (a minimum of N=10) were selected for subsequent testing.

These animals then received once-daily administration of L-DOPA (10 mg/kg, IP) for a period of 3 weeks until stable and robust AIMS were evoked, i.e. a model of advanced PD when motor complications have become established. The power calculation was based upon defining a change in levels of AIMS during the peak-effect period (20-120 min post L-DOPA administration Following completion of baseline behavioral testing, the effects of acute administration of six treatment combinations were assessed. The treatment combinations are detailed in the following Table 7.

TABLE 7

Treatment combinations

| Treatment # | Treatment 1 Pridopidine (PO, t = 1 h) | Treatment 2 AMT (SC, t = 1 h) | Treatment 3 L-DOPA (IP, t = 0 h) | Behavioral assessment | N |
|---|---|---|---|---|---|
| 1 | Vehicle1 | Vehicle$_2$ | L-DOPA | AIMS/ rotations 3 hrs post L-DOPA | 10 |
| 2 | Vehicle1 | AMT (5mg/kg) | | | 10 |
| 3 | Vehicle1 | AMT (10 mg/kg) | | | 10 |
| 4 | Pridopidine (15 mg/kg) | Vehicle$_2$ | | | 10 |
| 5 | Pridopidine (15 mg/kg) | AMT (5mg/kg) | | | 10 |
| 6 | Pridopidine (15 mg/kg) | AMT (10 mg/kg) | | | 10 |

SC: subcutaneous administration;
PO: per os, oral administration;
t: time from drug administration.;
AIMS: abnormal involuntary movements Treatments 1-3 from Table 7:

For Treatments 1-3, high-dose L-DOPA (6 mg/kg) were combined with vehicle1 (that for pridopidine) and either vehicle2 (that for AMT) or AMT (5 and 10 mg/kg, SC).

Treatments 4-6 from Table 7 (FIGS. 15A-15D):

For Treatments 4-6, L-DOPA (6 mg/kg) was combined with pridopidine (15 mg/kg, PO) and either vehicle2 (that for AMT) or AMT (5 and 10 mg/kg, SC). L-DOPA 6 mg/kg was pre-defined as a dose that produces maximal levels of anti-parkinsonian benefit and rotation, but which is associated with severe/disabling levels of AIMS.

Vehicle1 or pridopidine and vehicle2 or AMT were administered 1 h prior to L-DOPA and start of behavioral observations (rotational behavior and AIMS, assessed for a period of 3 hours).

The order of treatments within the Study and within each animal was randomized using an incomplete Latin Square-type design.

Methods:

A total of 20 animals received unilateral lesions of the right nigrostriatal pathway via injection of 12.5 μg of 6-hydroxydopamine (6-OHDA) into a single site in the medial forebrain bundle.

Animals left untreated for 2 weeks to allow the lesion to develop and stabilize prior to start of behavioral assessments.

Two weeks following stereotaxic surgery, to gauge the extent of the 6-OHDA-induced lesion, all animals underwent assessment of contraversive rotational behavior observed in response to administration of apomorphine. Thus, animals received acute administration of apomorphine HCl (0.05 mg/kg of the freebase corrected weight, SC) and rotational behavior was assessed continuously for 90 min. All animals (with a required minimum of N=12) bearing a robust lesion (defined as producing a total of more than 50 net contraversive rotations in the first hour immediately following administration of apomorphine) were included for subsequent testing.

Following completion of animal selection assessments, all animals (minimum of 10) that reached the inclusion criteria were administered L-DOPA, once daily, for 21 days (Weeks 4-6).

AIMS and rotational behavior were assessed prior to, and every twenty minutes for 3 h after treatment administration (10 assessments). The 10 animals displaying the highest levels of AIMS (a minimum score of 3 for at least 3 consecutive periods of assessment) were advanced to the next study component. (FIGS. 12A-D, FIGS. 13A-13C and FIGS. 14A-14C).

Behavioral Assessments
Assessment of Rotational Behavior

Commencing immediately following administration of apomorphine or L-DOPA, rotational behavior was assessed using an automated rotometer apparatus (Med Associates, USA) for a period of 3 h.

Abnormal Involuntary Movements (AIMS) Testing

Animals assessed for AIMS during rotational observations. Each rat was observed for 1 min prior to treatment and every 20 min for a 3 h time period following treatment. Three subtypes of AIMS were assessed including:
Limb (Li)—Random uncontrollable movements of fore-limb contralateral to the lesion
Orolingual (Ol)—Excess chewing and jaw movements with protrusion of the tongue
Axial (Ax)—dystonic postures or choreiform twisting of the neck and upper body towards the contralateral side For each subtype, the duration of AIMS was scored between 1 and 4 as described below:
1=Present for less than 30 seconds
2=Present for more than 30 seconds
3=Present throughout the minute but suppressed by external stimuli
4=Present throughout the minute but not suppressible by external stimuli A score was given that denotes the maximum or highest score obtained across the observation period both for each of the subtypes individually and across all combined.

Figure 12A:
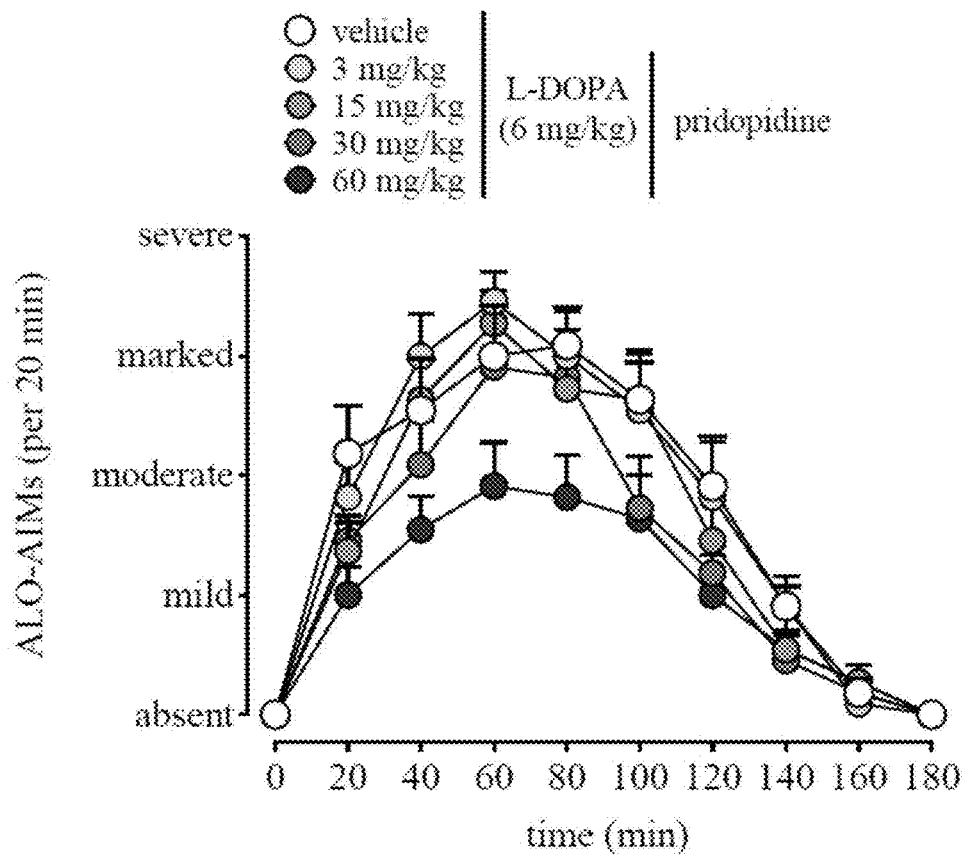
FIGS. 12A-12D present the change in levels of axial, limb and orolingual (ALO) —AIMS (abnormal involuntary movements) following treatment with pridopidine at different doses, as described in Example 8. Female 6-hydroxydopamine (6-OHDA) lesioned rats treated with L-DOPA (6 mg/kg, IP) once-daily for a period of 3 weeks as a model of advanced PD. When motor complications were established, pridopidine was administrated at 3 mg/kg, 15 mg/kg, 30 mg/kg and 60 mg/kg doses and AIMS level was assessed during 3 hrs. L-DOPA treatment invokes marked AIMS. Pridopidine significantly reduces AIMS at the high doses of 30 (p<0.05) and 60 (p<0.01) mg/kg.
Figure 12B:
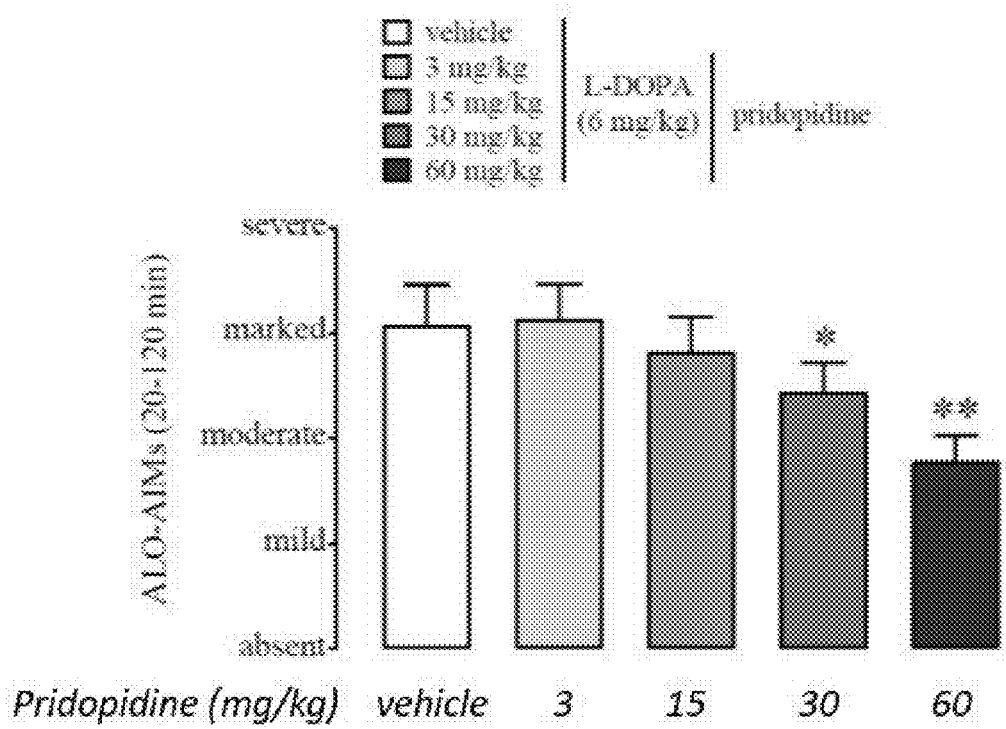

For each point of observation (1 min every 20 min) each of the three ALO-AIMS subscores (Axial, limb and orolingual) are scored from 0-4 and the resulting data summed to give a max possible score for that timepoint of 12 (max of y-axis for time-course). In categories the scores are as follows:
0—absent
3—mild
6—moderate
9—marked
12—severe For any graphs cumulated over the 20-120 min period this takes in a total of 5 time-points (20-40, 40-60, 60-80, 80-100 and 100-120). The y-axis max score is 60 with categories for each score as follows.
0—absent
15—mild
30—moderate
45—marked
60—severe Results:
High Doses of Pridopidine Reduces L-DOPA Induced AIMS in the 6-OHDA Rat Model of PD Motor complications were established in female 6-OHDA rats by 3 weeks of once daily L-DOPA treatment. Rats were administered L-DOPA (6 mg/kg), then treated with pridopidine at doses of 3 mg/kg, 15 mg/kg, 30 mg/kg and 60 mg/kg and AIMS evaluated over 3 hours. The most robust effects were observed at the high doses of 30 and 60 mg/kg. The 3 and 15 mg/kg doses did not affect AIMS (FIGS. 12A, 12B). FIG. 12A presents change in levels of AIMS during 3 hours measured every 20 minutes at different doses of pridopidine 3 mg/kg, 15 mg/kg, 30 mg/kg and 60 mg/kg vs. vehicle. FIG. 12B presents the total AIMS cumulated over the 20-120 time period of results presented in FIG. 12A. The corresponding p-values to the results presented in FIGS. 12A and 12B are also presented in Table 8.

TABLE 8

AIMS levels following treatment of pridopidine

| Pridopidine | L-DOPA/vehicle cf. (min) | | | | | |
|---|---|---|---|---|---|---|
| | 20 | 40 | 60 | 80 | 100 | 120 |
| 3 mg/kg | ns | ns | ns | ns | ns | ns |
| 15 mg/kg | * | ns | ns | ns | ns | ns |
| 30 mg/kg | ns | ns | ns | ns | * | ns |
| 60 mg/kg | ** | * | ** | ** | ** | * |

* refers to $p < 0.05$,
** refers to $p < 0.01$ and
*** refers to $p < 0.001$.
ns = no signal.

Figure 12C:
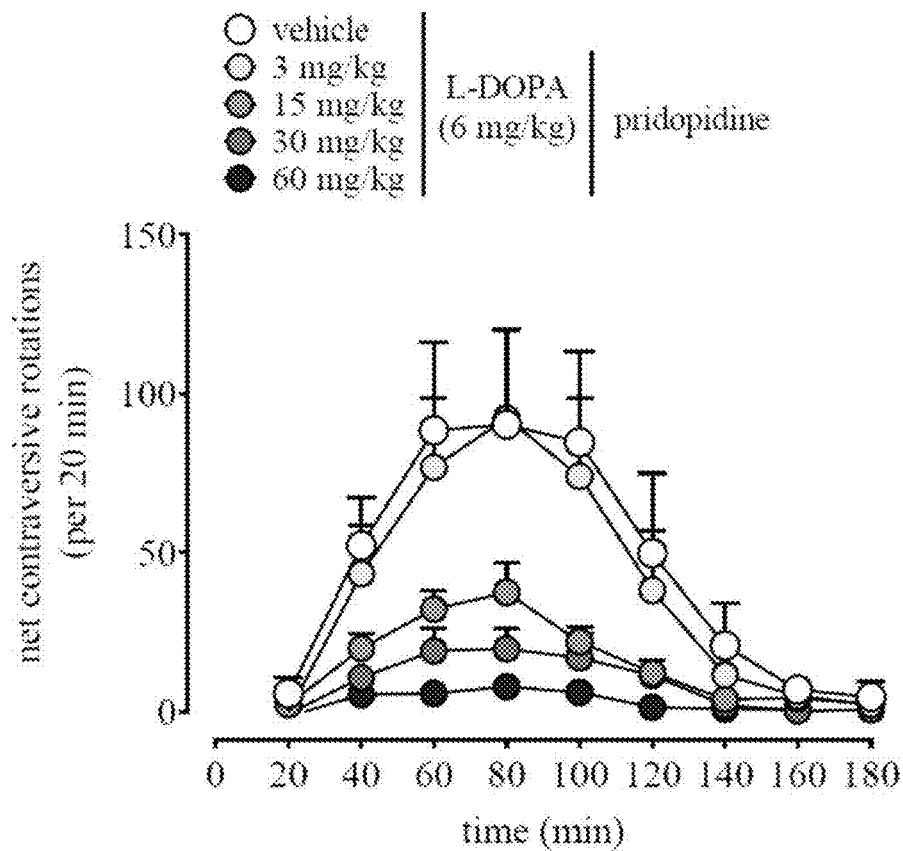
Figure 12D:
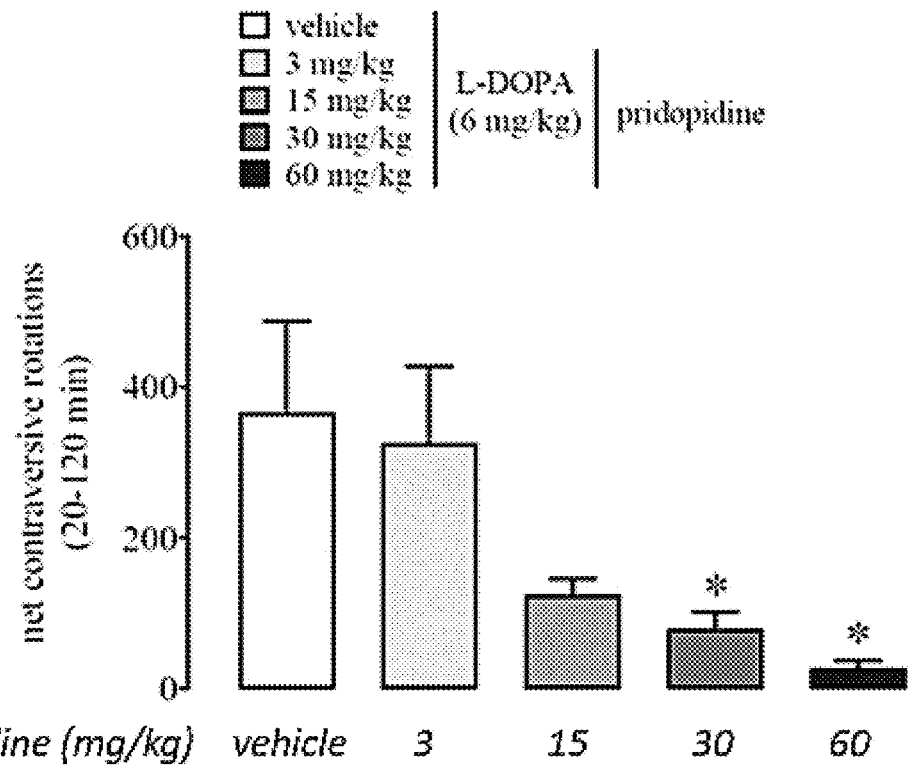

FIG. 12C presents net contraversive rotations (NCRs) of the rats during 3 hours measured every 20 minutes at different doses of pridopidine 3 mg/kg, 15 mg/kg, 30 mg/kg and 60 mg/kg vs. vehicle. FIG. 12D presents a total NCRs cumulated over the 20-120 min period of results presented in FIG. 12C. The corresponding p-values to the results presented in FIGS. 12C and 12D are also presented in Table 9.

TABLE 9

Net contraversive rotations following treatment of pridopidine

| Pridopidine | L-DOPA/vehicle cf. (min) | | | | | |
|---|---|---|---|---|---|---|
| | 20 | 40 | 60 | 80 | 100 | 120 |
| 3 mg/kg | ns | ns | ns | ns | ns | ns |
| 15 mg/kg | ns | ns | ** | ** | *** | * |
| 30 mg/kg | ns | * | *** | *** | *** | * |
| 60 mg/kg | ns | ** | *** | *** | *** | ** |

* refers to $p < 0.05$,
** refers to $p < 0.01$ and
*** refers to $p < 0.001$.
ns = no signal.

Figure 13A:
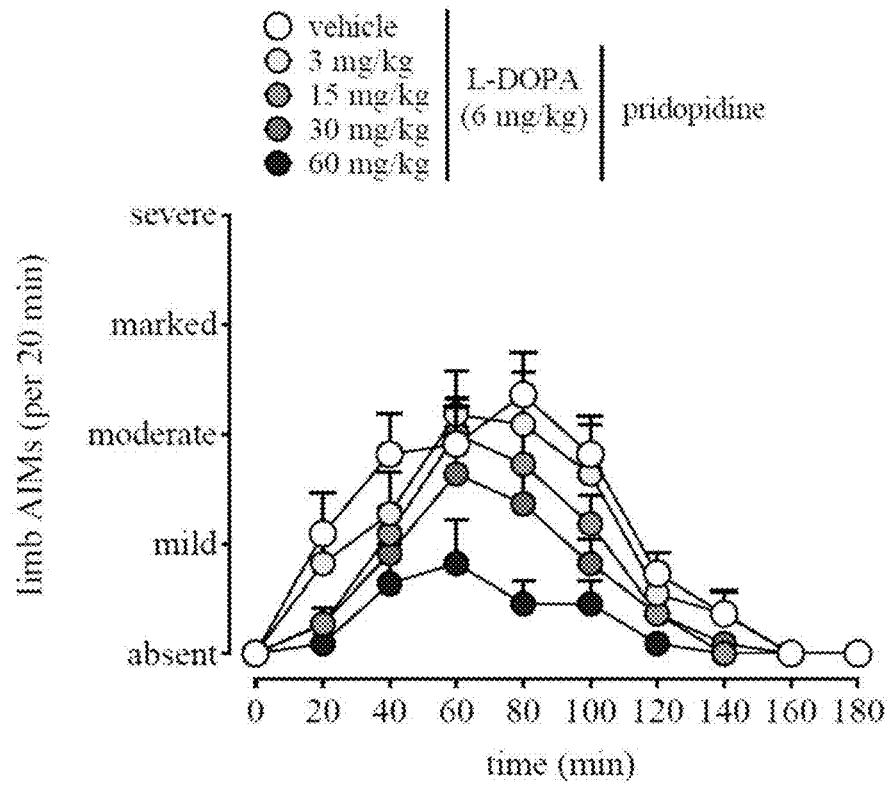
FIGS. 13A-13C present AIMS subscores (time-courses) per 20 minutes of Limb, Axial and Orolingual following treatment with pridopidine at different doses as described in Example 4. Female 6-hydroxydopamine (6-OHDA) lesioned rats treated with L-DOPA followed by treatment of pridopidine at 3 mg/kg, 15 mg/kg, 30 mg/kg and 60 mg/kg doses during 3 hrs.
Figure 13B:
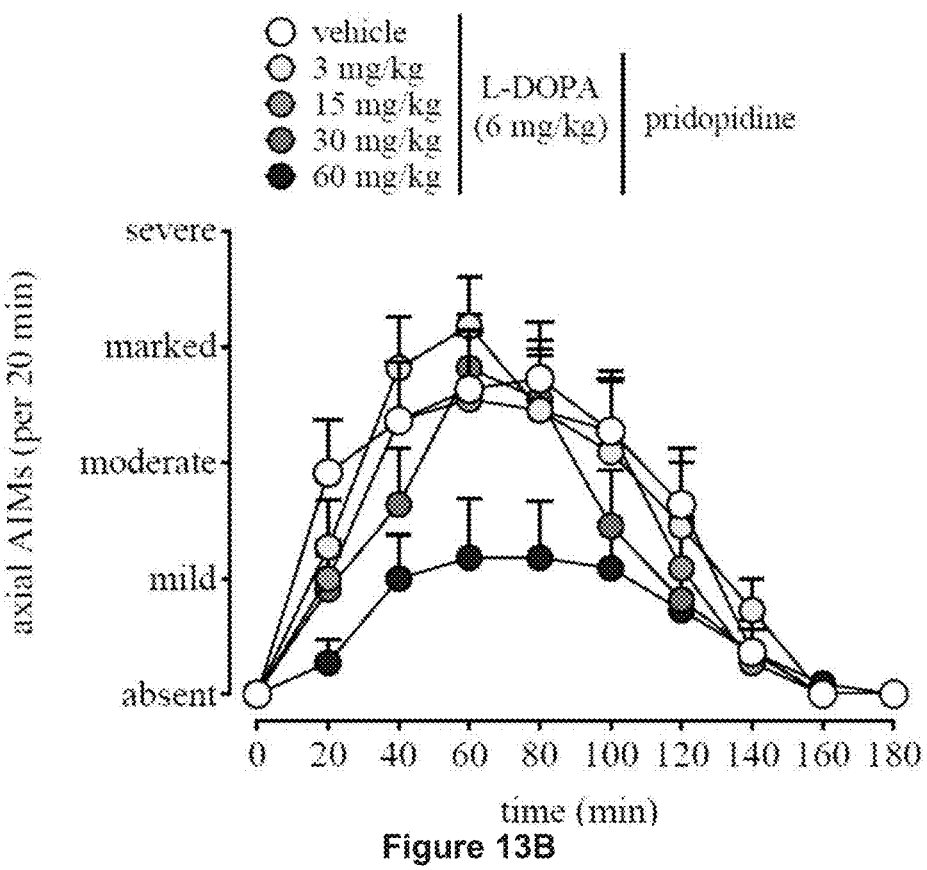
Figure 13C:
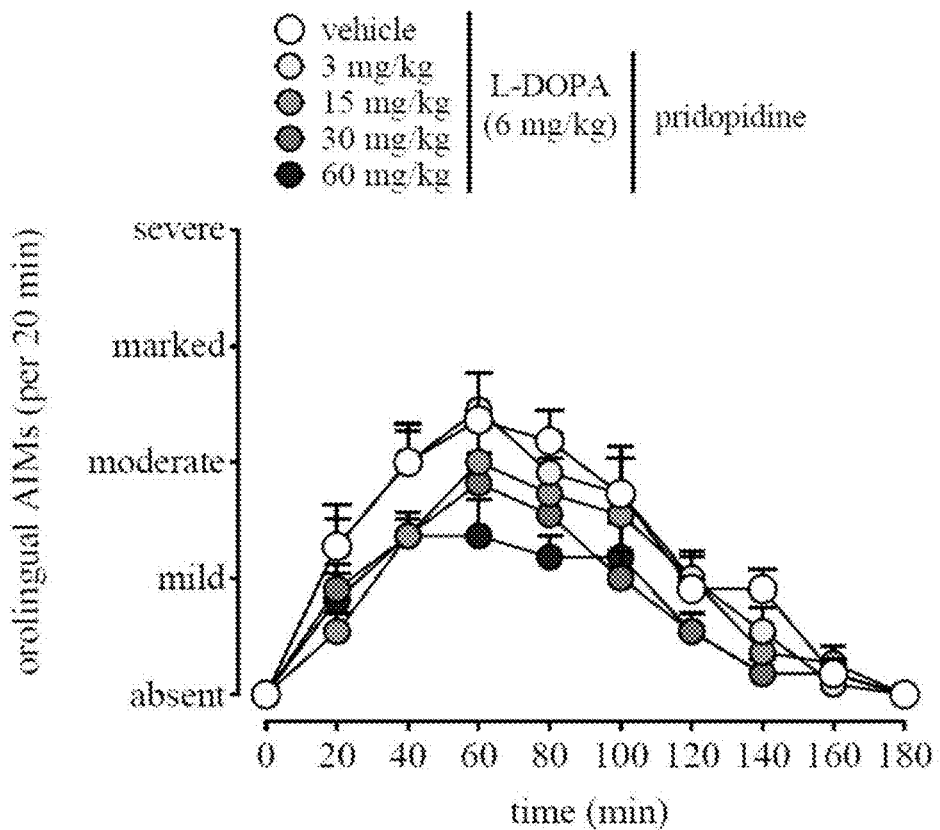
Figure 14A:
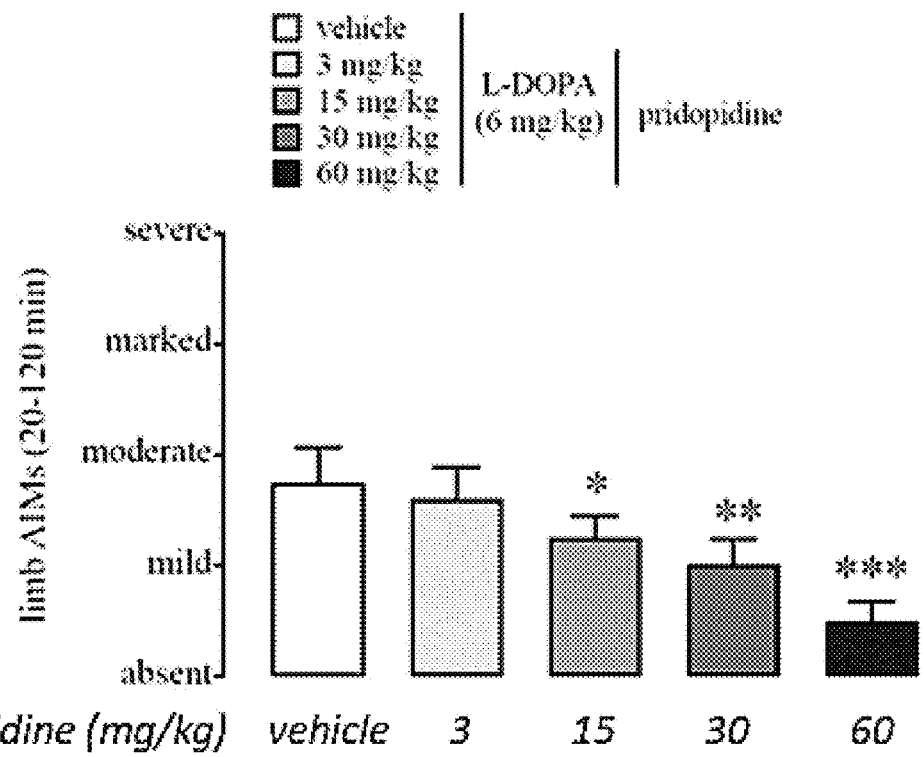
FIGS. 14A-14C are bar graphs presentations of the time course shown in FIG. 13, total of 20-120 min of AIMS subscores bars (Limb, Axial and Orolingual) following treatment with pridopidine at different doses as presented in FIGS. 13A to 13C and described in Example 4.
Figure 14B:
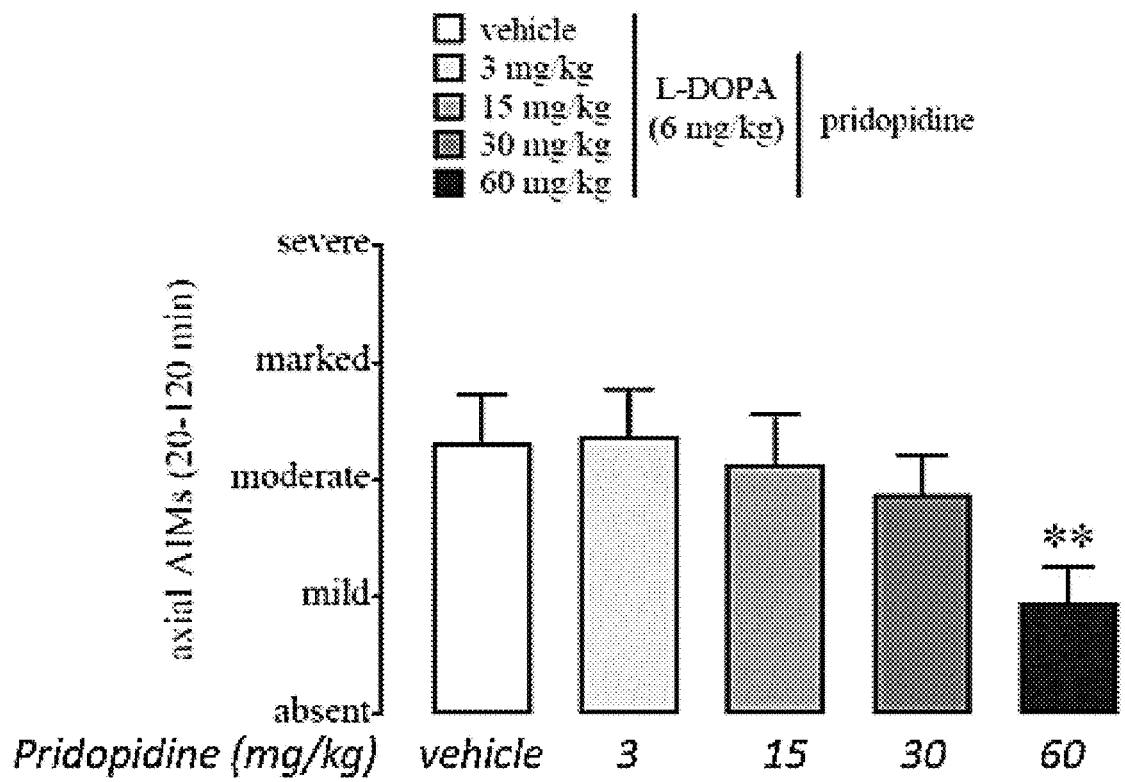
Figure 14C:
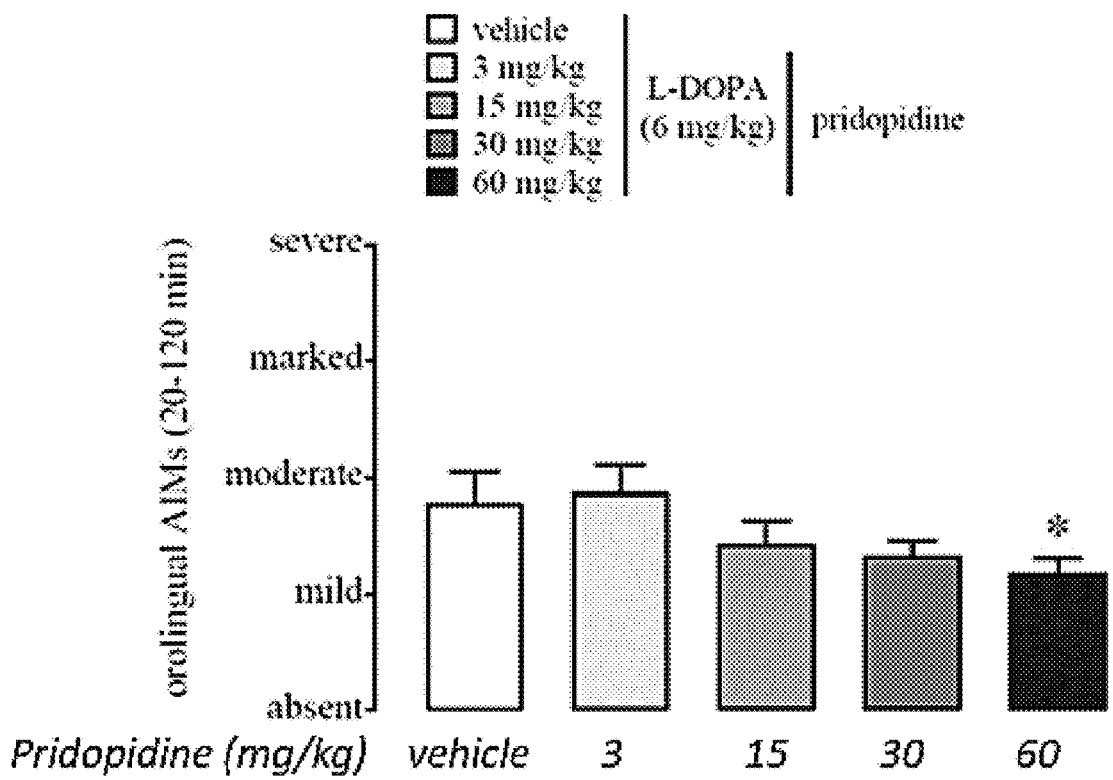

FIGS. 13A-13C present AIMS subscores (time-courses) per 20 minutes of Limb, Axial and Orolingual following treatment with pridopidine at different doses as described above. Female 6-OHDA lesioned rats treated with L-DOPA followed by treatment of pridopidine at 3 mg/kg, 15 mg/kg, 30 mg/kg and 60 mg/kg doses during 3 hrs. FIG. 13A presents the Limb results. Table 10 presents the corresponding p-values to the results presented in FIG. 13A.

TABLE 10

Limb results following treatment of pridopidine

| Pridopidine | L-DOPA/vehicle cf. (min) | | | | |
|---|---|---|---|---|---|
|  | 20 | 40 | 60 | 80 | 100 |
| 3 mg/kg | ns | ns | ns | ns | ns |
| 15 mg/kg | * | * | ns | ns | ns |
| 30 mg/kg | * | ** | ns | ** | ** |
| 60 mg/kg | ** | *** | ** | *** | *** |

* refers to $p < 0.05$,  refers to $p < 0.01$ and * refers to $p < 0.001$.
ns = no signal.

FIG. 13B presents the Axial results. Table 11 corresponding p-values to the results presented in FIG. 13B.

TABLE 11

Axial results following treatment of pridopidine

| Pridopidine | L-DOPA/vehicle cf. (min) | | | | |
|---|---|---|---|---|---|
|  | 20 | 40 | 60 | 80 | 100 |
| 3 mg/kg | ns | ns | ns | ns | ns |
| 15 mg/kg | ns | ns | ns | ns | ns |
| 30 mg/kg | ns | ns | ns | ns | ns |
| 60 mg/kg | ** | ** | ** | ** | * |

* refers to $p < 0.05$, ** refers to $p < 0.01$.
ns = no signal.

FIG. 13C presents the Orolingual results. Table 12 corresponding p-values to the results presented in FIG. 13C.

TABLE 12

Orolingual results following treatment of pridopidine

| Pridopidine | L-DOPA/vehicle cf. (min) | | | | | | |
|---|---|---|---|---|---|---|---|
|  | 20 | 40 | 60 | 80 | 100 | 120 | 140 |
| 3 mg/kg | ns | ns | ns | ns | ns | ns | ns |
| 15 mg/kg | * | * | ns | ns | ns | ns | ns |
| 30 mg/kg | ns | * | ns | * | * | ns | * |
| 60 mg/kg | ns | * | *** | ** | ns | ns | * |

* refers to $p < 0.05$,
** refers to $p < 0.01$ and
*** refers to $p < 0.001$.
ns = no signal.

Combination of Pridopidine and AMT Demonstrates a Synergistic Effect for Reducing AIMS Levels in the 6-OHDA Rat Model of PD To study the effects of the combination of pridopidine and AMT, 6-OHDA rats with established L-DOPA induced AIMS were treated with vehicle, or pridopidine (15 mg/kg, demonstrated to produce suboptimal effects when administered on its own) in combination with vehicle or AMT (5 or 10 mg/kg doses). L-DOPA (6 mg/kg) was administered to induce AIMS, followed by pridopidine, AMT or their combination and AIMS evaluated over a period of 3 hours. L-DOPA treatment induced marked AIMS in 6-OHDA rats. The combination of 15 mg/kg of pridopidine with 5 mg/kg and 10 mg/kg was effective to significantly reduce AIMS to mild levels (FIGS. 15A, time course and 15B, cumulated over 2 hours) more than each drug alone. Table 3 presents corresponding p-values to the results presented in FIG. 15A.

TABLE 13

AIMS levels following treatment of pridopidine and AMT

| Pridopidine | AMT | L-DOPA/vehicle cf. (min) | | | | | | | |
|---|---|---|---|---|---|---|---|---|---|
|  |  | 20 | 40 | 60 | 80 | 100 | 120 | 140 | 160 |
| Vehicle | 5 mg/kg | ns | ns | ns | ns | ns | ns | ns | ns |
| Vehicle | 10 mg/kg | ns | ns | * | ** | ns | ns | ns | ns |
| 15 mg/kg | vehicle | ns | ns | ns | ns | ns | ns | ns | ns |
| 15 mg/kg | 5 mg/kg | ns | * | ** | *** | ns | ** | *** | * |
| 15 mg/kg | 10 mg/kg | *** | *** | *** | *** | *** | *** | *** | ns |

* refers to $p < 0.05$,
** refers to $p < 0.01$ and
*** refers to $p < 0.001$.
ns = no signal.

Figure 15A:
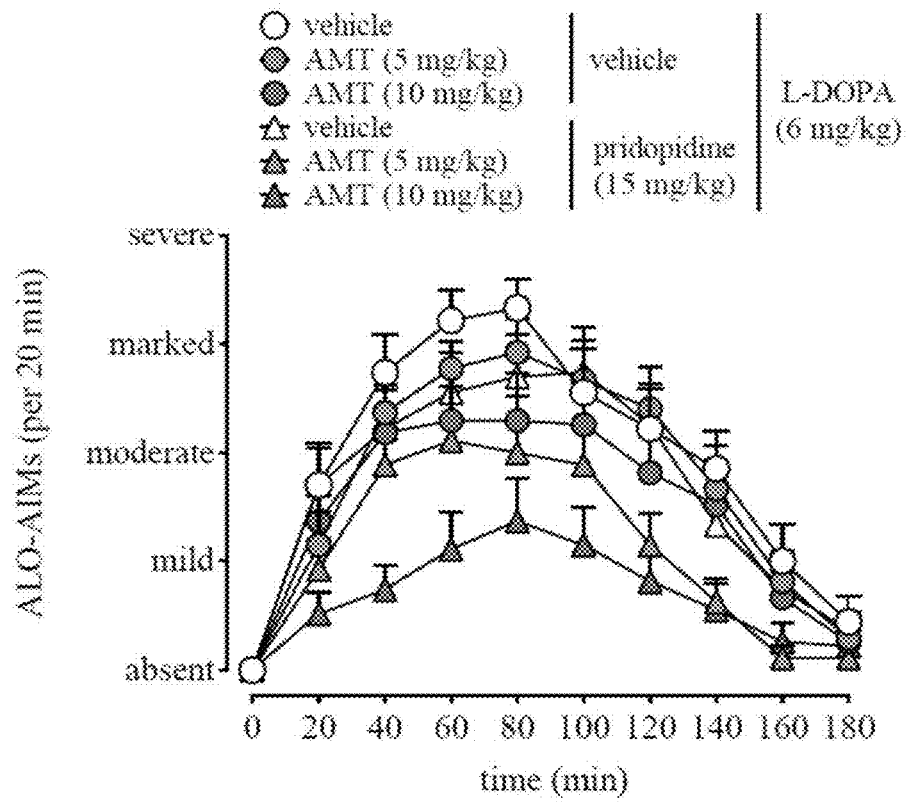
FIGS. 15A-15D present change in levels of AIMS following combination treatment with sub optimal dose pridopidine (15 mg/kg) with either 5 mg/kg or 10 mg/kg amantadine (AMT), as described in Example 4. Amantadine is the gold standard treatment for reducing dyskinesia in PD patients. Female 6-hydroxydopamine (6-OHDA) lesioned rats treated with L-DOPA (6 mg/kg) followed by treatment of pridopidine (15 mg/kg) and amantadine (5 mg/kg or 10 mg/kg) during 3 hrs.
Figure 15B:
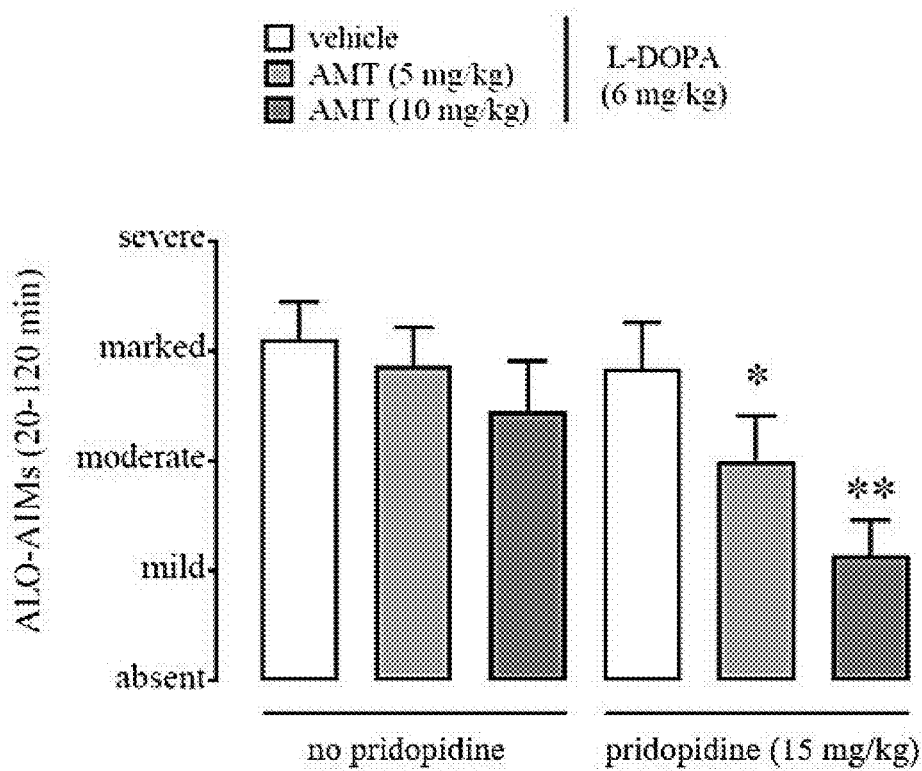
Figure 15C:
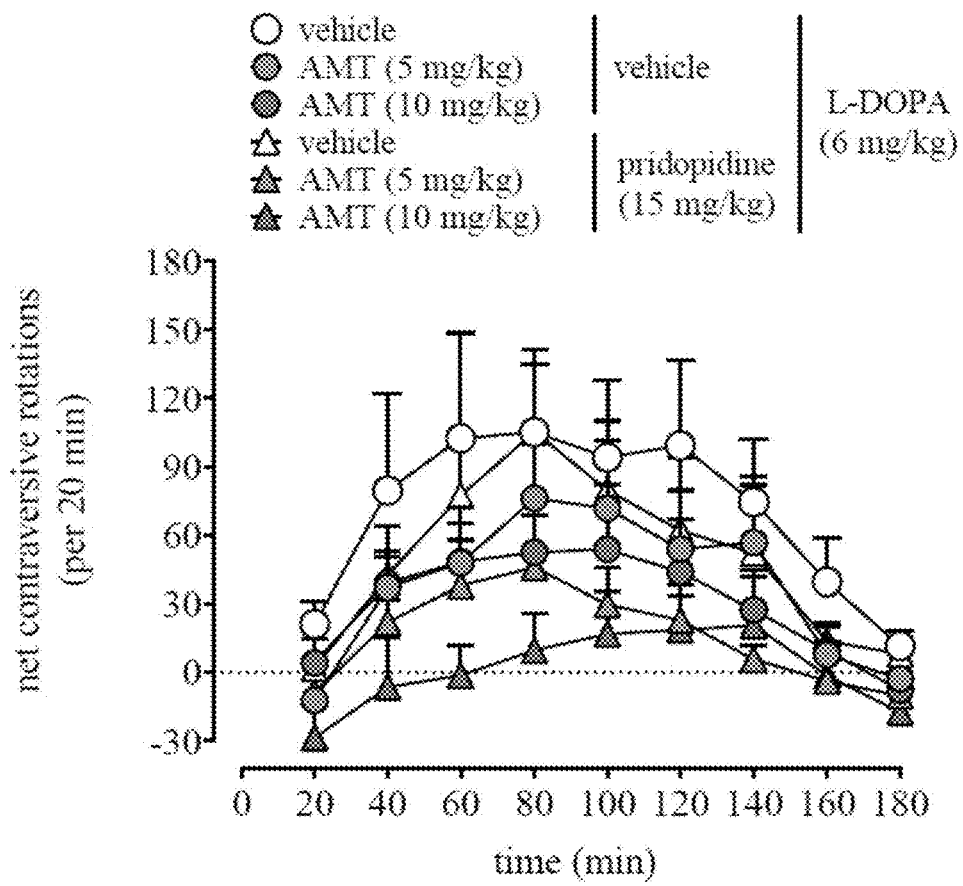
Figure 15D:
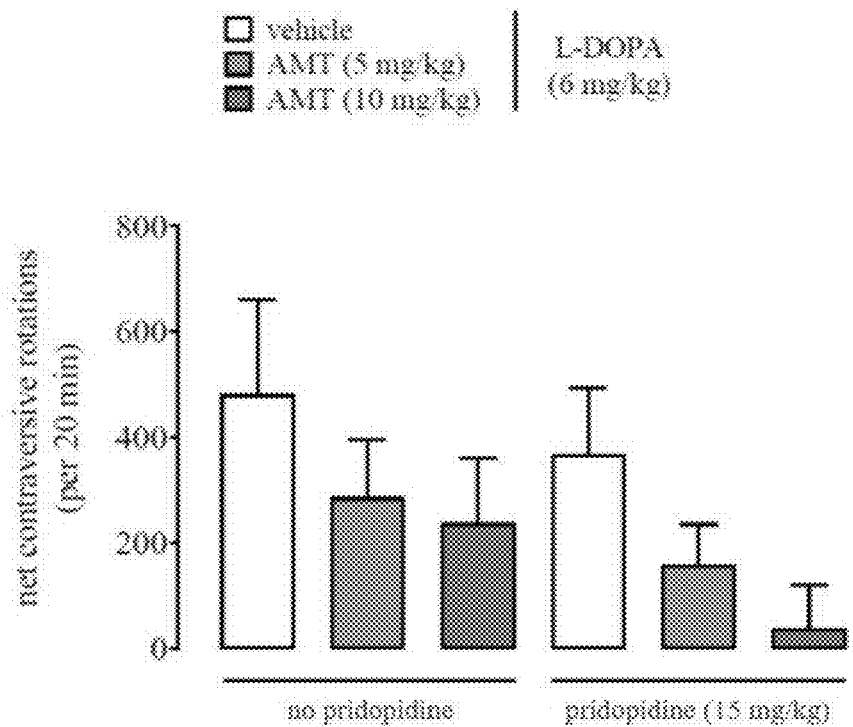

In addition, the net contraversive rotations similarly (NCRs) decrease in response to treatment with the combination of AMT and pridopidine (FIGS. 15C, time course and 15D, 120 min cumulated). Table 14 presents corresponding p-values to the results presented in FIG. 15C.

TABLE 14

Net contraversive rotations following treatment of pridopidine and AMT

| Pridopidine | AMT | L-DOPA/vehicle cf. (min) | | | | | | |
|---|---|---|---|---|---|---|---|---|
|  |  | 20 | 40 | 60 | 80 | 100 | 120 | 140 |
| Vehicle | 5 mg/kg | ns | ns | ns | ns | ns | ns | ns |
| Vehicle | 10 mg/kg | ns | ns | ns | ns | ns | ns | ns |
| 15 mg/kg | vehicle | ns | ns | ns | ns | ns | ns | ns |
| 15 mg/kg | 5 mg/kg | ns | * | * | * | * | ** | ** |
| 15 mg/kg | 10 mg/kg | ns | *** | *** | *** | ** | *** | ns |

* refers to $p < 0.05$,
** refers to $p < 0.01$ and
*** refers to $p < 0.001$.
ns = no signal.

In summary, the combination of pridopidine and AMT produces a clear synergistic effect showing robust and significant reduction of AIMS to an extent that exceeds that achievable by each agent given alone.

The combination of pridopidine and AMT shows a synergistic effect decreasing net contraversive rotations which is typical of an agent with effective anti-AIMs activity. Thus, pridopidine and AMT work synergistically to alleviate L-DOPA induced motor complications. These data suggest a beneficial effect for treating patients afflicted with PD-LID with a combination of pridopidine and AMT. By administering lower doses, tolerability may be increased, and the probability of adverse effects may be reduced.

Example 5: Therapy for Treating LID in PD Patients

Periodically orally administering of pridopidine (greater than 100 mg/day, for example 105 mg/day, 110 mg/day, 135 mg/day, 150 mg/day, 175 mg/day, 180 mg/day, 200 mg/day, 225 mg/day, 250 mg/day, 300 mg/day, 350 mg/day, 400 mg/day) as an add-on therapy for a human subject afflicted with LID who is already receiving levodopa (L-DOPA) provides a clinically meaningful advantage in reducing the symptoms of LID.

The therapy provides efficacy in treating the patient without undue adverse side effects or affecting the safety of the treatment:
1. The therapy is effective in improving symptoms of dyskinesia.

2. The therapy does not produce any significant side effects such as sedation and depression.
3. The therapy does not affect the anti-parkinsonian benefit of levodopa.
4. The therapy improves the bad quality on-time evoked by levodopa.

Example 6: Add-on Therapy for Treating LID in PD Patients

Periodically orally administering of pridopidine (for example 10 mg/day, 15 mg/day, 20 mg/day, 45 mg/day, 90 mg/day, 180 mg/day, 200 mg/day, 225 mg/day, 250 mg/day, 300 mg/day, 400 mg/day, 500 mg/day) as an add-on therapy for a human subject afflicted with LID who is already receiving amantadine provides a clinically meaningful advantage and is more effective (provides at least an additive effect or more than an additive effect) in treating the patient than when administering pridopidine alone (at the same dose).

The add-on therapies also provide efficacy (provides at least an additive effect or more than an additive effect) in treating the patient without undue adverse side effects or affecting the safety of the treatment:

The add-on therapy is effective (provides at least an additive effect or more than an additive effect) in improving symptoms of dyskinesia.

The add-on therapy does not produce any significant side effects such as sedation and depression.

Example 7: Treating DIMD

Periodically orally administering of pridopidine (for example for example 10 mg/day, 15 mg/day, 20 mg/day, 45 mg/day, 90 mg/day, 180 mg/day, 200 mg/day, 225 mg/day, 250 mg/day, 300 mg/day, 400 mg/day, 500 mg/day) as an add-on therapy for a human subject afflicted with a DIMD who is already receiving or has received at least one of antidepressant, an antipsychotic, an antiepileptic, an antimicrobial, an antiarrhythmic, a mood stabilizer, a gastrointestinal drug provides a clinically meaningful advantage in treating the patient.

The therapy also provides efficacy in treating the patient without undue adverse side effects or affecting the safety of the treatment:

The therapy is effective (provides at least an additive effect or more than an additive effect) in improving some or all of the symptoms of DIMD.

The therapy does not produce any significant side effects such as sedation and depression.

Example 8: Estimated Occupancy of Human $S_1R$ and $D_2R$ Receptors

In vivo $S_1R$ and $D_2R$ occupancies were calculated using (i) known binding-affinities of pridopidine to human in-vitro; (ii) in vivo positron-emission tomography imaging in humans and (iii) the extensive PK profiling of pridopidine in the different species.

TABLE 6

Estimated Occupancy of the Human S1R and D2R Receptors at Various Pridopidine Doses

| Species | Dose | Cmax (ng/ml) | AUC0-24 (h * ng/ml) | % S1R occupancy | % D2R occupancy |
|---|---|---|---|---|---|
| Human | 45 mg BID, (90 mg/day, PO) | 618 | 8600 | >90 | ~3 |
|  | 90 mg BID, (180 mg/day, PO) | 1480 | 17300 | >90 | ~30 |
|  | 150 mg BID$^a$ (300 mg/day, PO) | 2550 | 48400 | >90 | >40 |

Abbreviations: AUC, area under the curve; BID, twice daily; Cmax, observed maximum plasma or serum concentration after administration;; PET, positron-emission tomography; PO, per oral.
Human Cmax and AUC values for 45 and 90 mg BID are from Pride-HD (Study TV7820-CNS-20002) and simulated for 150 mg BID.
Human S1R and D2R occupancy at 45 mg BID derived from human PET study TV7820-IMG-10082 and estimated for higher doses.
$^a$Simulated data using the population pharmacokinetic modelling From Tables 2 and 6, it is clear that in the macaques, plasma exposures following the ineffective pridopidine dose (15 mg/kg) are associated with full $S_1R$ (>85%) suggesting $S_1R$ engagement alone is unlikely to account for the anti-dyskinetic benefits of pridopidine that were observed. Exposures in the NHP following effective doses (20 to 30 mg/kg), while still providing full S1R—, provide only modest $D_2R$-occupancy (25-40%). On the other hand, effective pridopidine doses clearly engage a range of receptors (including adrenergic-$\alpha_2C$, dopamine-$D_3$ and serotoninergic-5-$HT_{1A}$ sites) to a greater degree than D2 (Johnston et al 2018).

It is hypothesized that the ability of pridopidine to reduce PD-LID possibly involves a complex pharmacological profile, associated with high S1R occupancy together with multiple non-sigma receptors, including adrenergic $\alpha_2C$, 5-$HT_{1A}$, and DA receptors.

Example 9: Treatment of Levodopa-Induced Dyskinesia (LID) in Patients with Parkinson's Disease (PD)

This is a 14-week, Phase 2B, multicenter, randomized, double-blind, placebo-controlled, three-arm, parallel-group study to evaluate the efficacy, safety, and PK of pridopidine 100 mg bid (oral capsule) and 150 mg bid (oral capsule) vs placebo for the treatment of PD-LID (Levodopa-Induced Dyskinesia in Patients with Parkinson's Disease), Study Objectives Primary Objective: To evaluate the efficacy of 2 dosages of pridopidine (100 mg twice daily bid and 150 mg bid) vs placebo for the treatment of PD-LID.

Inclusion Criteria

Patients may be included in the study only if they meet the following criteria:

Has clinical diagnosis of Parkinson's Disease (PD).

Has mild-to-moderate Levodopa-induced dyskinesia (LID).

Efficacy Endpoints

Primary endpoint will be assessed for both the 100 mg bid and the 150 mg bid pridopidine dosages vs placebo in a hierarchical manner.

Primary Endpoint/Outcome Measure:

The primary endpoint is the mean change from Baseline (Visit 2) to Visit 7/ET in the sum of Parts 1, 3, and 4 of the Unified Dyskinesia Rating Scale (UDysRS) dose dyskinesia.

Example 10: Therapy for Treating DIMD by Administering Combination of Pridopidine and an Additional Therapeutic Agent Periodically orally administering of pridopidine (for example 10 mg/day, 15 mg/day, 20 mg/day, 45 mg/day, 90 mg/day, 180 mg/day, 200 mg/day, 225 mg/day, 250 mg/day, 300 mg/day, 350 mg/day, 400 mg/day or 500 mg/day) and one or more additional therapeutic agent as an add-on therapy for a human subject afflicted with LID who is already receiving levodopa (L-DOPA) provides a clinically meaningful advantage in reducing the symptoms of LID.

The additional therapeutic agent includes Amantadine, Dipraglurant (ADX48621), Foliglurax, mesdopetam (IRL790), Eltoprazine, Buspirone, Levetiracetam, and Nuedexta (dextromethorphan/Quinidine), or a combination thereof.

The therapy provides efficacy in treating the patient without undue adverse side effects or affecting the safety of the treatment:
1. The therapy is effective in improving symptoms of dyskinesia.
2. The therapy does not produce any significant side effects such as sedation and depression.
3. The therapy does not affect the anti-parkinsonian benefit of levodopa.
4. The therapy improves the bad quality on-time evoked by levodopa.

REFERENCES

"Huntexil®", The NeurosSearch website, retrieved Sep. 24, 2012, http://neurosearch.com/Default.aspx?ID=8172.

Amantadine PDR 2017 Amantadine hydrochloride—Drug Summary, PDR (Prescribers' Digital Reference), http://www.pdr.net/drug-summary/Amantadine-Hydrochloride-Tablets-amantadine-hydrochloride-2441 and http://www.pdr.net/drug-summary/Amantadine-Hydrochloride-Capsules-amantadine-hydrochloride-1475 accessed Sep. 7, 2017

Bargiotas P. and Konitsiotis S. 2013. Levodopa-induced dyskinesias in Parkinson's disease: emerging treatments. Neuropsychiatric Disease and Treatment. 9:1605-1617.

Bezchlibnyk-Butler K Z, Remington G J. Antiparkinsonian drugs in the treatment of neuroleptic-induced extrapyramidal symptoms. Can J Psychiatry. 1994 March; 39(2):74-84. doi: 10.1177/070674379403900203. PMID: 7908605.

Brod et al. 2000 Combination therapy with glatiramer acetate (copolymer-1) and a type I interferon (IFN-α) does not improve experimental autoimmune encephalomyelitis. Annals of Neurology, 47:127-131.

Brust et al. 2014. Molecular Imaging of al Receptors In Vivo: Current Status and Perspectives. Curr. Med. Chem. 21, 35-69.

CSID:25948790, www.chemspider.com/Chemical-Structure.25948790.html (accessed 23:27, Jul. 15, 2016).

CSID:7971505, www.chemspider.com/Chemical-Structure.7971505.html (accessed 23:33, Jul. 15, 2016).

Cubo et al. 2001. Early morning off-medication dyskinesias, dystonia, and choreic subtypes. Arch. Neurol. 58(9):1379-1382.

Daneault, J-F. 2013. Drug-induced dyskinesia in Parkinson's disease. Should success in clinical management be a function of improvement of motor repertoire rather than amplitude of dyskinesia? BMC Medicine, 11:76.

de Yebenes J G, Landwehrmeyer B, Squitieri F, Reilmann R, Rosser A, Barker R A, Saft C, Magnet M K, Sword A, Rembratt A, Tedroff J; MermaiHD study investigators. Pridopidine for the treatment of motor function in patients with Huntington's disease (MermaiHD): a phase 3, randomised, double-blind, placebo-controlled trial. Lancet Neurol. 2011 December; 10(12):1049-57. doi: 10.1016/S1474-4422(11)70233-2. Epub 2011 Nov. 7. PMID: 22071279.

Dizdar, N., et al., 1999. Human pharmacokinetics of L-3,4-dihydroxyphenylalanine studied with microdialysis. Clin Chem 45, 1813-1820.

Ecdeu, G W. 1976. Abnormal Involuntary Movement Scale (AIMS) Assessment Manual for Psychopharmacology: Revised (DHEW publication number ADM 76-338). Rockville, MD, US Department of Health, Education and Welfare, Public Health Service, Alcohol, Drug Abuse and Mental Health Administration, NIMH Psychopharmacology Research Branch, Division of Extramural Research Programs, 1976: 534-7.

FDA (1999) Guidance for Industry: In Vivo Drug Metabolism/Drug Interaction Studies—Study Design, Data Analysis, and Recommendations for Dosing and Labeling.

Gerber P E, Lynd L D. 1998. Selective serotonin-reuptake inhibitor-induced movement disorders. Ann Pharmacother 32: 692-698

Geva M, et al., 2016. Pridopidine activates neuroprotective pathways impaired in Huntington Disease. Hum Mol Genet. 25(18):3975-3987.

Goetz et al; 2007. Movement Disorder Society-sponsored revision of the Unified Parkinson's Disease Rating Scale (MDS-UPDRS): Process, format, and clinimetric testing plan. Movement Disorders 22(1):41-7.

Goetz et al: 2008a. Movement Disorder Society-sponsored revision of the Unified Parkinson's Disease Rating Scale (MDS-UPDRS): Scale Presentation and Clinimetric Testing Results. Movement Disorders 23(15):2129-2170.

Goetz, et al. 2008b. The Unified Dyskinesia Rating Scale: Presentation and Clinimetric Profile. Movement Disorders 23(16):2398-2403.

Goetz, et al 2013 Which Dyskinesia Scale Best Detects Treatment Response? Movement Disorders 28(3):341-346 Hauser, et al. 2004. Parkinson's disease home diary: Further validation and implications for clinical trials. Movement Dis. 19(12): 1409-1413.

Hauser R A, Deckers F, Lehert P. Parkinson's disease home diary: further validation and implications for clinical trials. Mov Disord. 2004 December; 19(12):1409-13. doi: 10.1002/mds.20248. PMID: 15390057.

Huntington Study Group HART Investigators. A randomized, double-blind, placebo-controlled trial of pridopidine in Huntington's disease. Mov Disord. 2013 September; 28(10):1407-15. doi: 10.1002/mds.25362. Epub 2013 Feb. 28. PMID: 23450660.

Huot, P, et al, 2012. L-DOPA pharmacokinetics in the MPTP-lesioned macaque model of Parkinson's disease. Neuropharmacology 63, 829-836.

Jankelowitz S K. Treatment of neurolept-induced tardive dyskinesia. Neuropsychiatr Dis Treat. 2013:9:1371-80. doi: 10.2147/NDT.S30767. Epub 2013 Sep. 16. PMID: 24072972; PMCID: PMC3783506.

Johnston, T H et al. and Lee, C S. 2001. "Levodopa-induced dyskinesia: Mechanisms and management" BCMJ 43(4), 206-9.

Johnston, T H, et al, 2013. TC-8831, a nicotinic acetylcholine receptor agonist, reduces L-DOPA-induced dyskinesia in the MPTP macaque. Neuropharmacology 73, 337-347.

Johnston T H, Geva M. Steiner L, Orbach A, Papapetropoulos S., Savola J M, et al. Pridopidine, a clinic-ready compound, reduced 3,4-dihydroxyphenylalanine-induced dyskinesia in parkinsonian macaques. Mov. Disord. Equb 2018 Dec. 21.

Johnston T H, Geva M, Steiner L, Orbach A, Papapetropoulos S, Savola J M, Reynolds U, Ravenscroft P, Hill M, Fox S H, Brotchie J M, Laufer R, Hayden M R. Pridopidine, a clinic-ready compound, reduces 3,4-dihydroxyphenylalanine-induced dyskinesia in Parkinsonian macaques. Mov Disord. 2019 May; 34(5):708-716. doi: 10.1002/mds.27565. Epub 2018 Dec. 21. PMID: 30575996.

Kumar, N., et al, 2005 Levodopa-dyskinesia incidence by age of Parkinson's disease onset. Mov Disord. 20, 342-344.

Manson, A., et al, 2012 Levodopa-induced-dyskinesias clinical features, incidence, risk factors, management and impact on quality of life. J Parkinsons Dis 2, 189-198.

Marder K, et al. 2000. Rate of functional decline in Huntington's disease. Neurology 54:452-458.

Movement Disorder Society Task Force on Rating Scales for Parkinson's Disease. 2003. Unified Parkinson's Disease Rating Scale (UPDRS): status and recommendations. Movement Disorders 18(7):738-50.

National Research Council Institute for Laboratory Animal, R., Guide for the Care and Use of Laboratory Animals. National Academies Press (US). Copyright 1996 by the National Academy of Sciences. All rights reserved, Washington (DC).

Poewe, W., Mahlknecht, P., 2009. The clinical progression of Parkinson's disease. Parkinsonism Relat Disord.15 Suppl 4, S28-32.

Ponten H, et al. 2010. In vivo pharmacology of the dopaminergic stabilizer pridopidine. Eur J Pharmacol. 644(1-3):88-95.

Ponten H, et al. 2013. The dopaminergic stabilizer pridopidine decreases expression of L-DOPA-induced locomotor sensitisation in the rat unilateral 6-OHDA model. Eur J Pharmacol. 698(1-3):278-85.

Sahlholm K, et al. 2013. The dopamine stabilizers ACR16 and (−)-OSU6162 display nanomolar affinities at the σ-1 receptor. Mol Psychiatry. 18:12-14.

Sahlholm K, et al. 2015. Pridopidine selectively occupies sigma-1 rather than dopamine D2 receptors at behaviorally active doses. Psychopharmacol (Berl) 232(18):3443-3453.

Shoulson and Fahn. 1979. Huntington disease: clinical care and evaluation. Neurology 29:1-3.

Slifstein et al. 2010. Striatal and Extrastriatal Dopamine Release Measured With PET and [F-18] Fallypride. Synapse 64(5):350-62.

Tedroff, J, et al. 2004. A pilot study of the novel dopamine stabiliser ACR16 in advanced Parkinson's disease. Movement Disorders, Vol. 19, Suppl. 9, P565.

U.S. Pat. No. RE46117 (Sonesson, et al.)

U.S. Pat. No. 7,923,459, issued Apr. 12, 2011 (Gauthier, et al.)

PCT International Application Publication No. WO2014/205229

PCT International Application Publication No. WO 2017/015609

PCT International Application Publication No. WO2018/039477

What is claimed is:

1. A method of treating levodopa-induced dyskinesia (LID) in a subject in need thereof, comprising a combination therapy of administering to the subject pridopidine or pharmaceutically acceptable salt thereof, and amantadine.

2. The method of claim 1, wherein the subject is afflicted with Parkinson's disease.

3. The method of claim 1, wherein the subject is afflicted with parkinsonism other than Parkinson's disease.

4. The method of claim 1, wherein the subject is concurrently being treated with levodopa.

5. The method of claim 4 wherein the pridopidine, amantadine and the levodopa are administered sequentially or contemporaneously.

6. The method of claim 4 wherein the pridopidine and amantadine are administered after the levodopa is administered for a period of time.

7. The method of claim 6, wherein the period of time is from 10 min to 18 hours.

8. The method of claim 7, wherein the period of time is 10 min, 20 min, 30 min, 45 min, 1.0 hour, 2.0 hours, 6.0 hours, or 12 hours or 18 hours.

9. The method of claim 1, wherein the pridopidine and amantadine are administered sequentially or contemporaneously.

10. The method of claim 1 wherein pridopidine and the amantadine are co-formulated.

11. The method of claim 1, wherein the pridopidine and the amantadine are administered in a separate pharmaceutical formulation.

12. The method of claim 4, wherein the levodopa is administered after the pridopidine and amantadine are administered for a period of time.

13. The method of claim 1, wherein the method further alleviates or reduce a symptom associated with the levodopa treatment.

14. The method of claim 1, pridopidine or pharmaceutically acceptable salt thereof and amantadine have synergistic activity and are effective to alleviate or reduce a symptom associated with the levodopa treatment.

15. The method of claim 13, wherein the symptom is abnormal movements, myoclonic jerks, irregular movements of extremities, gait, facial grimacing, ataxia, inability to sustain motor act, hand movement or balance, choreiform peak dose dyskinesia, or dystonic peak dose dyskinesia.

16. The method of claim 13, wherein the symptom is bad quality on-time evoked by levodopa.

17. The method of claim 13, wherein the administration of pridopidine and amantadine improves the symptom of the levodopa induced dyskinesia by at least 8%, by at least 20%, by at least 30% or by at least 50% as measured by MDS-UPDRS or UDysRS.

18. The method of claim 1, wherein the pridopidine or pharmaceutically acceptable salt thereof and amantadine are administered via oral administration.

19. The method of claim 1, wherein pridopidine or pharmaceutically acceptable salt thereof, and amantadine are administered once daily, twice daily, three times daily, four times daily, or less than once a day.

20. The method of claim 1, wherein pridopidine is administered as a pridopidine salt.

21. The method of claim 19, wherein the salt is pridopidine HCl salt.

22. The method of claim 1, wherein pridopidine is administered in a daily dose of between 10-400 mg/day.

23. The method of claim 1, wherein pridopidine is administered in a daily dose of between 150-400 mg/day.

24. The method of claim 1, wherein the pridopidine is administered at a daily dose of 200 mg given in the form of pridopidine HCl.

25. The method of claim 1, wherein the method further delays the onset of LID or reduce the risk of developing LID.

26. The method of claim 1, wherein the subject is receiving levodopa for treatment of Parkinson's disease.

27. The method of claim 1, wherein the pridopidine or pharmaceutically acceptable salt thereof is administered in equal doses, twice daily.

28. The method of claim 1, wherein amantadine is administered at a daily dose of between 10 mg to 400 mg/day.

29. The method of claim 1, wherein the weight ratio between the pridopidine and amantadine is between 1:20 to about 20:1.

* * * * *